United States Patent
Bjornsson et al.

(10) Patent No.: US 10,568,854 B2
(45) Date of Patent: Feb. 25, 2020

(54) COMPOSITIONS AND METHODS FOR TREATING KABUKI SYNDROME AND RELATED DISORDERS

(71) Applicant: THE JOHNS HOPKINS UNIVERSITY, Baltimore, MD (US)

(72) Inventors: Hans Tomas Bjornsson, Baltimore, MD (US); Harry Dietz, Towson, MD (US); Joel Benjamin, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 278 days.

(21) Appl. No.: 15/315,172

(22) PCT Filed: May 29, 2015

(86) PCT No.: PCT/US2015/033215
§ 371 (c)(1),
(2) Date: Nov. 30, 2016

(87) PCT Pub. No.: WO2015/184279
PCT Pub. Date: Dec. 3, 2015

(65) Prior Publication Data
US 2017/0100354 A1 Apr. 13, 2017

Related U.S. Application Data

(60) Provisional application No. 62/005,607, filed on May 30, 2014, provisional application No. 62/155,234, filed on Apr. 30, 2015.

(51) Int. Cl.
| | | |
|---|---|---|
| A61K 31/19 | (2006.01) |
| A23L 33/00 | (2016.01) |
| A61K 31/20 | (2006.01) |
| A61K 31/167 | (2006.01) |
| A61K 31/55 | (2006.01) |
| A61K 31/166 | (2006.01) |
| A61K 31/23 | (2006.01) |
| G01N 33/64 | (2006.01) |

(52) U.S. Cl.
CPC .............. *A61K 31/19* (2013.01); *A23L 33/30* (2016.08); *A23L 33/40* (2016.08); *A61K 31/166* (2013.01); *A61K 31/167* (2013.01); *A61K 31/20* (2013.01); *A61K 31/23* (2013.01); *A61K 31/55* (2013.01); *G01N 33/64* (2013.01); *A23V 2002/00* (2013.01); *G01N 2800/52* (2013.01); *G01N 2800/7033* (2013.01)

(58) Field of Classification Search
None
See application file for complete search history.

(56) References Cited

U.S. PATENT DOCUMENTS

2008/0058416 A1  3/2008  Greenwood et al.

FOREIGN PATENT DOCUMENTS

WO    2012149472 A2   11/2012

OTHER PUBLICATIONS

Klepper et al. "Glut1 Deficiency Syndrome and Novel Ketogenic Diets" Journal of Child Neurology 28(8) 1045-1048, Published May 10, 2013 (Year: 2013).*
Bough et al. "Anticonvulsant Mechanisms of the Ketogenic Diet" Epilepsia, 48(1):43-58, 2007 (Year: 2007).*
Klepper et al. "Glut1 Deficiency Syndrome and Novel Ketogenic Diets" Journal of Child Neurology 28(8) 1045-1048 (Year: 2013).*
Novelli "Baldness as a mendelian genetic trait" Molecular Medicine Today, Apr. 1998, p. 143 (Year: 1998).*
Benjamin et al. "A ketogenic diet rescues hippocampal memory defects in a mouse model of Kabuki syndrome" PNAS Jan. 3, 2017, vol. 114, No. 1, 125-130, published online Dec. 20, 2016 (Year: 2016).*
International Search Report and Written Opinion dated Aug. 28, 2015, from related PCT Patent Application No. PCT/US15/033215.
Fois, A., "Infantile spasms: review of the literature and personal experience," Italian Journal of Pediatrics, 2010, vol. 36, Article No. 15, internal pp. 1-10.
Henderson, S.T., "Ketone bodies as a therapeutic for Alzheimer's disease," Neurotherapeutics, 2008, vol. 5, No. 3, pp. 470-480.
Van der Meulen, J. et al., "The H3K27me3 demethylase UTX in normal development and disease," Epigenetics, Epub. Feb. 21, 2014, vol. 9, No. 5, pp. 658-668.

* cited by examiner

Primary Examiner — Thane Underdahl
(74) Attorney, Agent, or Firm — Casimir Jones, S.C.; Jeffrey W. Childers

(57) ABSTRACT

A method is provided for treating a Mendelian disorder of the epigenetic machinery (e.g., Kabuki syndrome) in a subject in need thereof. In particular, the method comprises administering to the subject a ketogenic composition in an amount sufficient to produce a physiologically acceptable ketosis in the subject. A method for selecting a subject for treatment of a Mendelian disorder of the epigenetic machinery (e.g., Kabuki syndrome) is also provided. Ketogenic compositions and kits useful for practicing the methods are also provided.

25 Claims, 61 Drawing Sheets

Specification includes a Sequence Listing.

Human:                                                                      Chr:
Mouse:
▨ = PHD zinc finger        ▨ = FYRN domain
▨ = HMG box                ▨ = FYRC domain
▨ = Post-SET domain        ▨ = SET methyltransferase domain
*FIG. 5A*
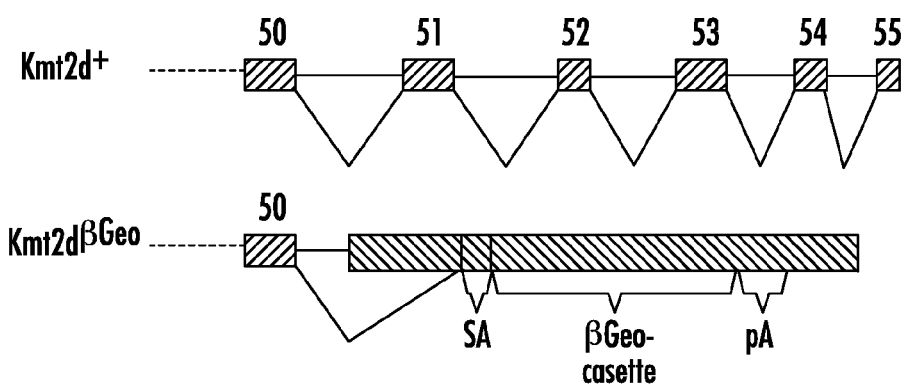
*FIG. 5B*

Exact integration site:

CTGTGTGGAACCGCATCATTGAGCCTGTGGCTGCCATGAGAAAGAAGCC
GACATGCTGAGACTCTTCCCCGAGTACCTGAAAGGCGAAGAACTCTTTGG
GCTGACAGTGCATGCAGTGCTTCGCATAGCTGAATCGGTAAGCAAGCGGC
AAGGAGCTGGGGCCAAGGTGGGAATACTTACTGTATGGCGTGCGGGTGT
GTGTGACCGTGGGTACACTTAAAACACCGGGTTTTGGATCTGCACTGTCCC
GGATGTCCTCTGGTGCTCAAAGACCCTTTTGGGTTTGCCCTTTGGTAAGA
GCGCCGGGATCTACTTGTCTGGAGGCCAGGGAGTCCTCAGCCGAGGCTT
GCCGCCCTGACTGCACTGCACTGAGTAGT (SEQ ID NO: 7)

FIG. 6A

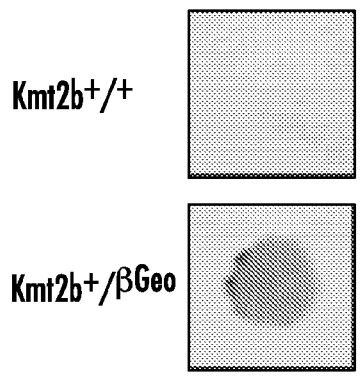

FIG. 6B

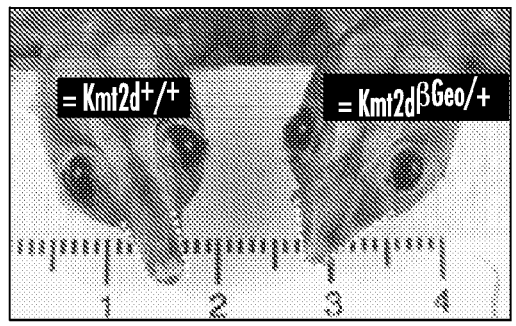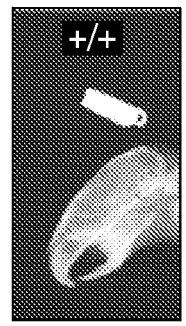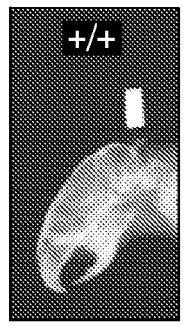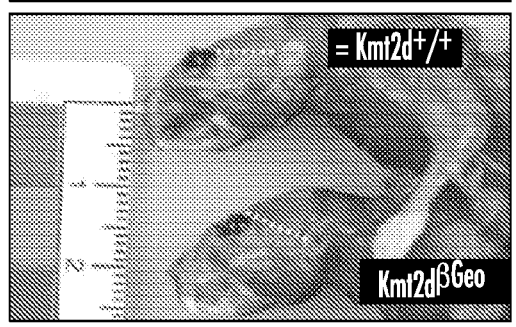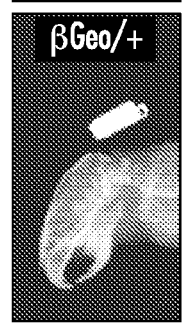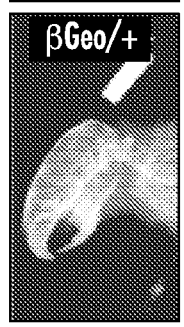
*FIG. 7A*  *FIG. 7B*
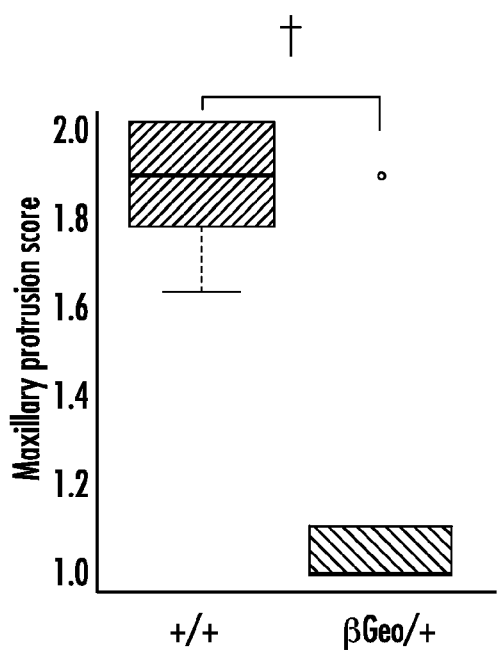
*FIG. 7C*

H4ac indicator
K5, K8, K12, K16, K20
H3K4me3 indicator
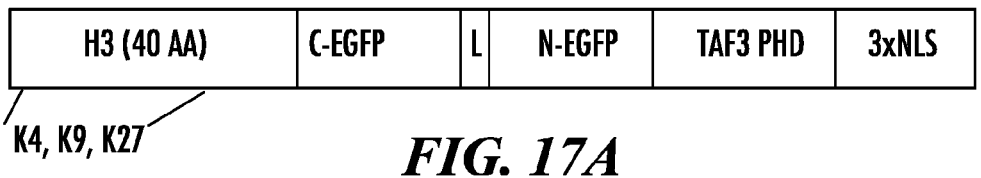
K4, K9, K27
*FIG. 17A*
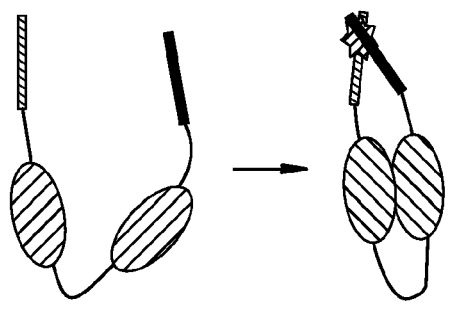
▨ Histone tail
▮ Histone reader
✦ Histone modification
*FIG. 17B*

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
caaatggcga ttaccgttga                                           20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tgcccagtca tagccgaata                                           20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
caaatgttgc ttgtctggtg                                           20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
gtcagtcgag tgcacagttt                                           20

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
ctgcgcgcaa gtcaacgggt g                                         21

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
atgccgttct tctgcttgtc g                                         21

<210> SEQ ID NO 7
<211> LENGTH: 379
<212> TYPE: DNA
<213> ORGANISM: Artificial Sequence
<220> FEATURE:
<223> OTHER INFORMATION: Mouse Kmt2d exon 50/intron 50/ beta-Geo
      cassette

<400> SEQUENCE: 7
ctgtgtggaa ccgcatcatt gagcctgtgg ctgccatgag aaaagaagcc gacatgctga      60
gactcttccc cgagtacctg aaaggcgaag aactctttgg gctgacagtg catgcagtgc     120
ttcgcatagc tgaatcggta agcaagcggc aaggagctgg ggccaaggtg ggaatactta     180
ctgtatggcg tgcgggtgtg tgtgaccgtg ggtacactta aaacaccggg ttttggatct     240

```
gcactgtccc ggatgtcctc tggtgctcaa agacccttttt gggtttgccc tttggtaaga    300
gcgccgggat ctacttgtct ggaggccagg gagtcctcag ccgaggcttg ccgcccctga    360
ctgcactgca ctgagtagt                                                 379
```

COMPOSITIONS AND METHODS FOR TREATING KABUKI SYNDROME AND RELATED DISORDERS

CROSS-REFERENCE TO RELATED APPLICATIONS

This application is a 35 U.S.C. § 371 National Stage Entry of International Application No. PCT/US15/033215 having an international filing date of May 29, 2015, which claims the benefit of U.S. Provisional Application No. 62/005,607, filed May 30, 2014, and U.S. Provisional Application No. 62/155,234, filed Apr. 30, 2015, which are incorporated herein by reference in their entirety.

FEDERALLY SPONSORED RESEARCH OR DEVELOPMENT

This invention was made with government support under DP5OD017877 awarded by the National Institutes of Health (NIH). The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00416 _ST25. txt". The sequence listing is 2,046 bytes in size, and was created on May 22, 2015. It is hereby incorporated by reference in its entirety.

BACKGROUND

Mendelian disorders of the epigenetic machinery are a newly delineated group of multiple congenital anomaly and intellectual disability syndromes resulting from mutations in genes encoding components of the epigenetic machinery. The gene products affected in these inherited conditions act in trans and are expected to have widespread epigenetic consequences. The DNA methylation machinery and the histone machinery affect the expression of many genes in trans (Berdasco & Esteller (2013) *Hum. Genet.* 132:359-83; Wolffe (1994) *Trends Biochem. Sci.* 19:240-44). Within this group, genetic mutations may occur in writers, erasers, or readers of epigenetic marks. The writers of epigenetic marks, which can be conceptualized as a set of highlighters, place the appropriate modifications on particular regions of the genome based on the cell type, developmental stage, and metabolic state of the cell. These marks "highlight" individual regions for use or disuse depending on whether the mark favors a more open or more closed chromatin state. The erasers of epigenetic marks remove these same marks, favoring the opposite chromatin states. The readers of epigenetic marks recognize and interpret particular marks locally and give cells a mechanism for keeping track of the overall chromatin state.

Mendelian disorders of the histone machinery have been described for writers, erasers, readers, and chromatin remodelers. The histone writer and eraser system is unique because it involves opposing players that must achieve a balance of activity and subsequently of histone marks at particular target genes in any given cell state (FIG. 1). This idea is illustrated by Kabuki syndrome (KS), which can be caused by a defect in either a writer or an eraser. KS is an autosomal dominant or X-linked intellectual disability syndrome with specific dysmorphic features, including a flattened facial appearance with characteristic eyes exhibiting long palpebral fissures, eversion of the lower lids, highly arched eyebrows, and long eyelashes, as well as short stature.

KS is caused by heterozygous loss-of-function mutations in either of two genes with complementary functions, lysine-specific methyltransferase 2D (KMT2D) on human chromosome 12 (also known as mixed lineage leukemia 2 or MLL2; Ng et al. (2010) *Nat. Genet.* 42:790-3) or lysine-specific demethylase 6A (KDM6A) on human chromosome X (Lederer et al. (2012) *Am. J. Hum. Genet.* 90:119-24) (FIG. 2). KMT2D is a methyltransferase that adds a trimethylation mark to H3K4 (H3K4me3, an open chromatin mark) while KDM6A is a demethylase that removes trimethylation from histone 3 lysine 27 (H3K27me3, a closed chromatin mark). Both genes facilitate the opening of chromatin and promote gene expression (Ng et al. (2010) *Nat. Genet.* 42:790-3; Lederer et al. (2012) *Am. J. Hum. Genet.* 90:119-24; Miyake et al. (2013) *Hum. Mutat.* 34:108-10).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science,* and *Current Protocols in Cell Biology,* all John Wiley & Sons, N.Y., edition as of December 2008; Sambrook, Russell, and Sambrook, *Molecular Cloning. A Laboratory Manual,* 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The presently disclosed subject matter relates to the discovery that a reversible deficiency of postnatal neurogenesis in the granule cell layer of the dentate gyrus associated with intellectual disability in KS can be ameliorated postnatally by agents that favor open chromatin states. In particular, the presently disclosed subject matter provides methods for treating KS and other Mendelian disorders of the epigenetic machinery using agents that restore balance between open and closed chromatin states at one or more target genes.

In one aspect, the presently disclosed subject matter provides a method for treating a subject in need of therapy for a Mendelian disorder of The epigenetic machinery, comprising administering to the subject a ketogenic composition in an amount sufficient to produce a physiologically acceptable ketosis in the subject. In certain aspects, the presently disclosed subject matter provides a method of promoting a treatment for a subject in need of therapy for a Mendelian disorder of the epigenetic machinery, wherein the treatment comprises a ketogenic composition in an amount sufficient to produce a physiologically acceptable ketosis when administered to a subject in need of therapy for a Mendelian disorder of the epigenetic machinery. In other aspects, the presently disclosed subject matter provides a method of instructing a subject in need of therapy for a Mendelian disorder of the epigenetic machinery by providing instructions to receive a treatment comprising a ketogenic composition in an amount sufficient to produce a physiologically acceptable ketosis in the subject.

In some aspects, the Mendelian disorder of the epigenetic machinery is Kabuki syndrome (KS). In some aspects, the ketogenic composition comprises a ketogenic diet. In some aspects, the ketogenic diet comprises a diet in which about 2% to about 15% by weight of its caloric content is carbohydrates, about 60% to about 90% by weight of its caloric content is fat, and about 8% or less by weight of its caloric content is protein.

In some aspects, the ketogenic composition comprises a nutritionally balanced ketogenic diet. In some aspects, the nutritionally balanced ketogenic diet comprises a diet in which about 2% to about 15% by weight of its caloric content is carbohydrates, about 60% to about 90% by weight of its caloric content is fat, and about 8% to about 30% by weight of its caloric content is protein. In some aspects, the nutritionally balanced ketogenic diet comprises a 4:1 ratio of caloric fat content to caloric protein content.

In some aspects, the ketogenic composition comprises a ready-to-drink beverage, powdered beverage formulation, nutritional or dietary supplement selected from the group consisting of gelatin capsule or tablet, suspension, parenteral solution, or a food product formulated for human consumption. In some aspects, the ketogenic composition comprises at least one ketogenic compound selected from the group consisting of: i) a ketogenic amino acid selected from the group consisting of isoleucine, leucine, tryptophan, lysine, phenylalanine, tyrosine, aspartate β-semialdehyde, β-aspartylphosphate, saccharopine, α-aminoadipate δ-semialdehyde, and α-aminoadipate; ii) an immediate precursor of a ketogenic amino acid selected from the group consisting of α-ketoglutarate, indole, α-ketobutarate L-histadinol, phenylpyruvate, 4-hydroxyphenylpyruvate, methyltetrahydrofolate, α-keto-β-methylvalerate, and α-ketoisovalerate; iii) an amino acid increasing molecule selected from the group consisting of a glutamate dehydrogenase, a valine aminotransferase, an arginosuccinate lyase, a tyrosine transaminase, an aromatic amino acid transaminase, a tryptophan synthase, and a histidinol dehydrogenase; iv) a medium chain triglyceride; v) a short chain fatty acid; and vi) combinations thereof.

In some aspects, the ketogenic composition comprises at least one agent that promotes open chromatin states at one or more target genes in the subject. In some aspects, at least one agent decreases the level and/or activity of a histone deacetylase protein in the subject. In some aspects, the histone deacetylase protein is selected from the group consisting of histone deacetylase 1 (HDAC1), histone deacetylase 2 (HDAC2), histone deacetylase 3 (HDAC3), histone deacetylase 4 (HDAC4), histone deacetylase 5 (HDAC5), histone deacetylase 6 (HDAC6), histone deacetylase 7 (HDAC7), histone deacetylase 8 (HDAC8), histone deacetylase 9a (HDAC9a), histone deacetylase 9b (HDAC9b), histone deaceytlase 9c (HDAC9c), histone deaceytlase 10 (HDAC10), histone deacetylase 11 (HDAC11), SIRT1, SIRT2, SIRT3, SIRT4, SIRT5, SIRT6, and SIRT7. In other aspects, the ketogenic composition comprises at least one agent that decrease the level and/or activity of a NAD+ dependent deacetylase protein. In some aspects, the NAD+ dependent deacetylase protein is selected from the group consisting of SIRT1, SIRT2, SIRT3, SIRT4, SIRT5, SIRT6, and SIRT7.

In some aspects, the agent increases the level of H3Kme4 in the subject. In some aspects, at least one agent decreases deacetylation of and/or increases trimethylation of lysine 4 of histone 3 in the subject. In some aspects, at least one agent increases histone acetylation of H3 and H4 tails, such as H4K5, H4K8, H4K12, and H4k16. In some aspects, at least one agent is selected from the group consisting of: i) D-β-hydroxybutyrate; ii) a salt of D-β-hydroxybutyrate; iii) a metabolic precursor of D-β-hydroxybutyrate; iv) an ester or polyester of D-β-hydroxybutyrate; and v) combinations thereof.

In some aspects, at least one agent is selected from the group consisting of i) (S)—N-hydroxy-4-(3-methyl-2-phenylbutanamido)benzamide (AR-42); ii) 2-Propylpentanoic acid (valproic acid); iii) N'-hydroxy-N-phenyl-octanediamide (vorinostat); and iv) 5H-dibenz[b,f]azepine-5-carboxamide (carbamazepine).

In some aspects, the ketogenic composition is administered at least once daily. In some aspects, the ketogenic composition is administered as part of a daily treatment regimen that lasts for at least two weeks. In some aspects, the ketogenic composition is administered as part of a daily treatment regimen that lasts for at least 6 months. In some aspects, the physiologically acceptable ketosis produced is such that the total concentration of β-hydroxybutyrate in the blood of the subject is raised to between 0.5 and 10 mM. In some aspects, the total concentration of β-hydroxybutyrate in the blood is raised to between 1 and 6 mM. In some aspects, a urinary excretion level of β-hydroxybutyrate is from about 5 to about 200 mg/dL. In some aspects, the subject is a human. In some aspects, the subject has, or is suspected of having, a redox imbalance. In some aspects, the method comprises selecting a subject for treatment with a therapy for a Mendelian disorder of the epigenetic machinery by determining whether the subject has a redox imbalance and/or by determining whether the subject has an imbalance between open and closed chromatin states at one or more target genes.

In some aspects, the presently disclosed subject matter provides a method of selecting a subject for treatment with a therapy for a Mendelian disorder of the epigenetic machinery, the method comprising: (a) obtaining a biological sample from the subject; (b) assaying the biological sample for levels of: (i) acetoacetate and β-hydroxybutyrate; and/or (ii) pyruvate and lactate; (c) determining a ratio of: (i) the levels of acetoacetate in the biological sample relative to the levels β-hydroxybutyrate in the biological sample; and/or (ii) the levels of pyruvate in the biological sample to the levels of lactate in the biological sample; (d) comparing the ratios determined in (c)(i) and/or (c)(ii) to control ratios of (c)(i) and/or (c)(ii) from biological samples of normal individuals lacking a redox imbalance; and (e) selecting a subject for treatment with a therapy for a Mendelian disorder of the epigenetic machinery if the ratios determined in (c)(i) and/or (c)(ii) are decreased relative to the control ratios.

In some aspects, the control ratio of the levels of acetoacetate relative to the levels of β-hydroxybutyrate in a biological sample of a normal individual lacking a redox imbalance is about 1:1. In some aspects, the subject is selected for treatment with a therapy for a Mendelian disorder of the epigenetic machinery when the determined ratio of the levels of acetoacetate relative to the levels of β-hydroxybutyrate in the biological sample is less than or equal to about 0.9. In some aspects, the control ratio of the levels of lactate relative to the levels of pyruvate in a biological sample of a normal individual lacking a redox imbalance is about 20 to about 25. In some aspects, the subject is selected for treatment with a therapy for a Mendelian disorder of the epigenetic machinery when the determined ratio of the levels of lactate relative to the levels of pyruvate in the biological sample is more than about 30. In some aspects, the biological sample is selected from the group consisting of serum, whole blood, plasma, hemocytes, and urine. In some aspects, the step of assaying comprises an assay selected from the group consisting of a colorimetric assay, a fluorometric assay, gas chromatography-mass spectrometry, fingerstick and handheld monitor.

In some aspects, the method of selecting a subject for treatment of a Mendelian disorder of the epigenetic machinery comprises administering to the subject a ketogenic composition of the presently disclosed subject matter. In some aspects, the Mendelian disorder of the epigenetic machinery is Kabuki syndrome.

In some aspects, a method of the presently disclosed subject matter includes the step of determining whether the subject has a lysine (K)-specific methyltransferase 2D (KMT2D) gene mutation, a lysine (K)-specific demethylase 6A(KDM6A) gene mutation, or both.

In some aspects, the presently disclosed subject matter provides a kit comprising: (a) a ketogenic composition in an amount sufficient to produce a physiologically acceptable ketosis in the subject; and (b) a package insert or label with directions to treat a subject with a Mendelian disorder of the epigenetic machinery by administering the ketogenic composition. In some aspects, the amount is sufficient to produce a physiologically acceptable ketosis in the subject when the ketogenic composition is administered according to the package insert or label at a prescribed frequency and for a prescribed period of time.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
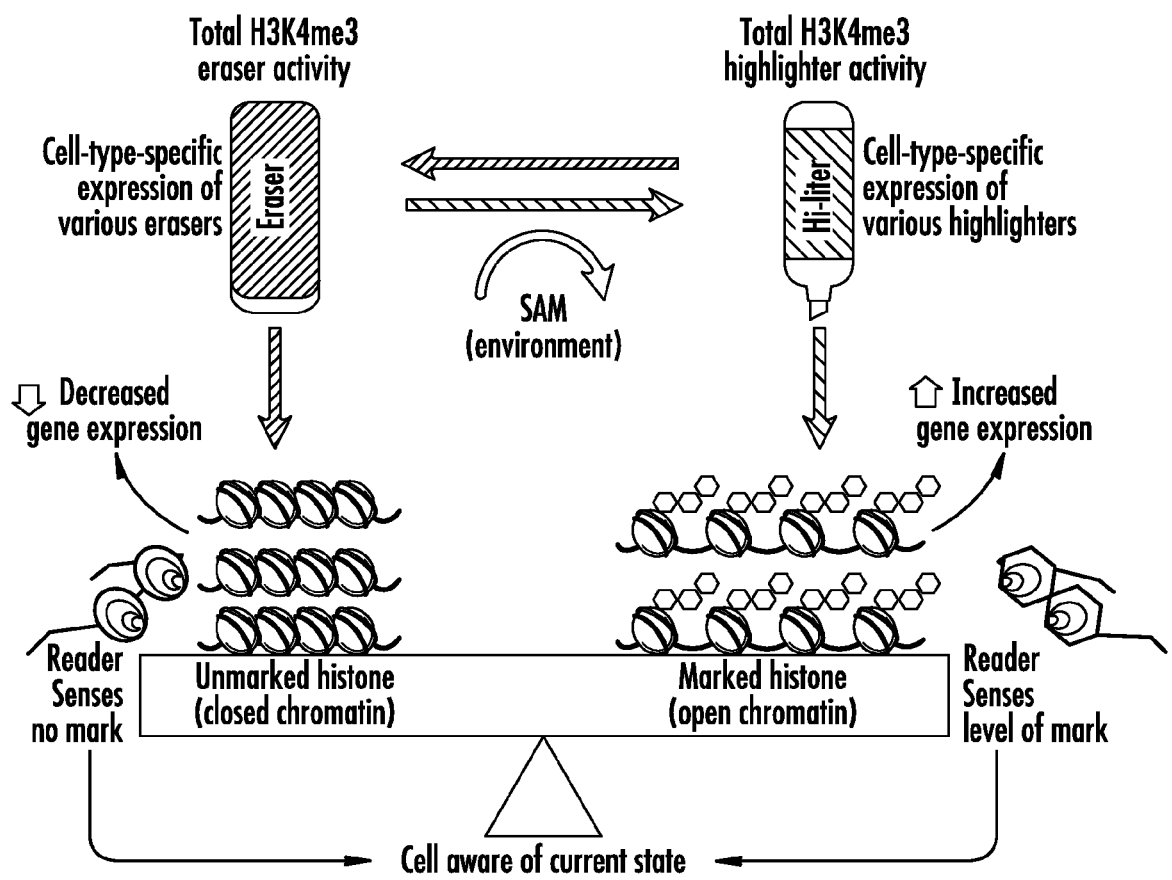
Figure 2:
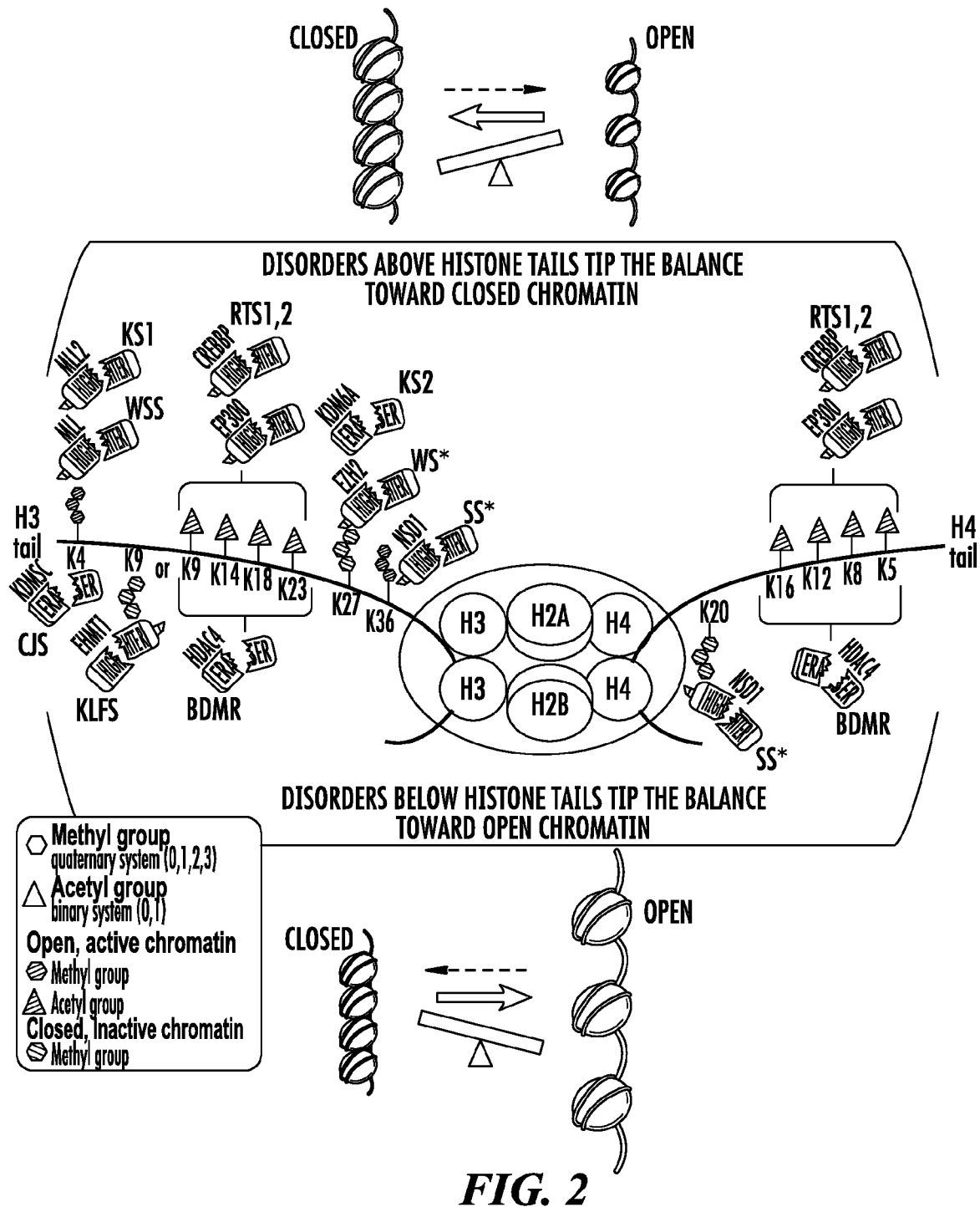
Figure 3:
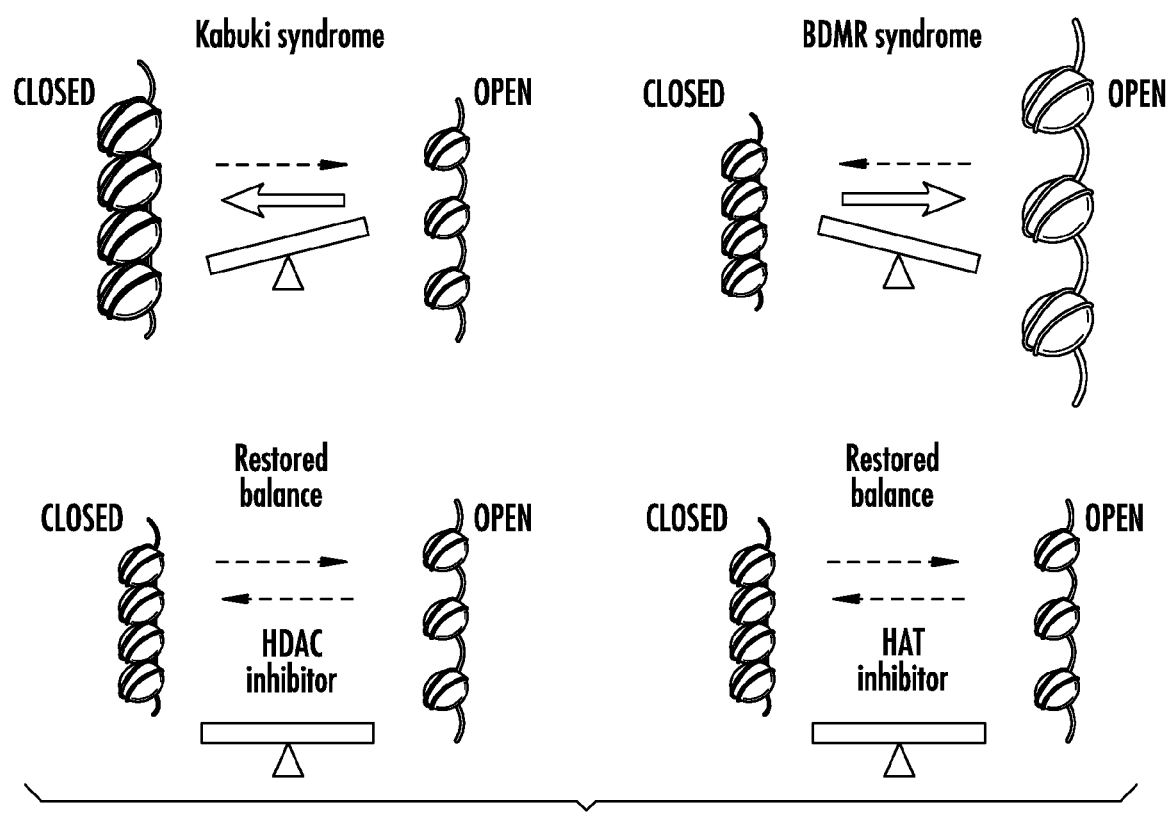
Figure 4:
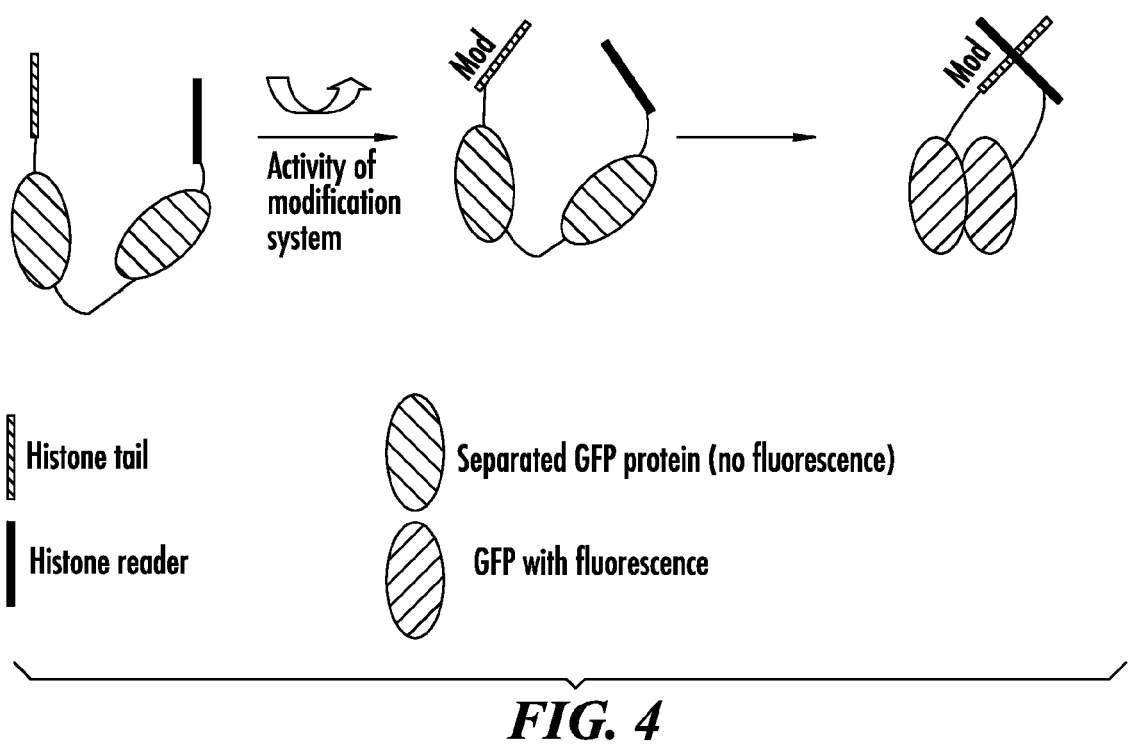
Figure 5C:
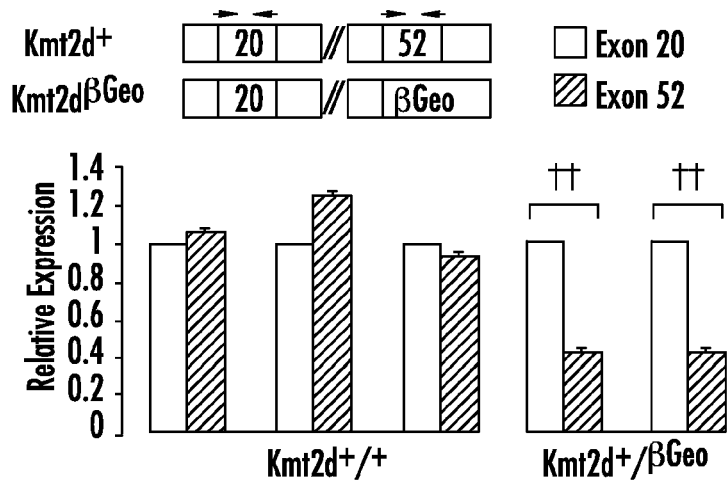
Figure 5D:
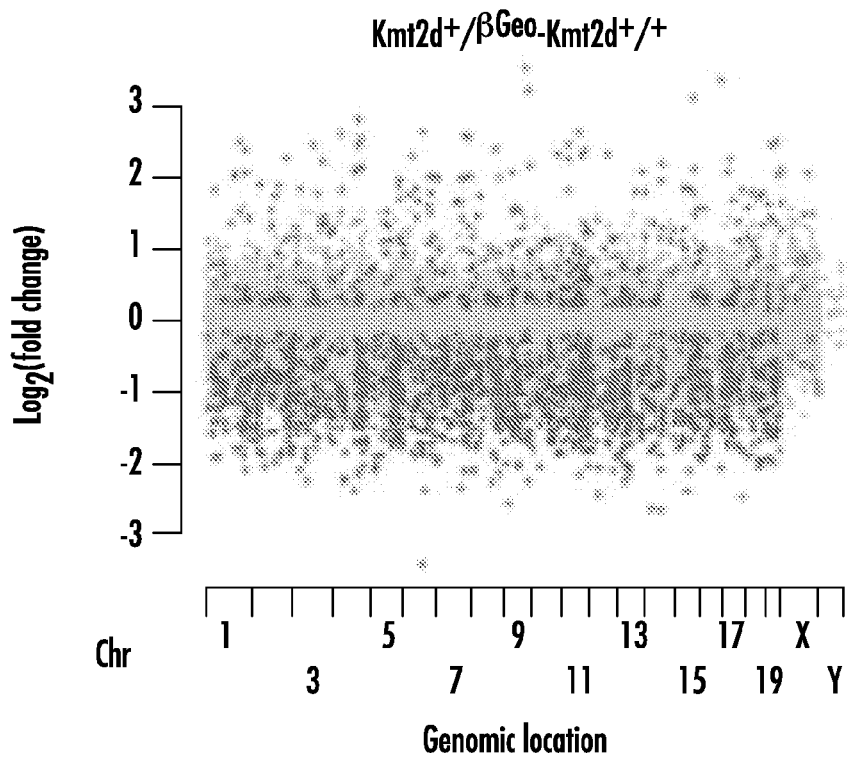
Figure 5E:
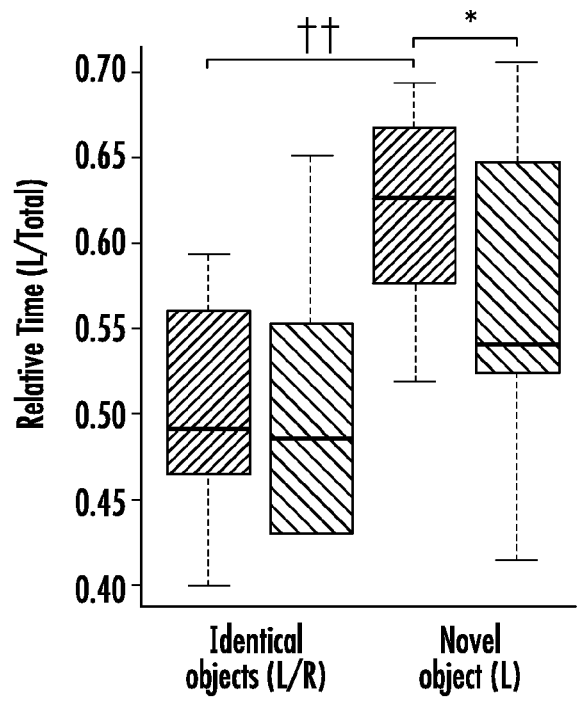
Figure 5F:
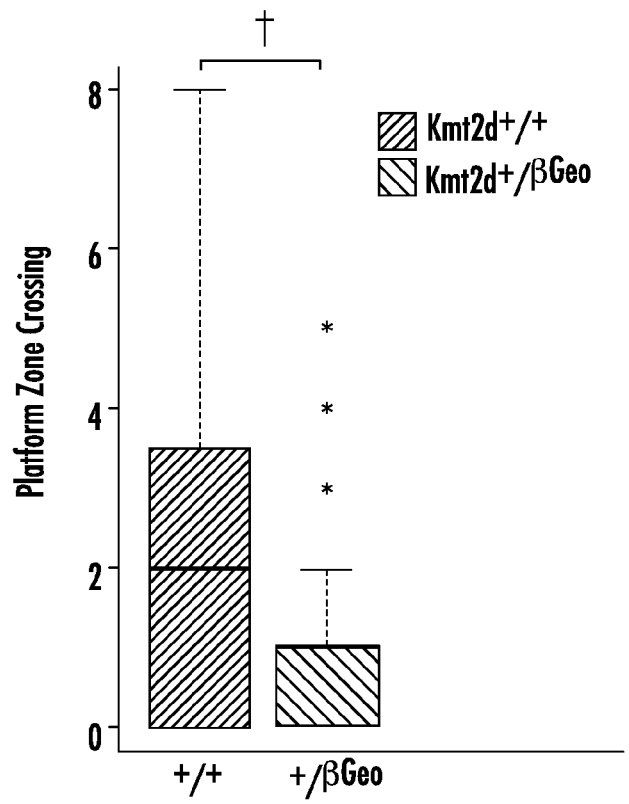
Figure 8:
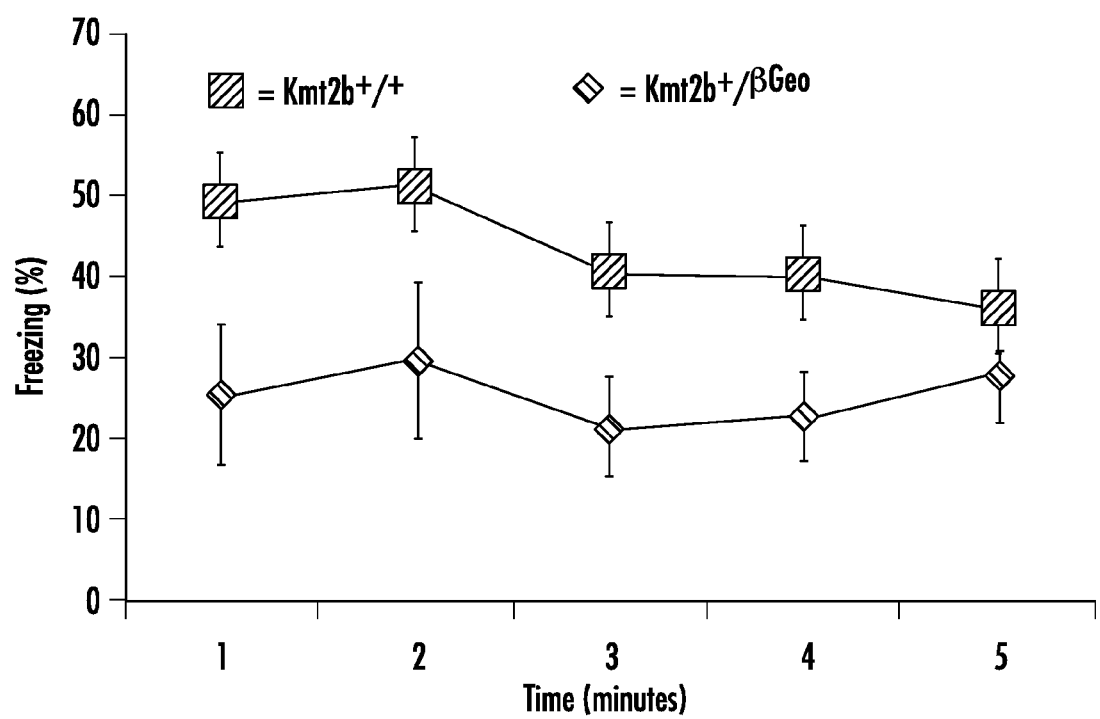
Figure 9:
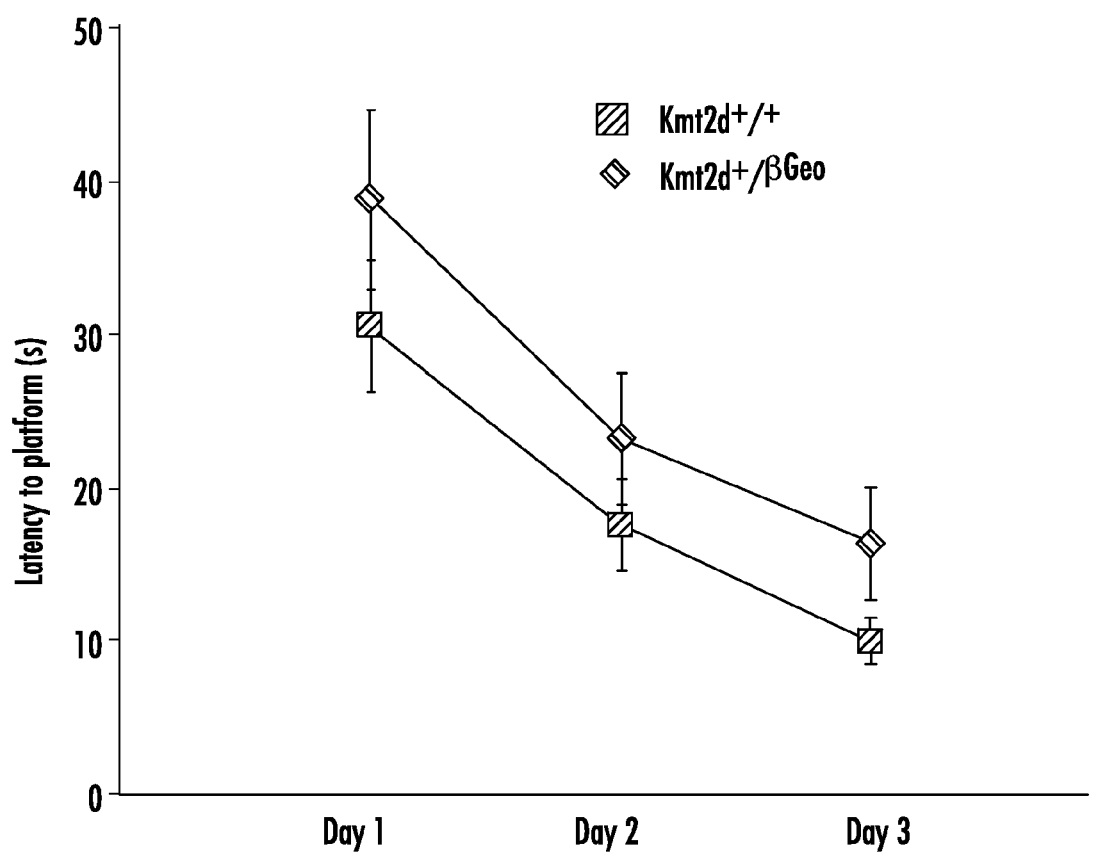
Figure 10A:
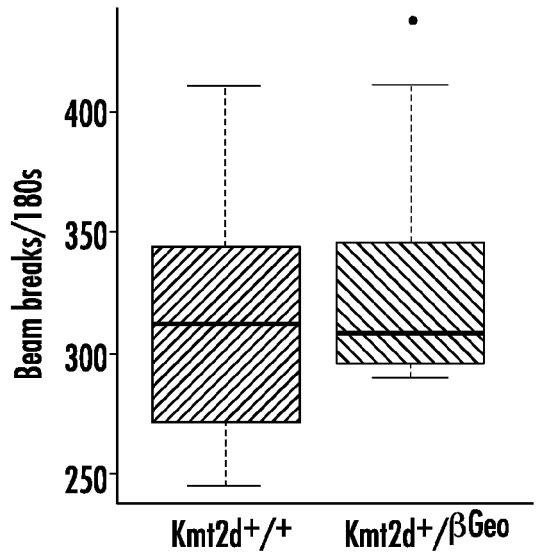
Figure 10B:
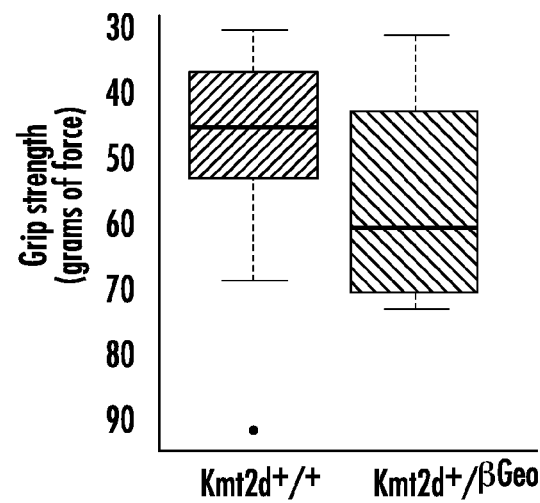
Figure 10C:
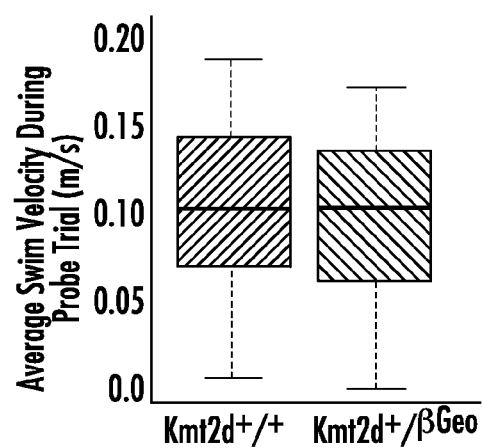
Figure 11A:
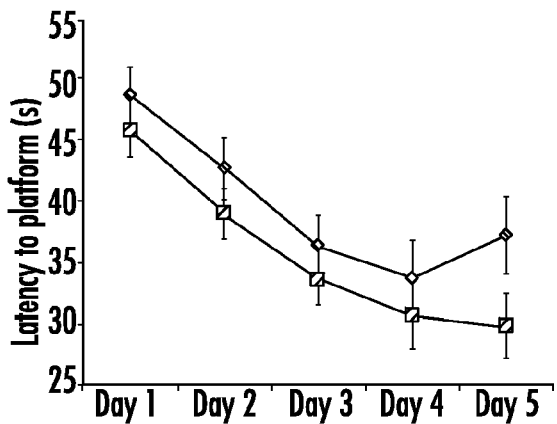
Figure 11B:
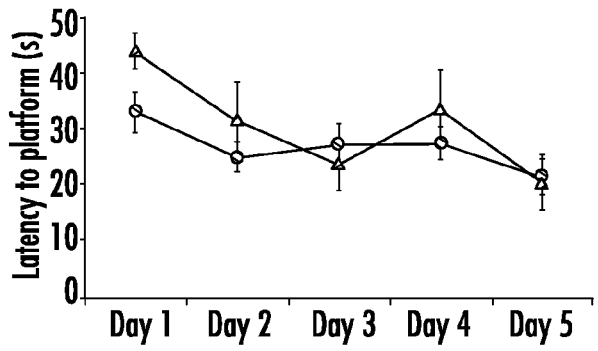
Figure 11C:
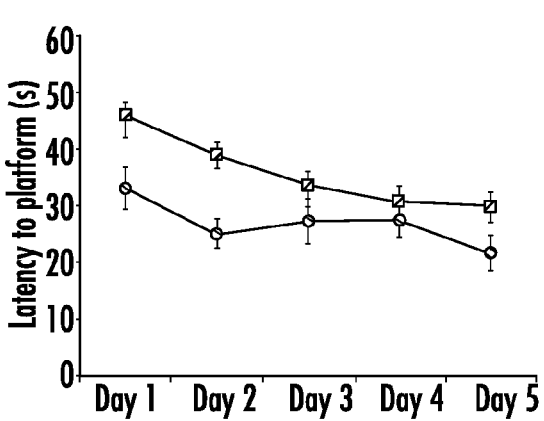
Figure 11D:
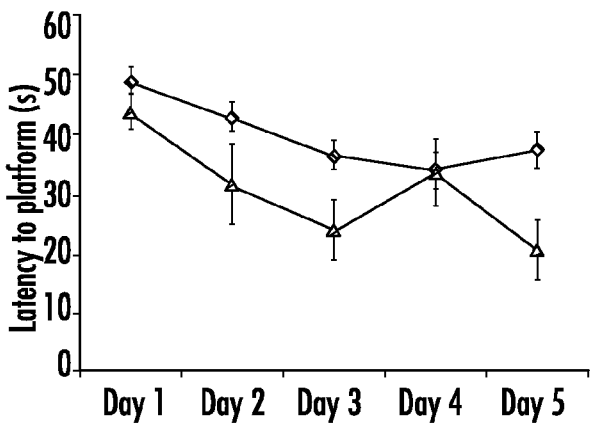
Figure 12A:
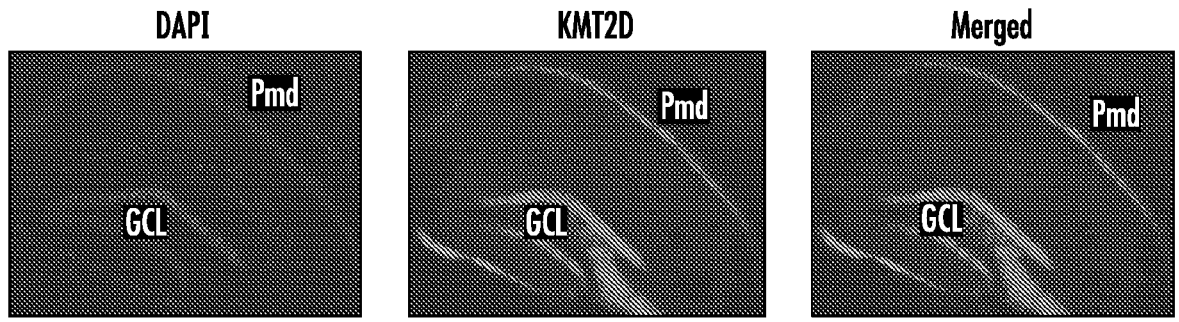
Figure 12B:
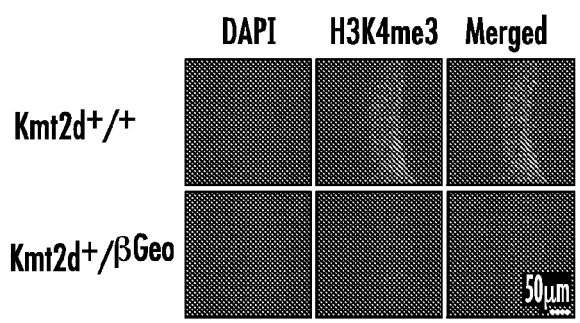
Figure 12C:
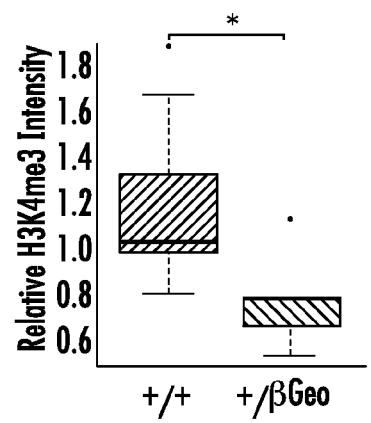
Figure 12D:
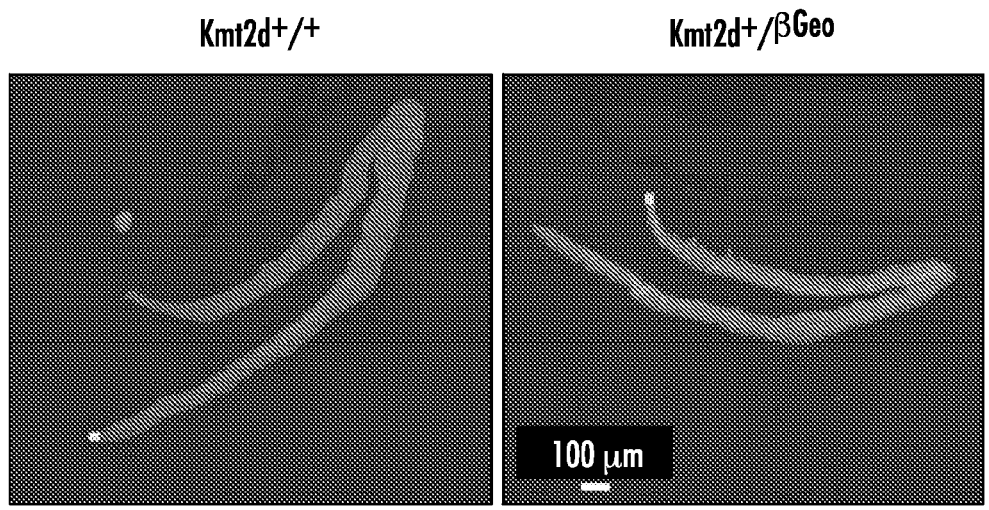
Figure 12E:
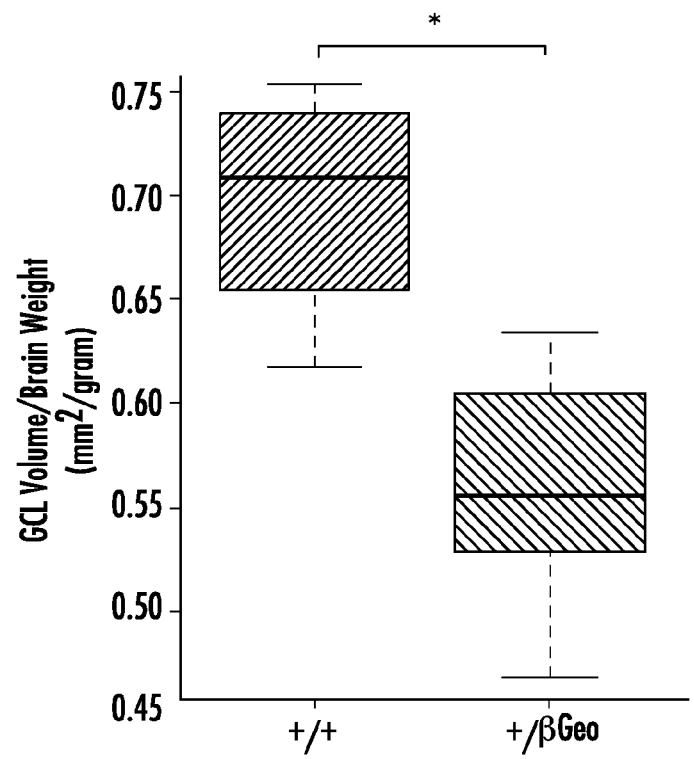
Figure 12F:
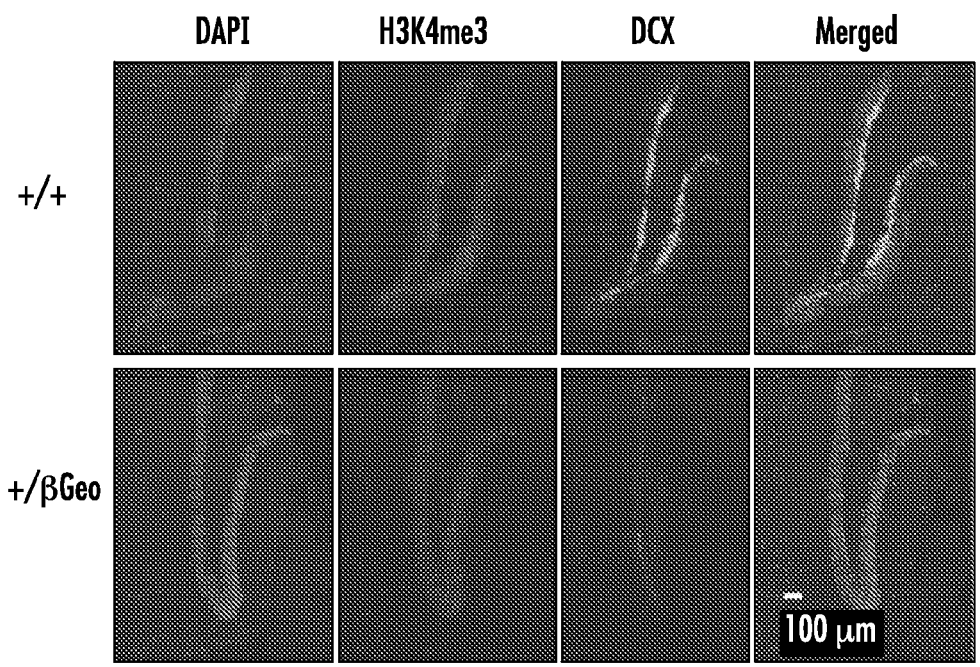
Figure 12G:
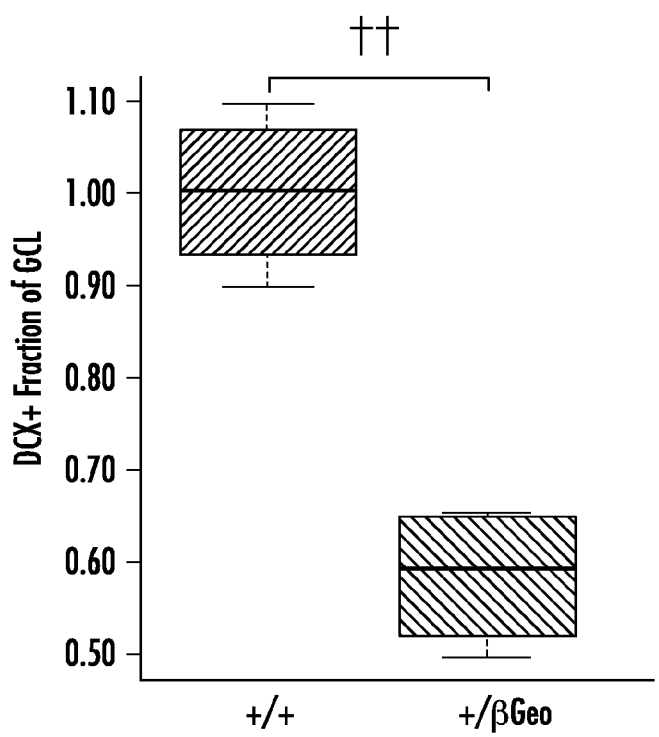
Figure 13:
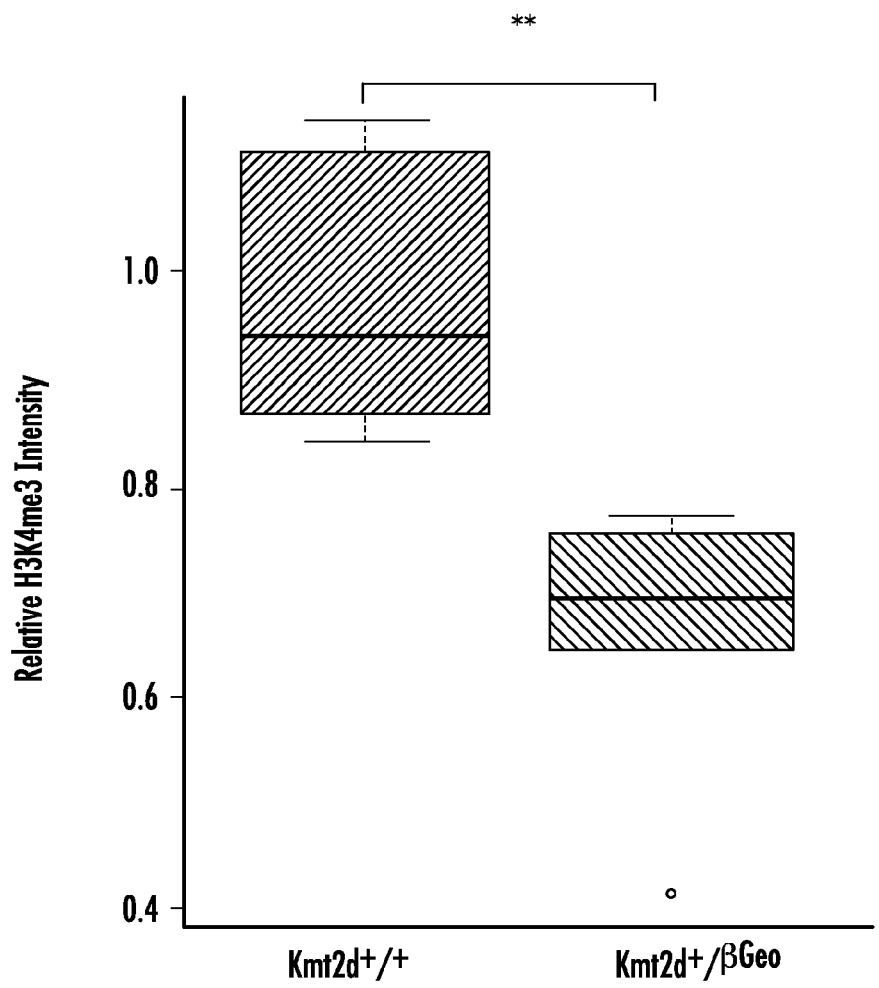
Figure 14A:
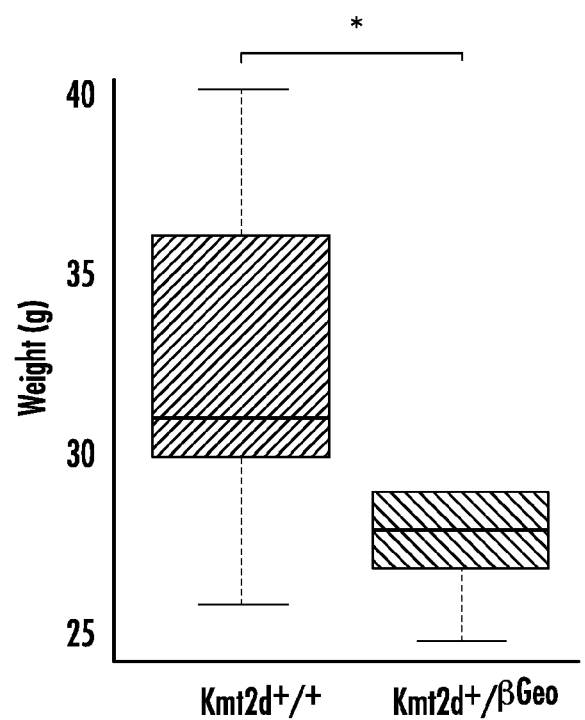
Figure 14B:
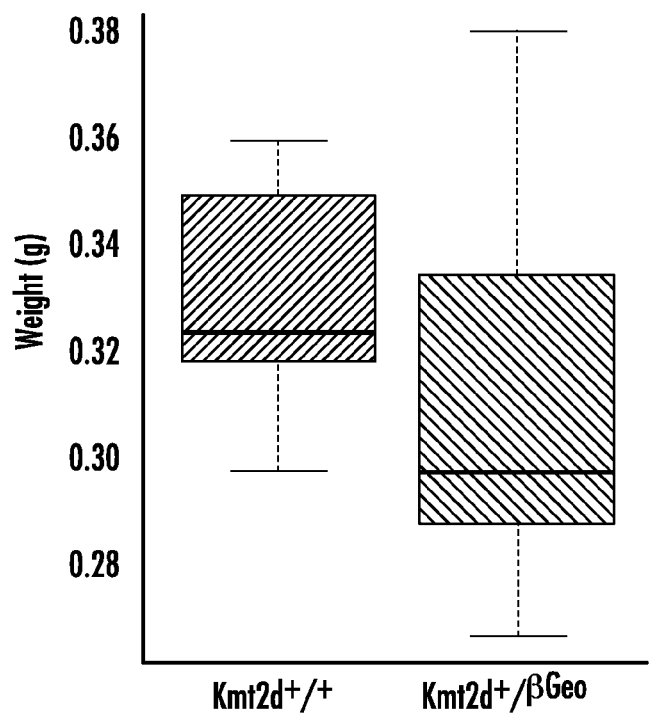
Figure 15:
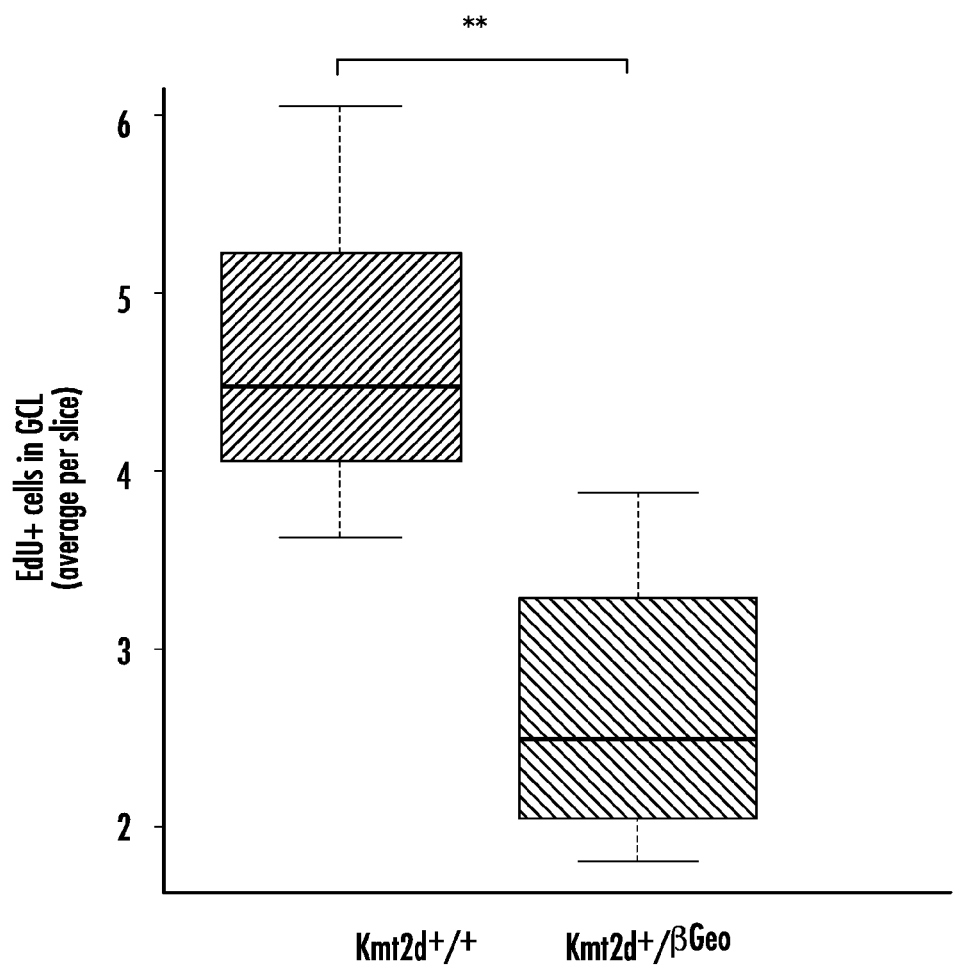
Figure 16:
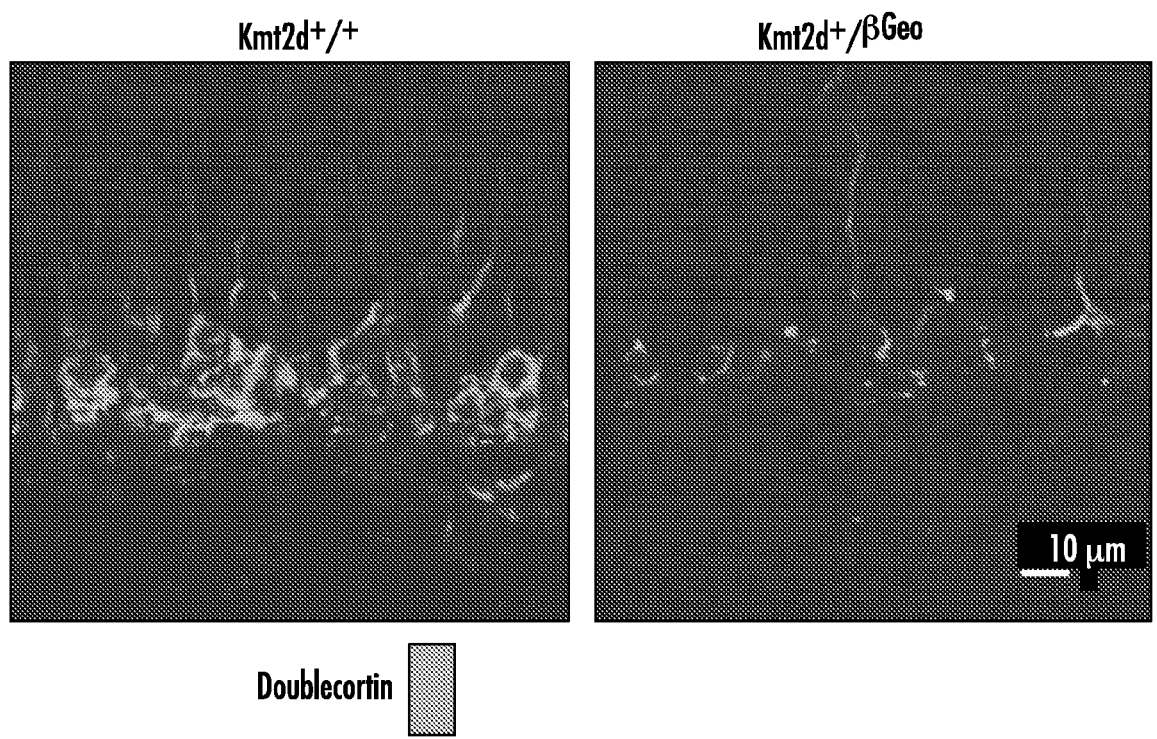
Figure 17C:
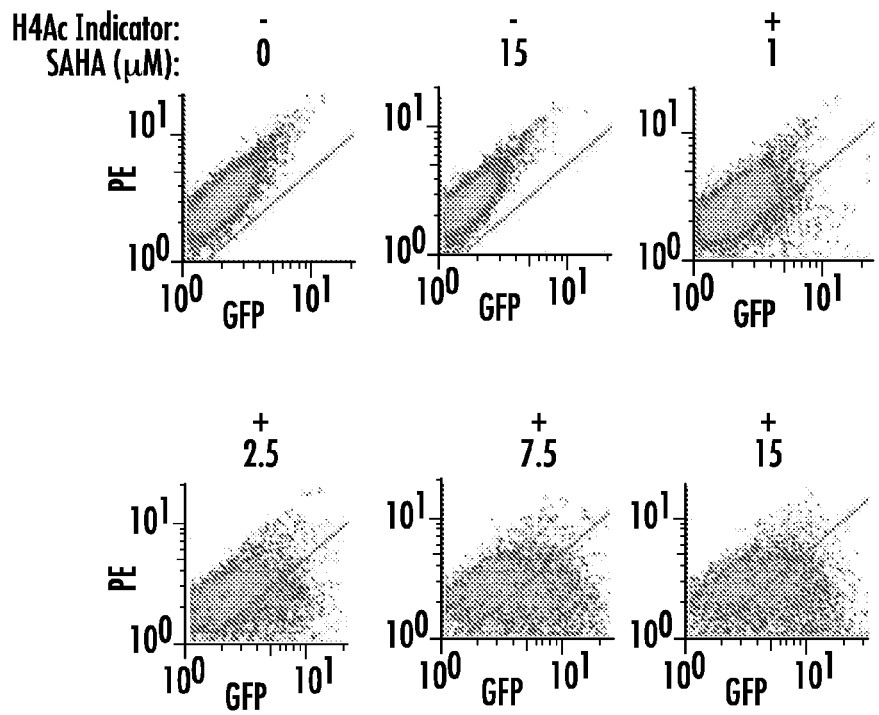
Figure 17D:
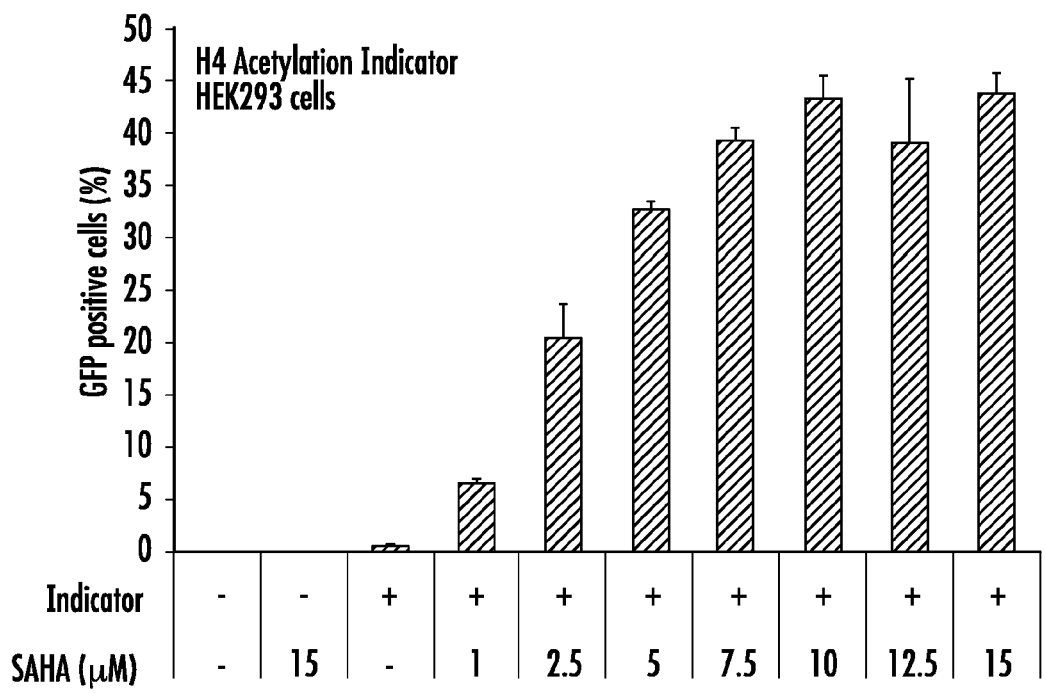
Figure 17E:
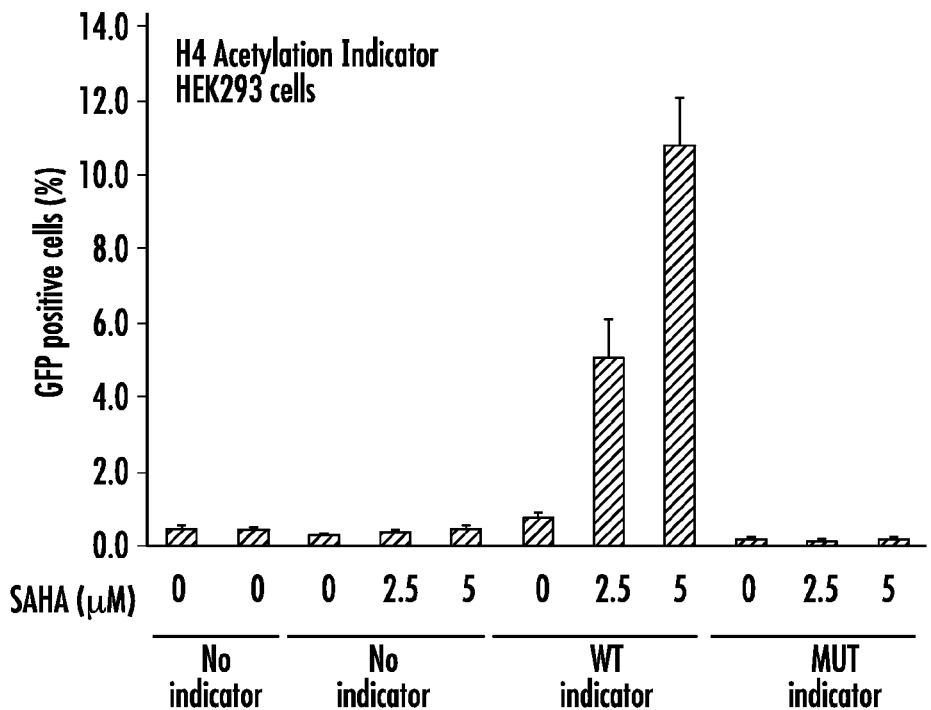
Figure 17F:
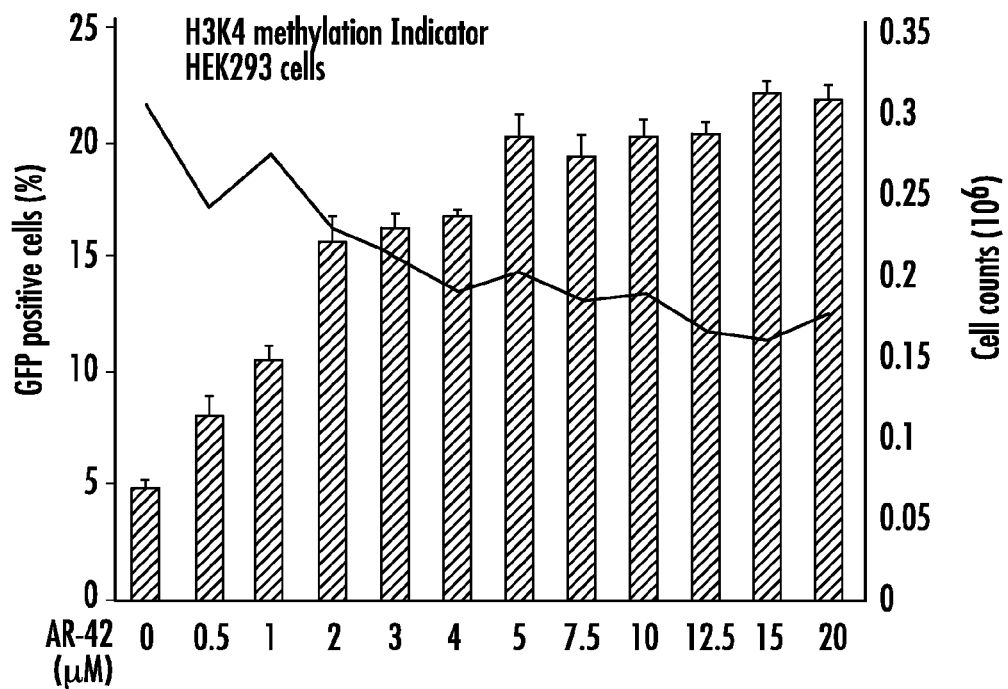
Figure 17G:
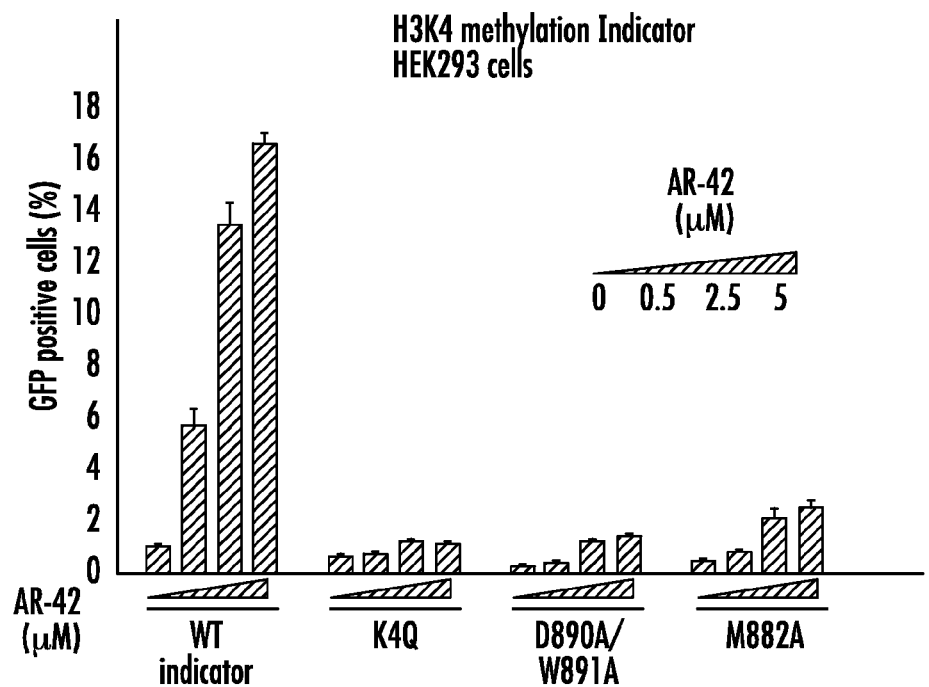
Figure 17H:
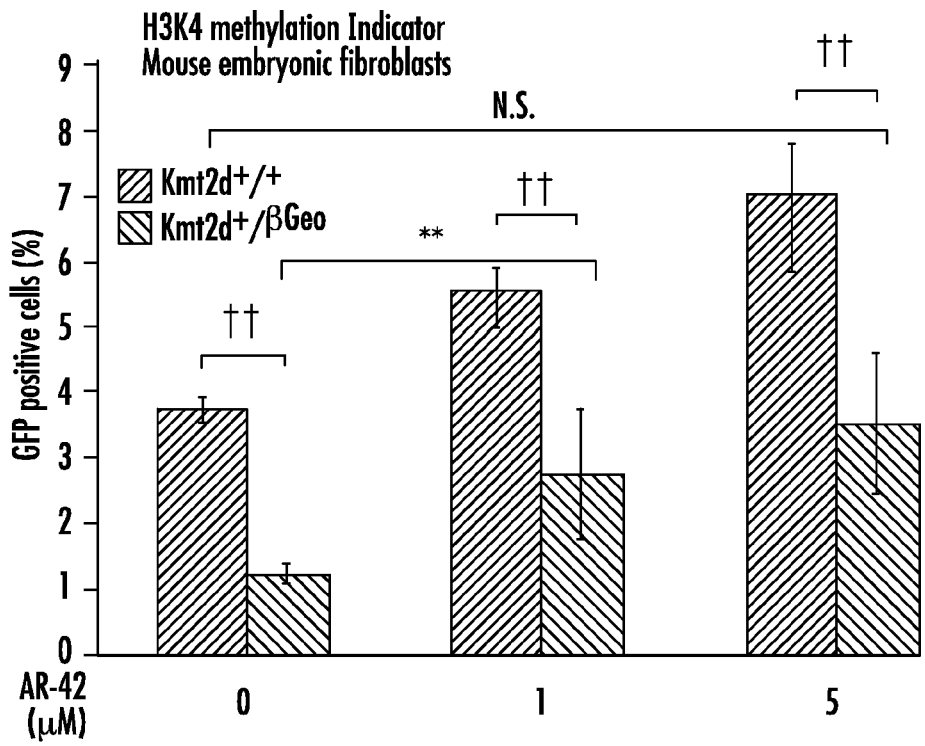
Figure 17I:
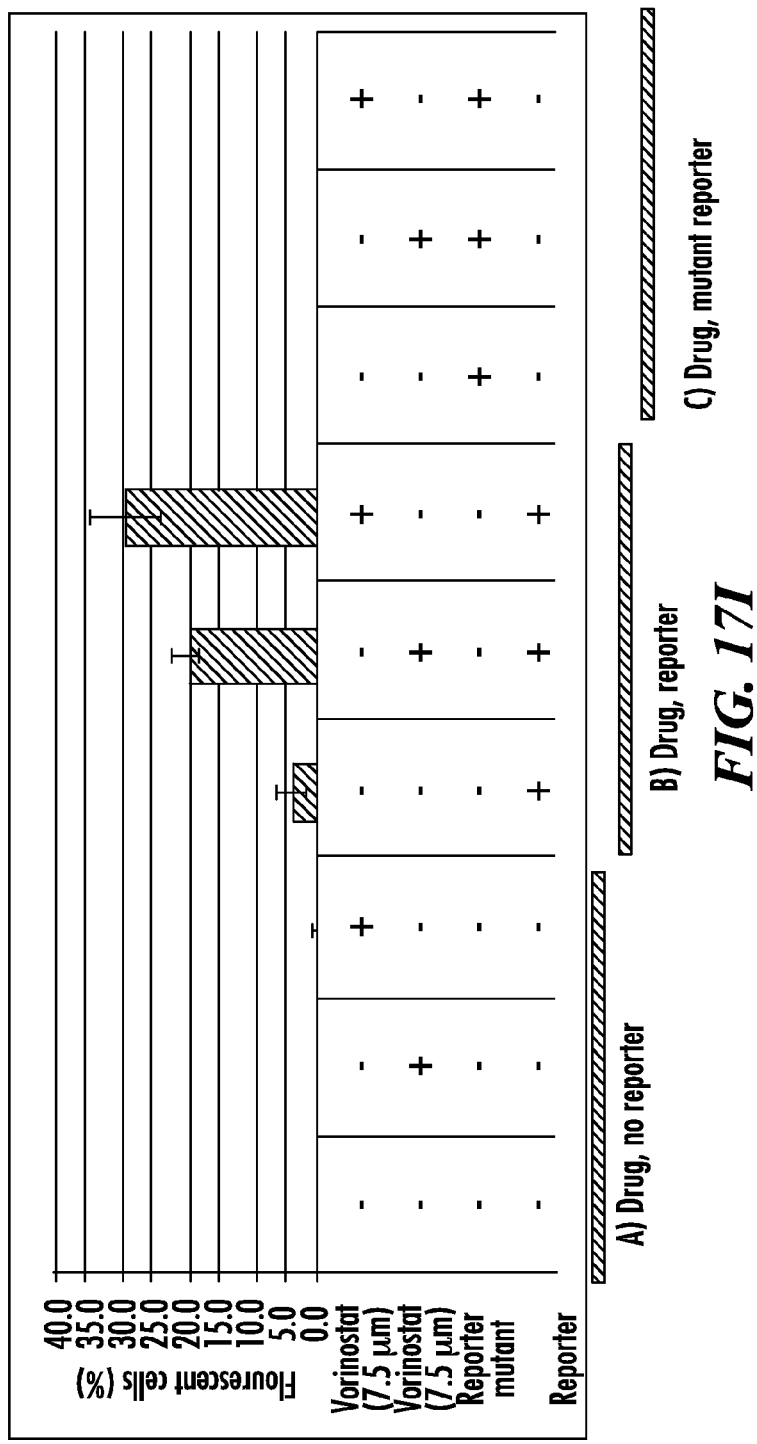
Figure 18A:
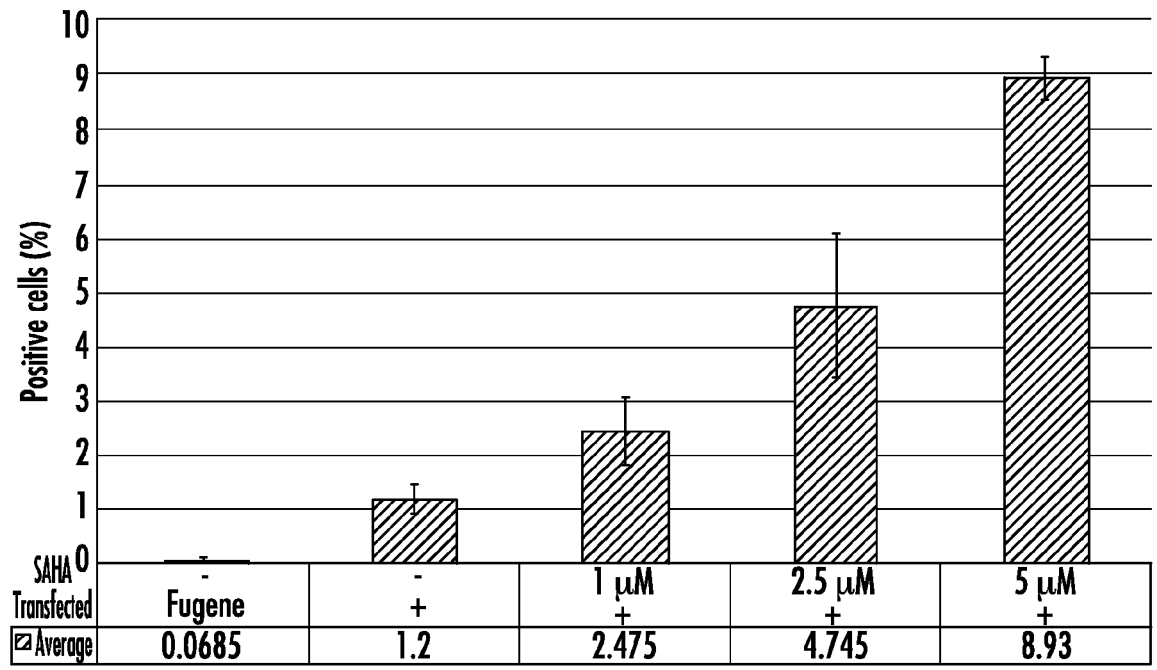
Figure 18B:
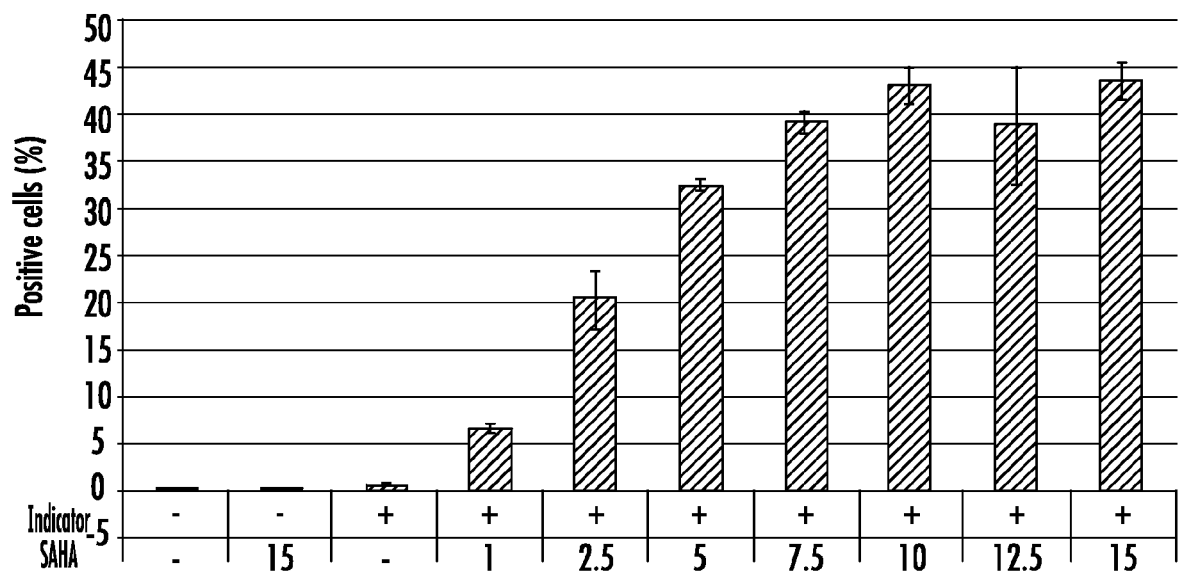
Figure 19:
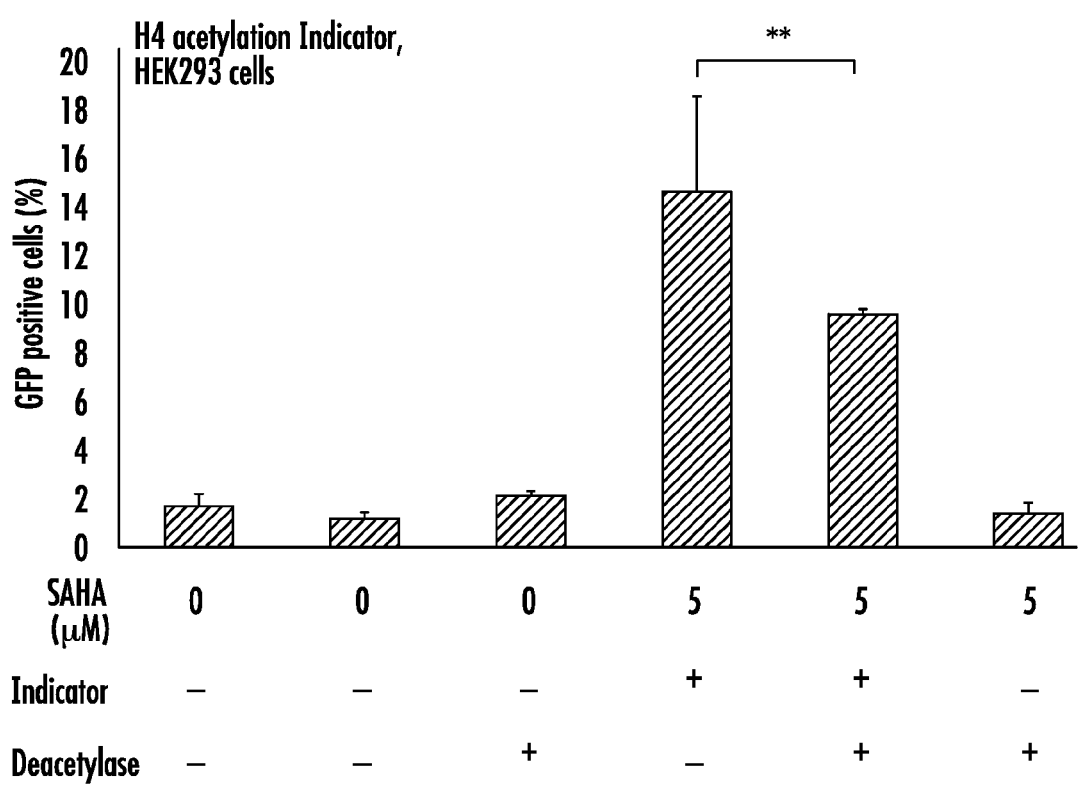
Figure 20:
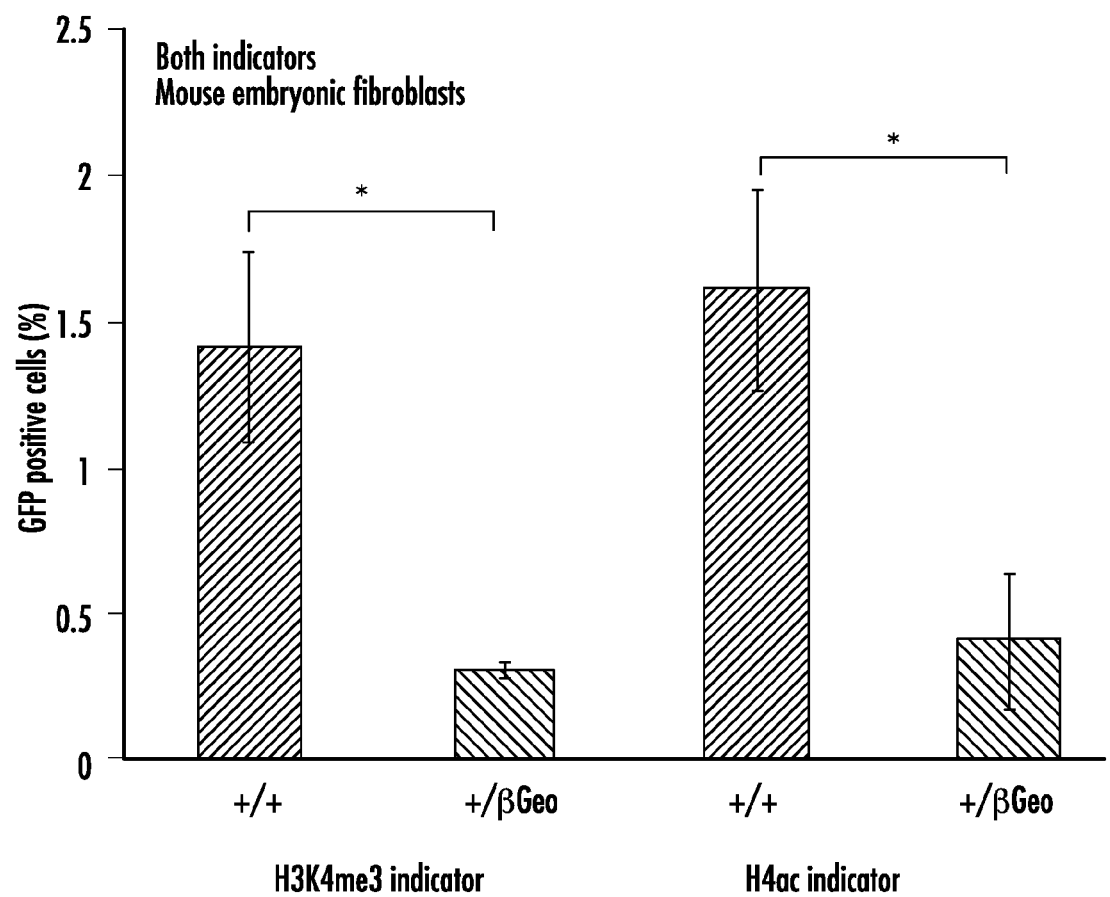
Figure 21A:
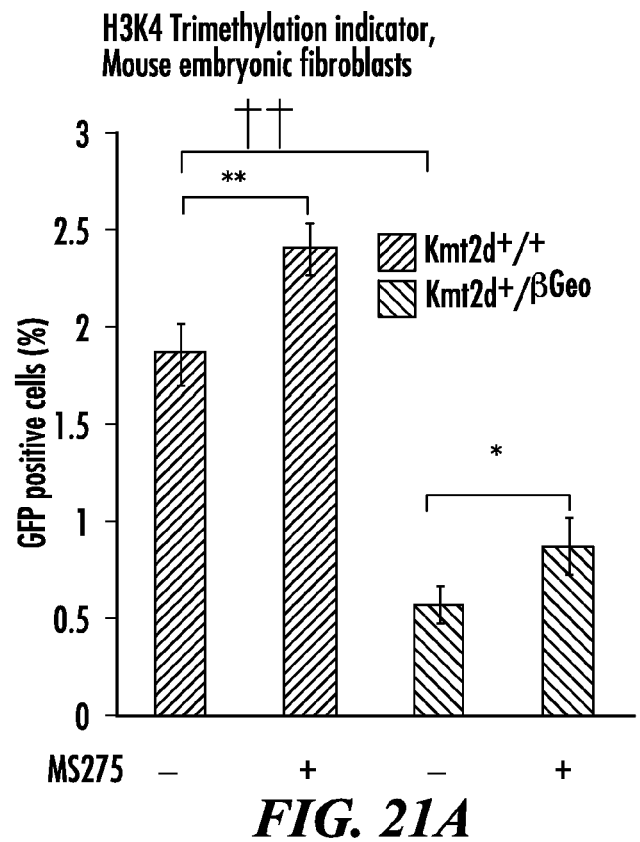
Figure 21B:
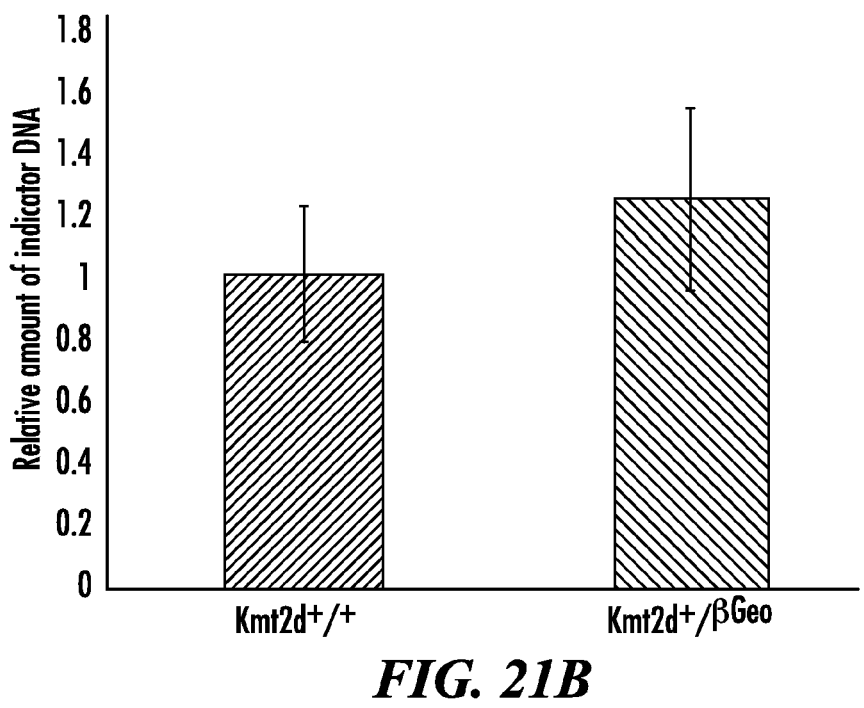
Figure 22A:
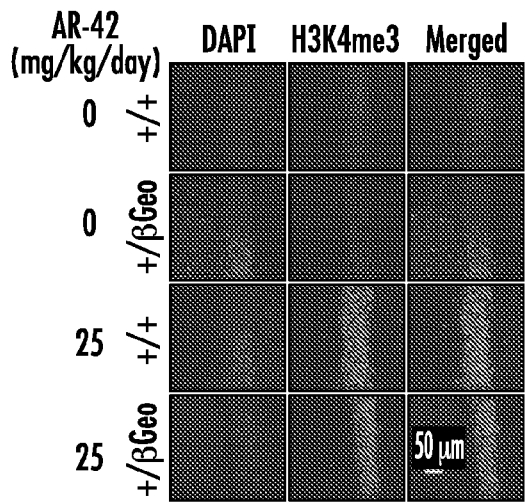
Figure 22B:
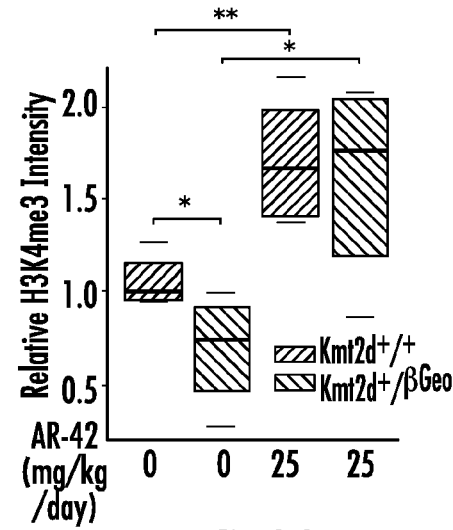
Figure 22C:
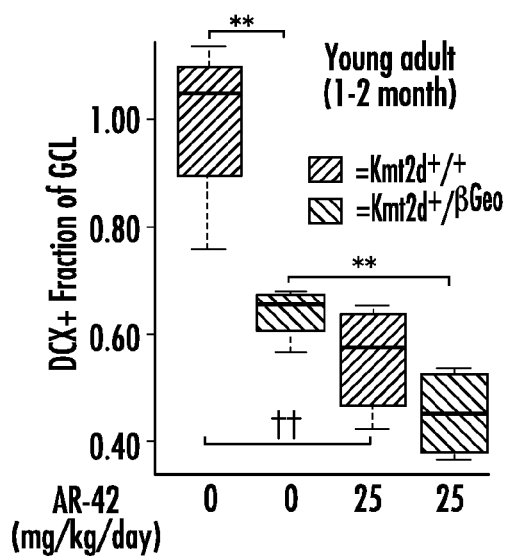
Figure 22D:
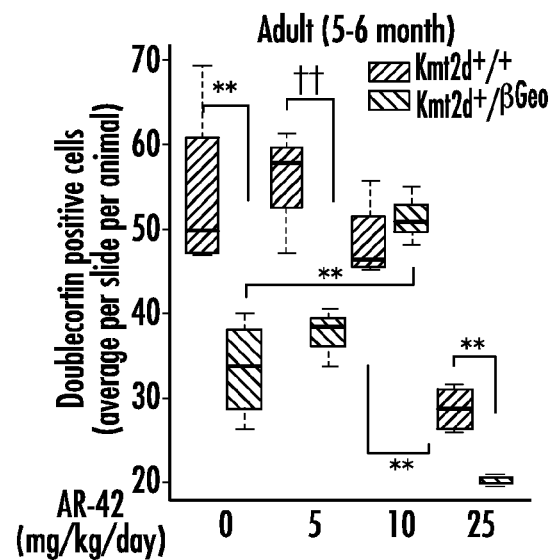
Figure 23A:
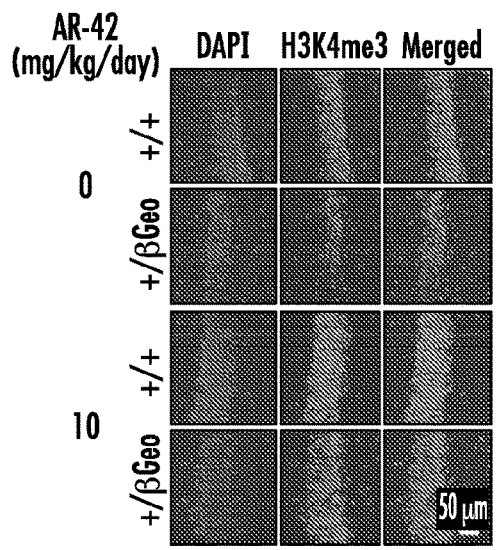
Figure 23B:
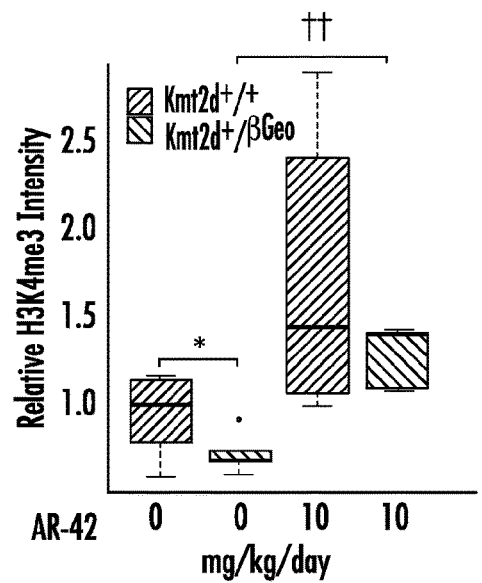
Figure 23C:
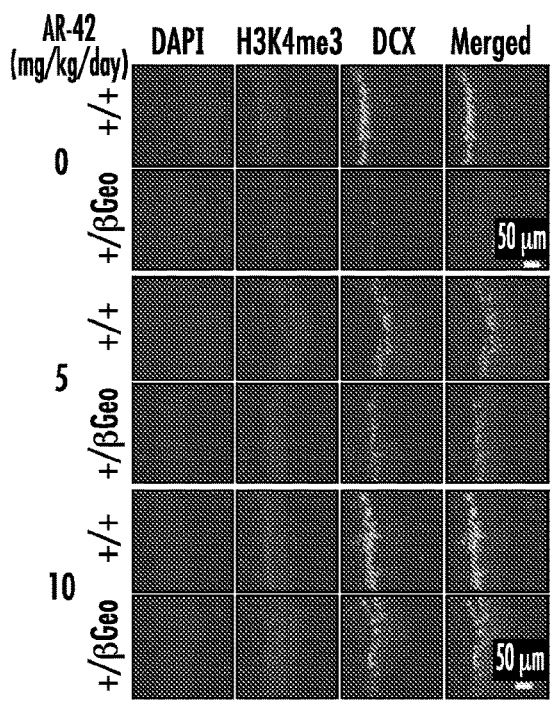
Figure 23D:
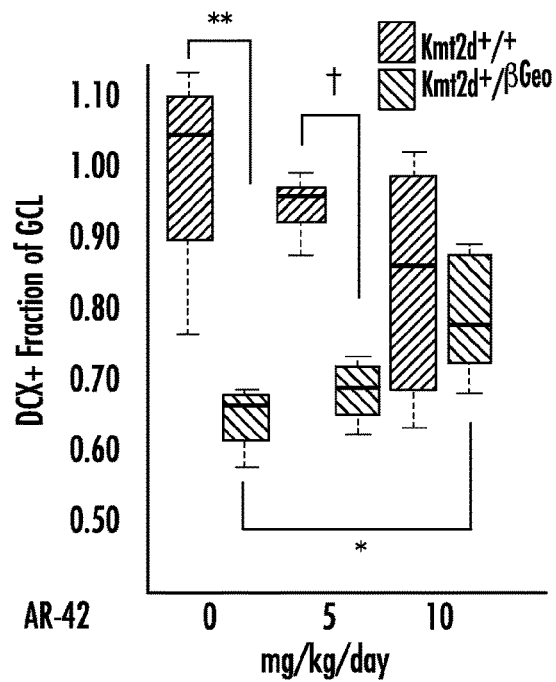
Figure 23E:
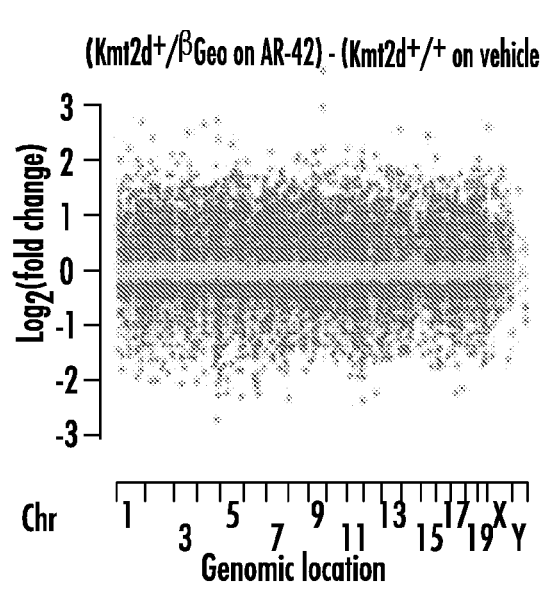
Figure 23F:
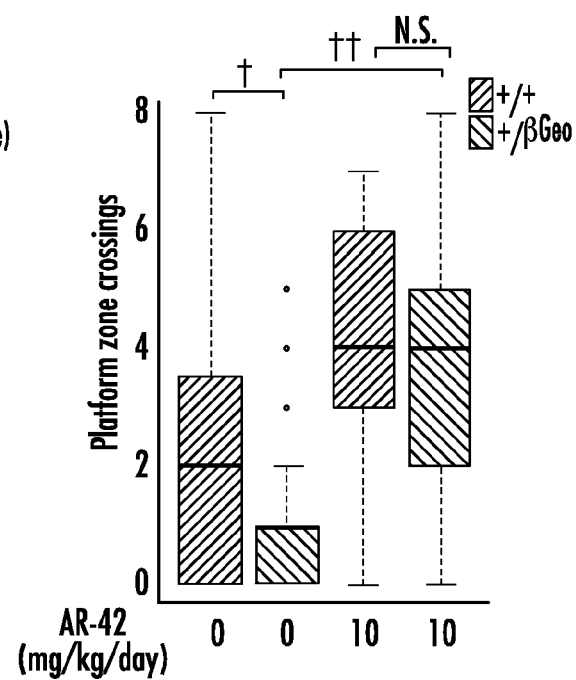
Figure 24:
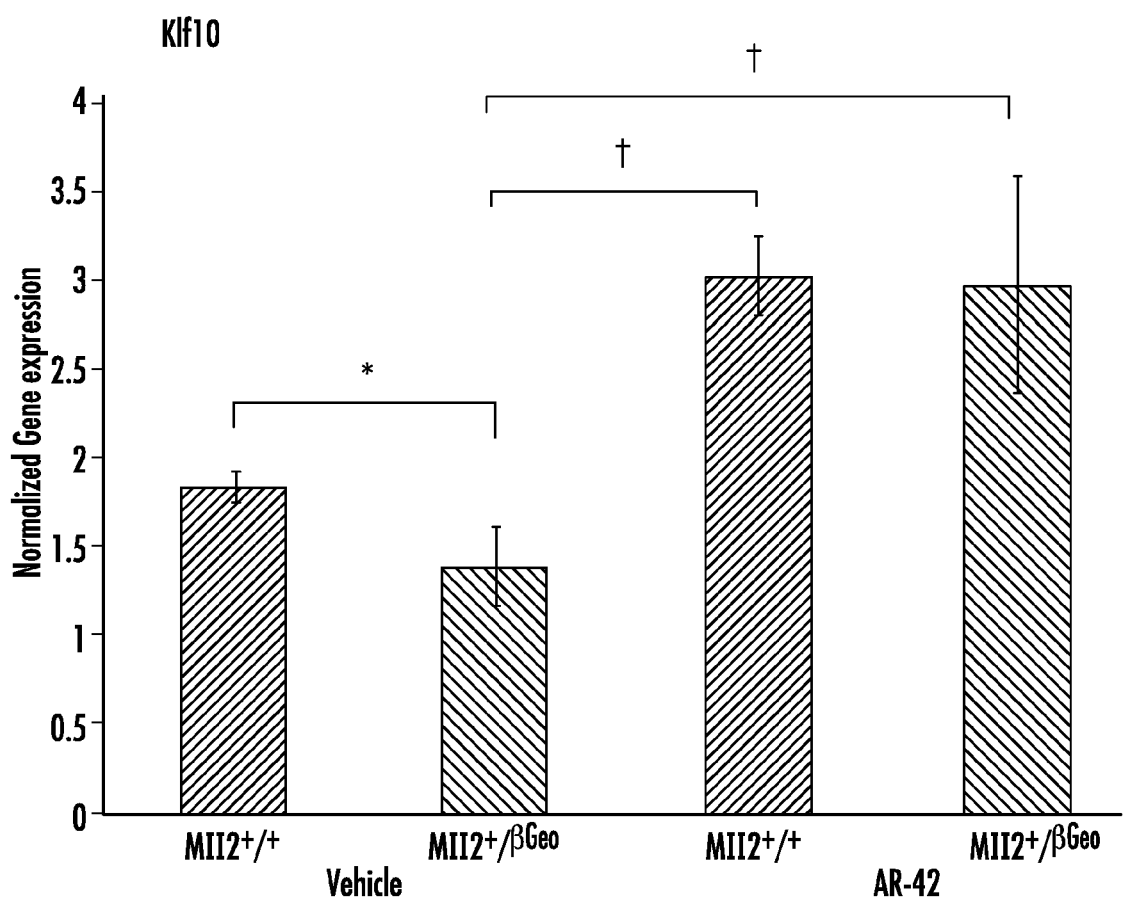
Figure 25A:
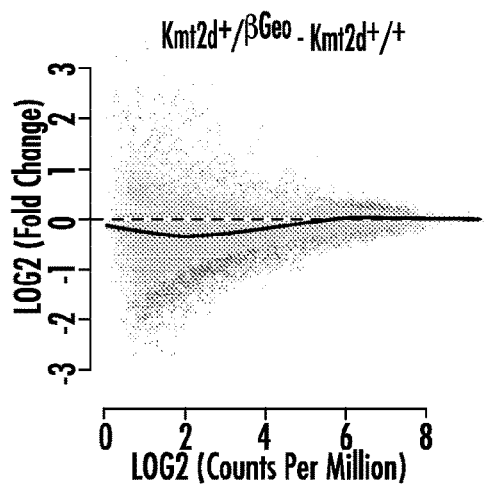
Figure 25B:
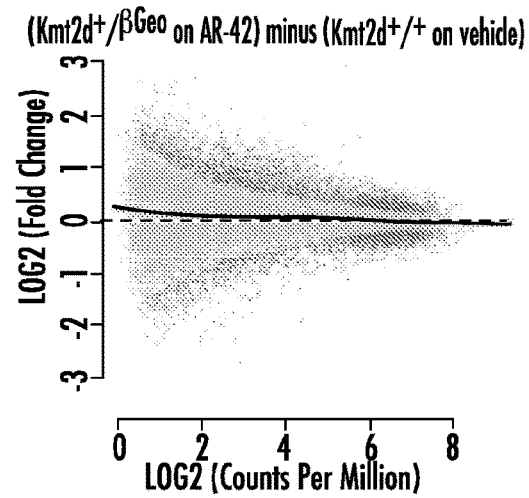
Figure 25C:
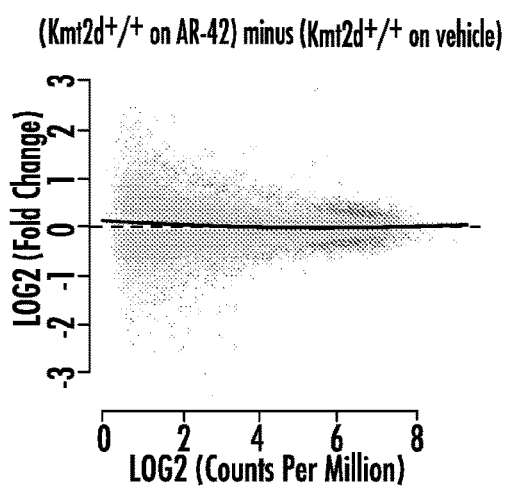
Figure 25D:
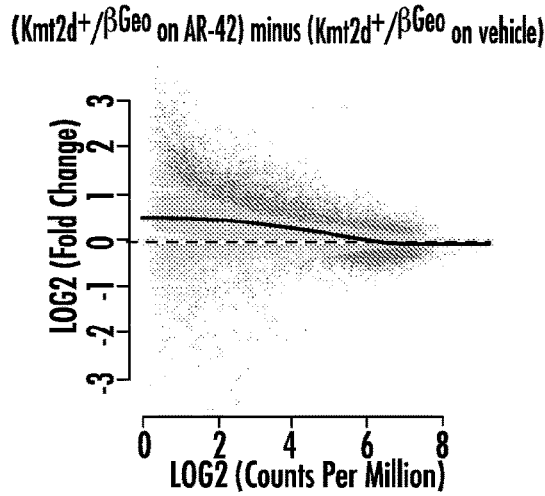
Figure 25E:
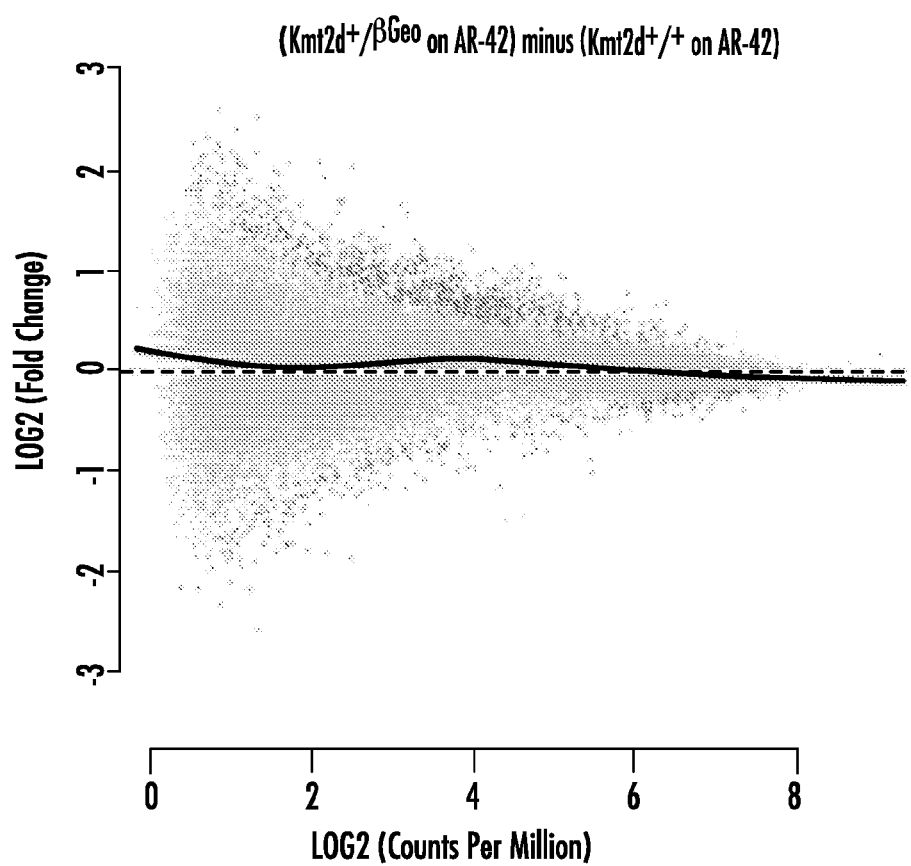
Figure 26A:
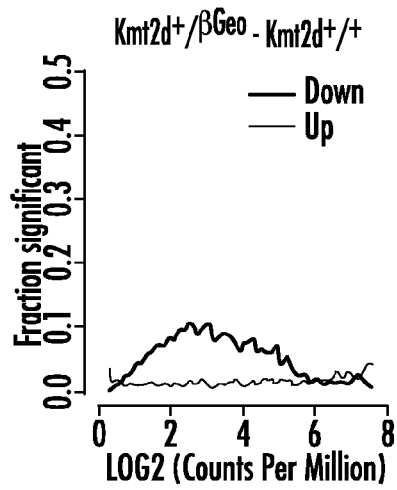
Figure 26B:
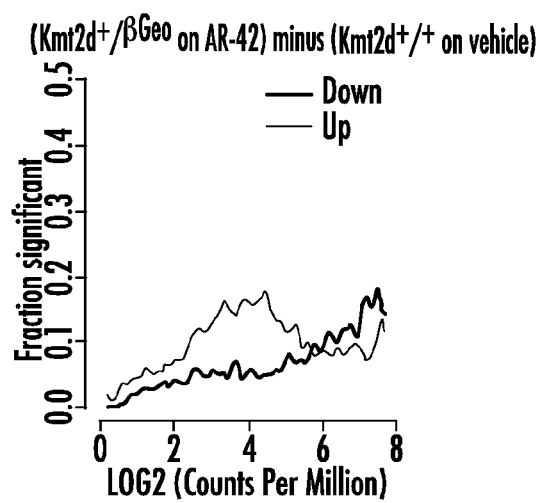
Figure 26C:
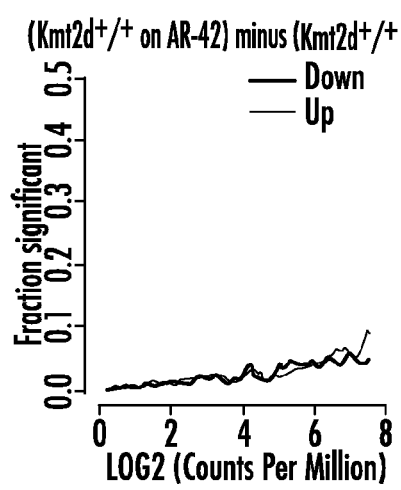
Figure 26D:
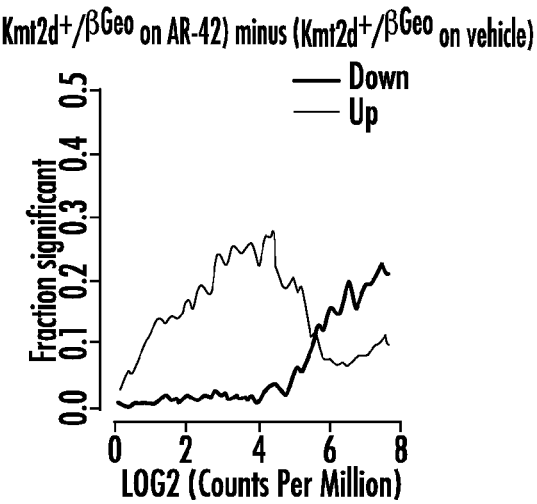
Figure 26E:
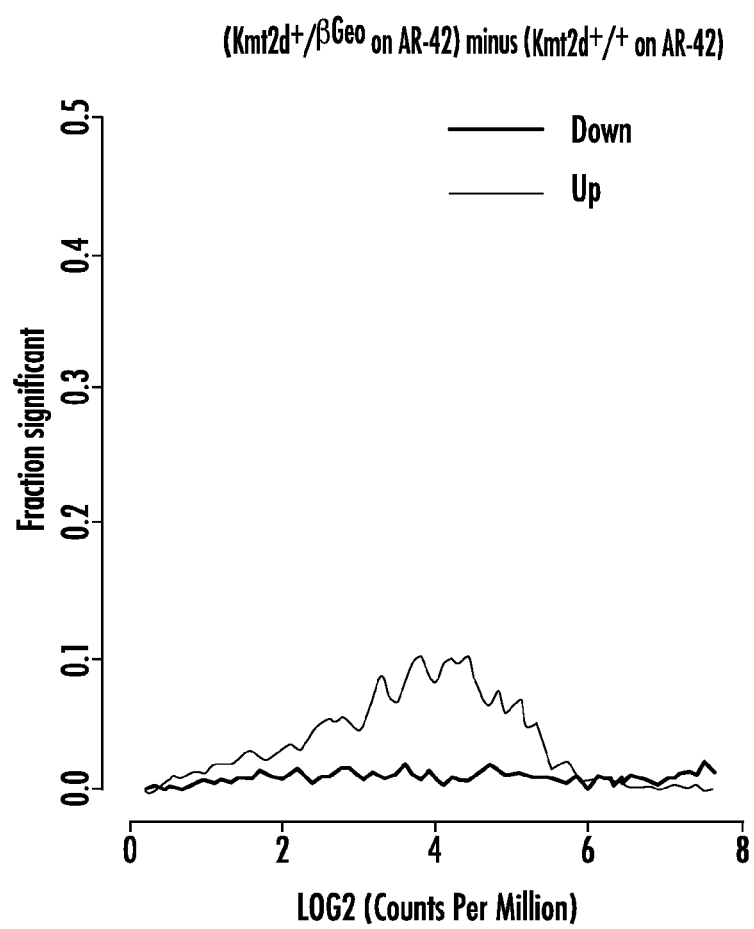
Figure 27:
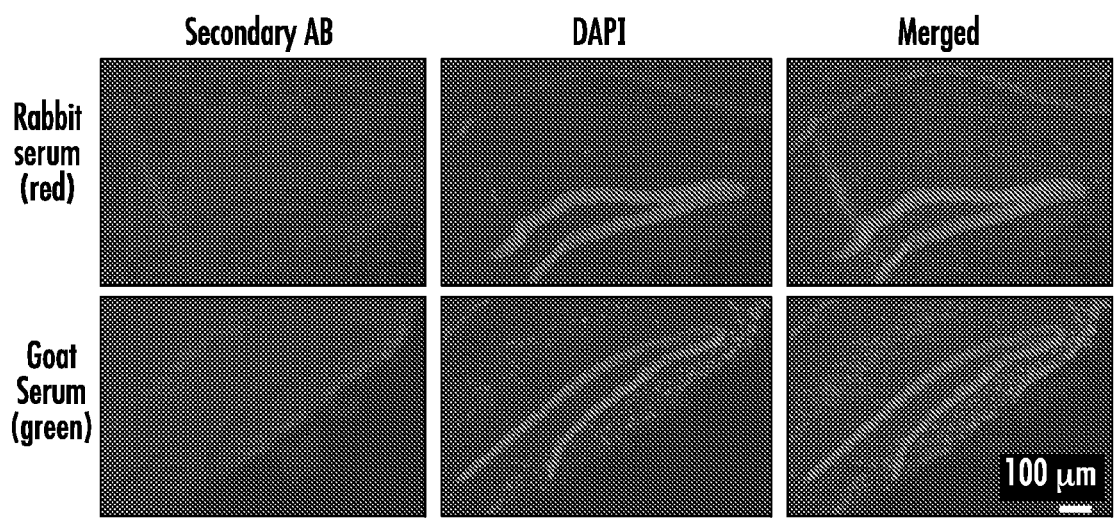
Figure 28:
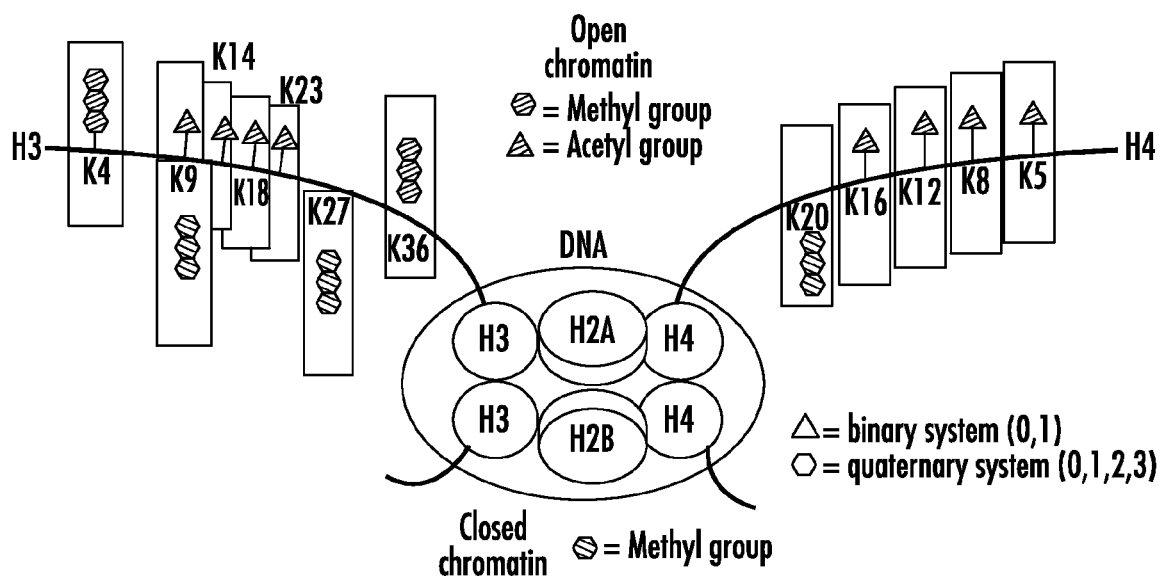
Figure 29A:
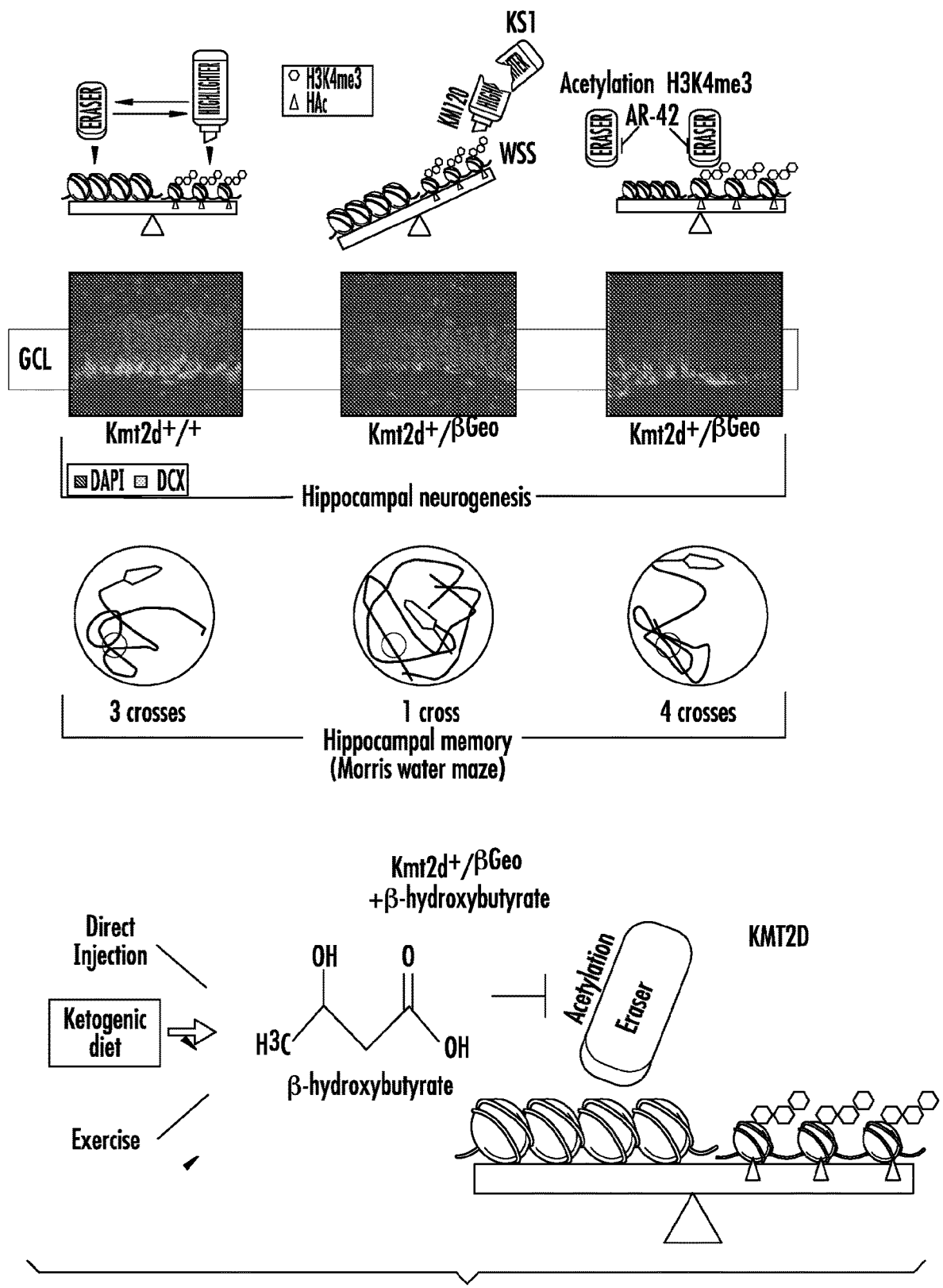
Figure 29B:
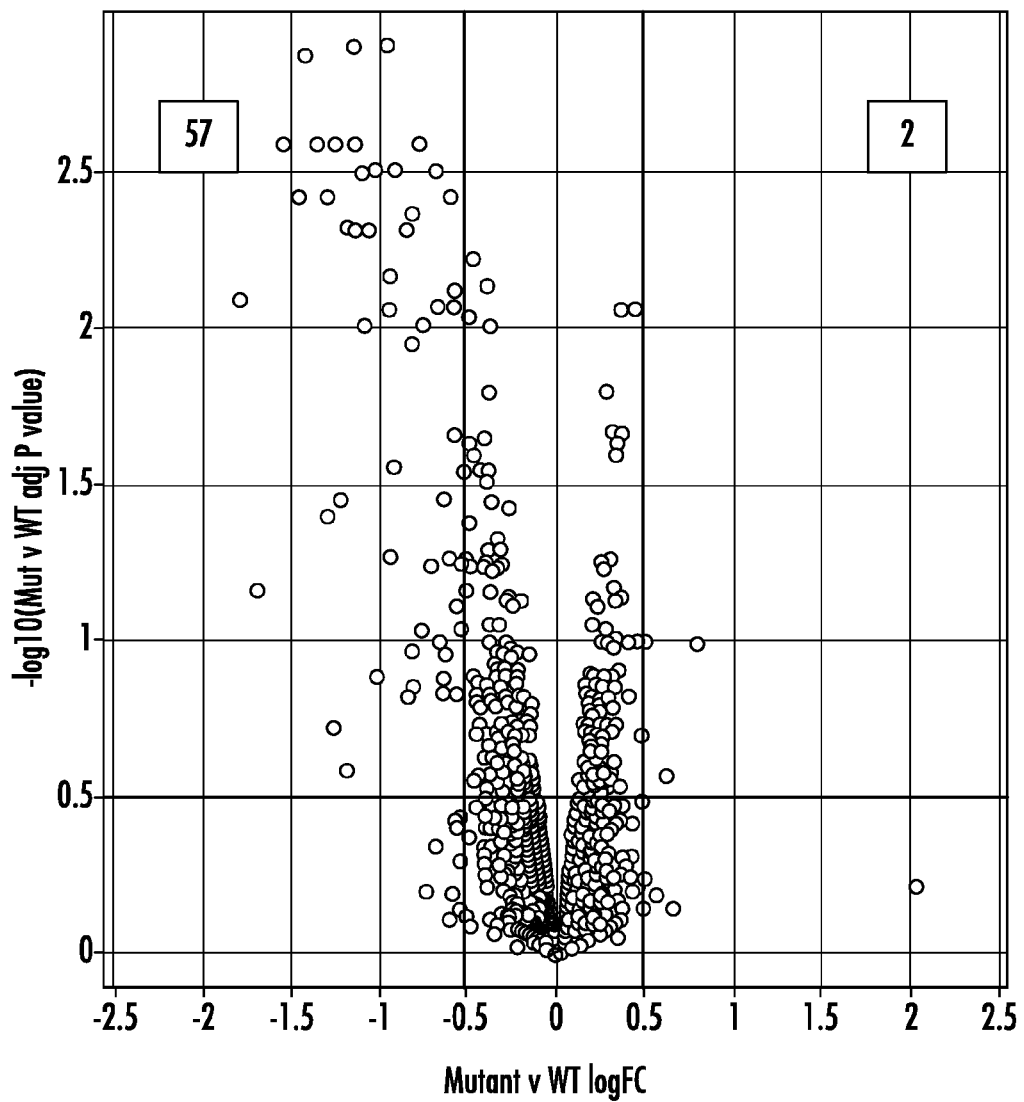
Figure 29C:
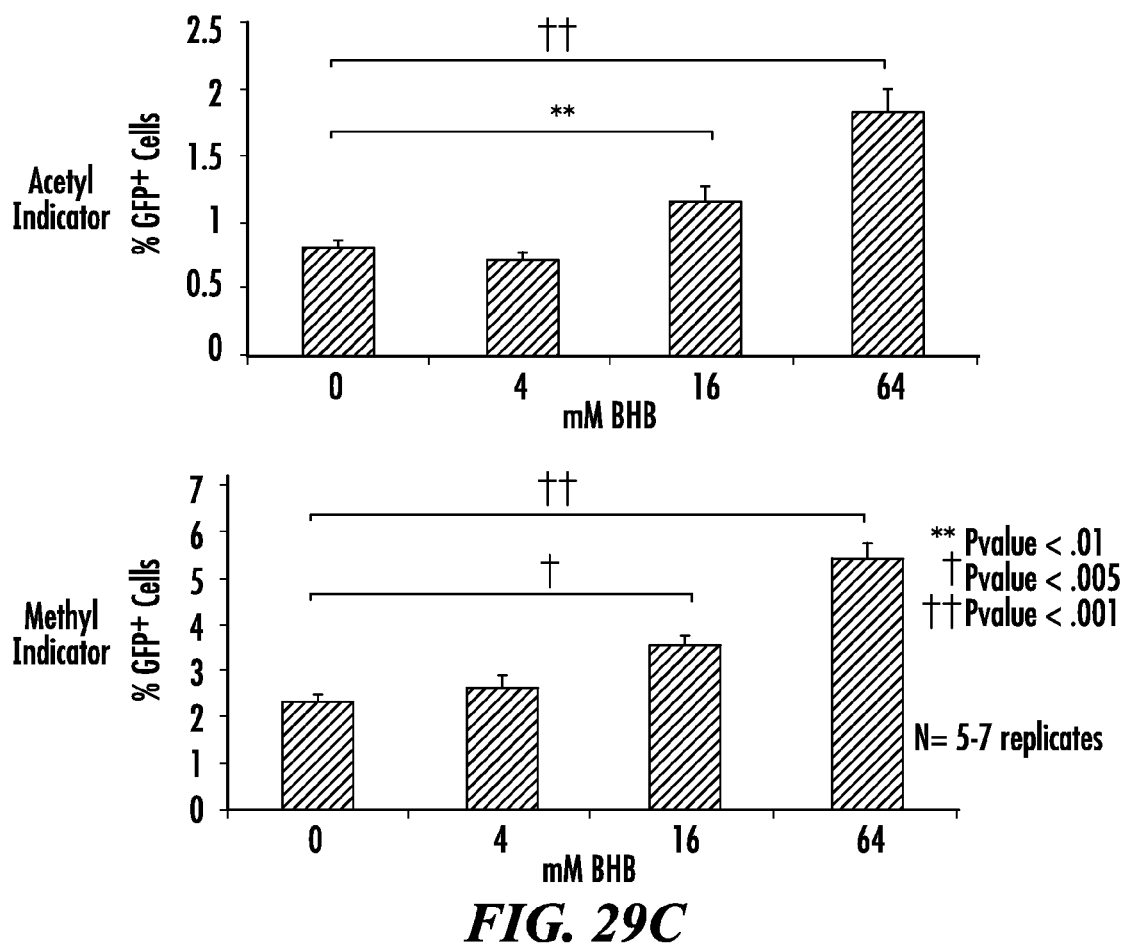
Figure 29D:
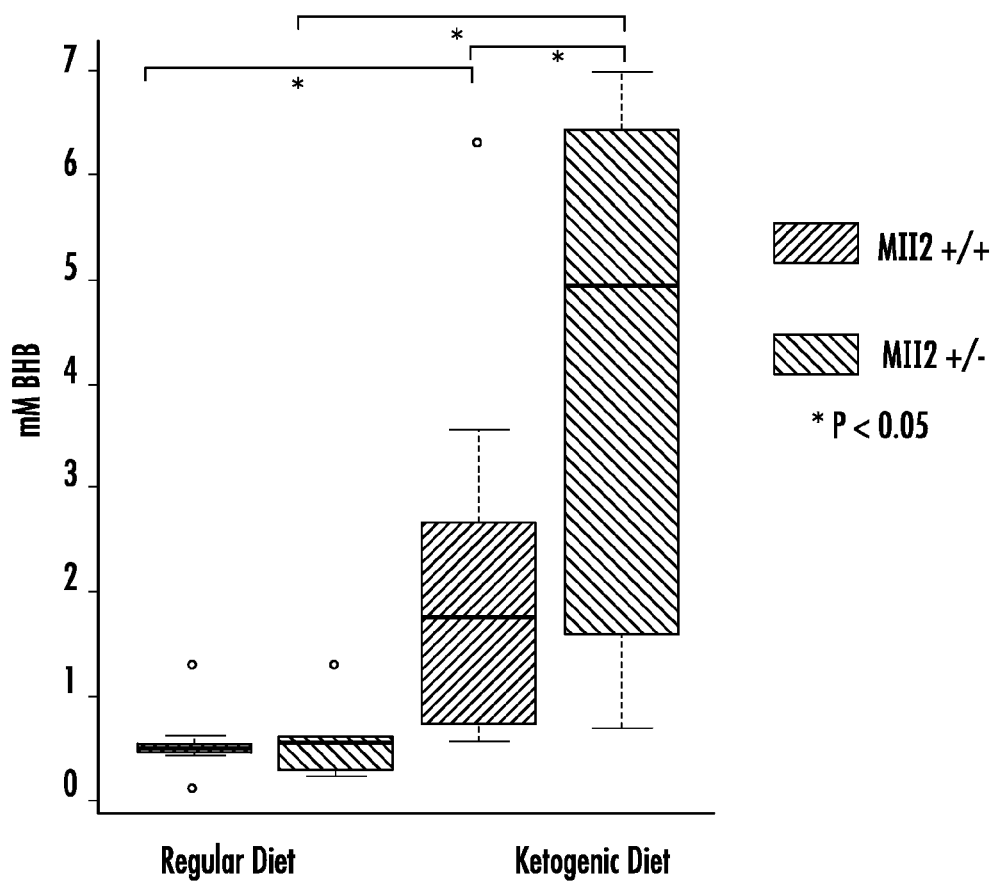
Figure 29E:
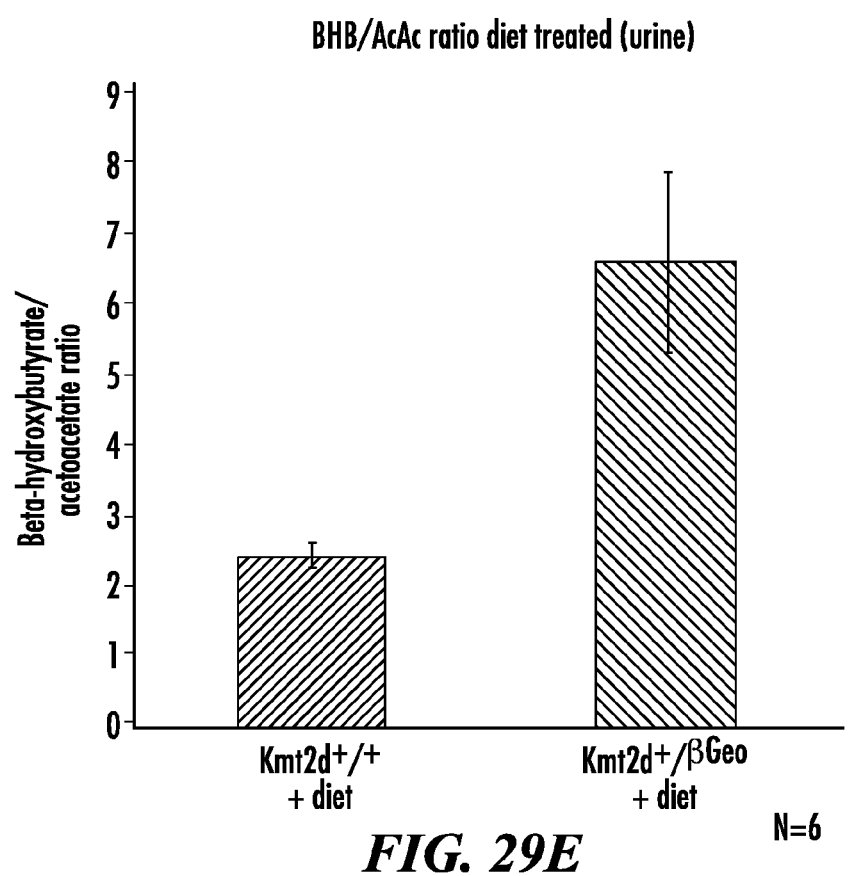
Figure 29F:
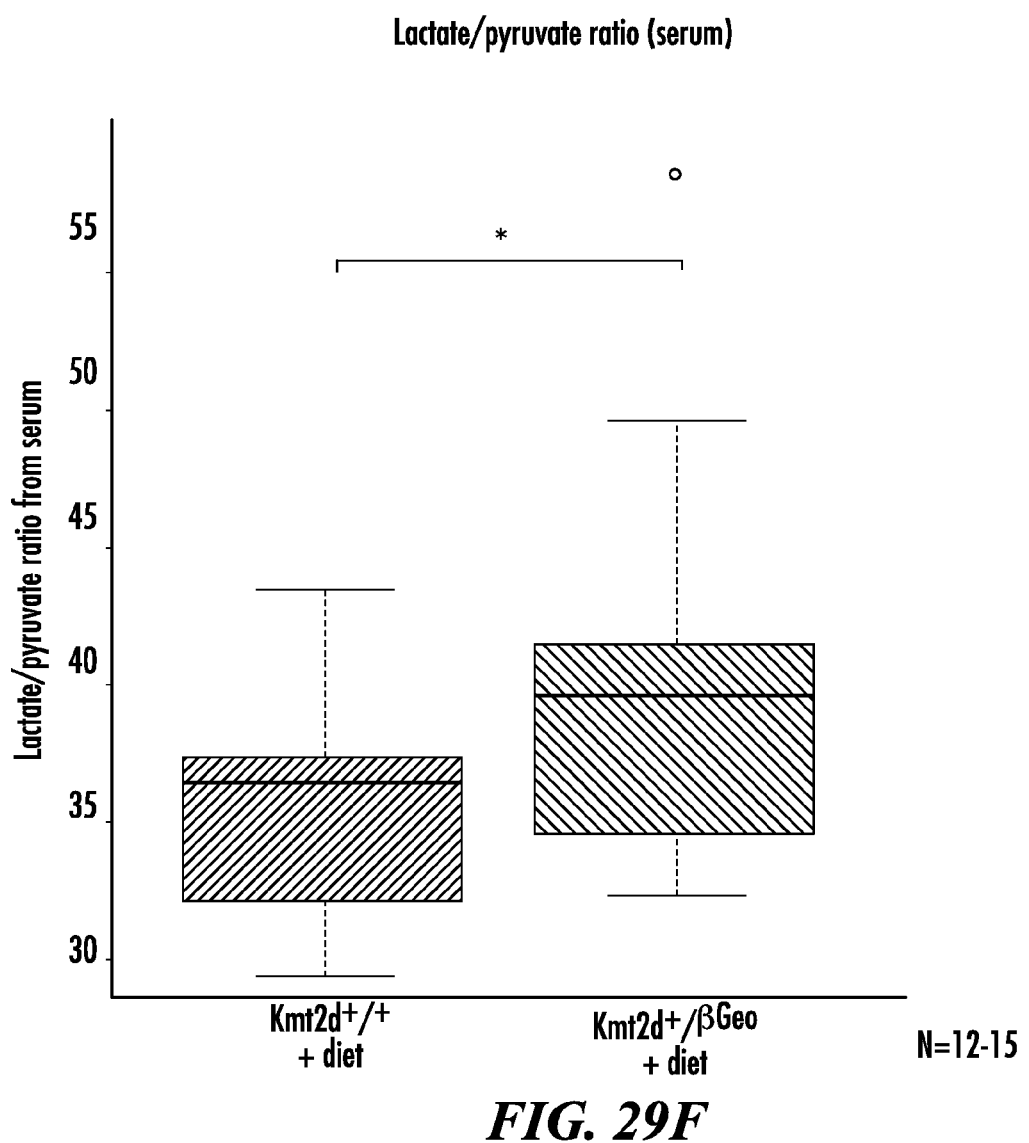
Figure 29G:
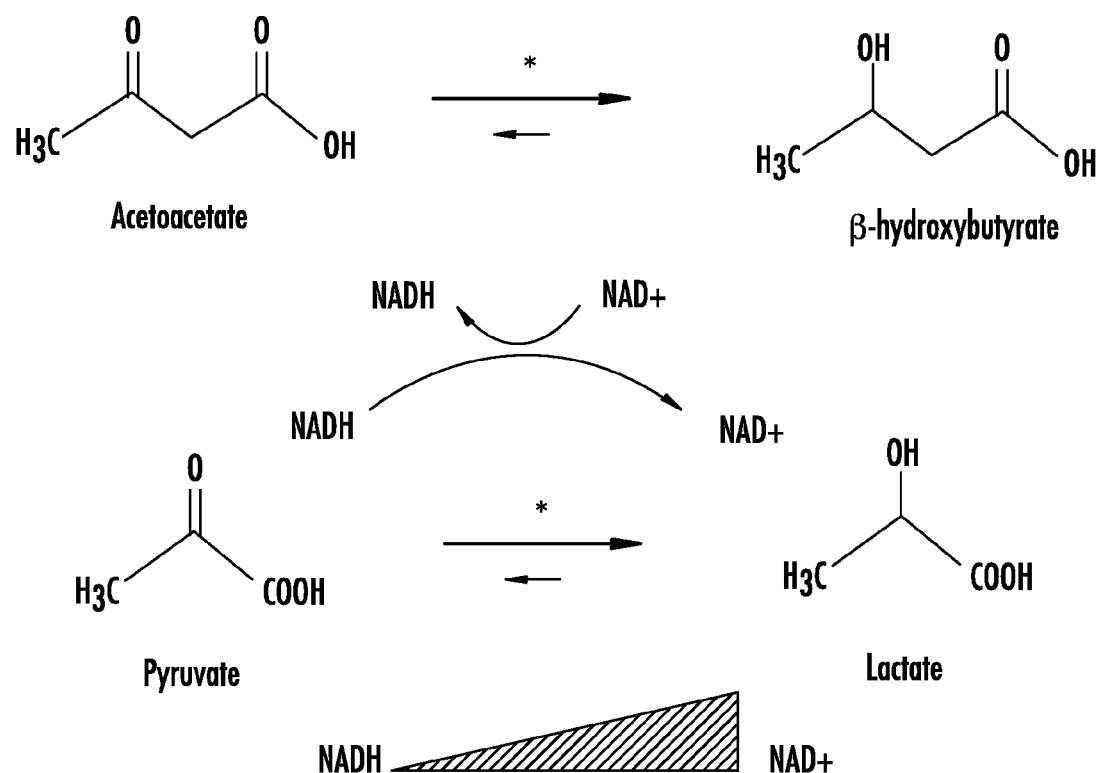
Figure 30:
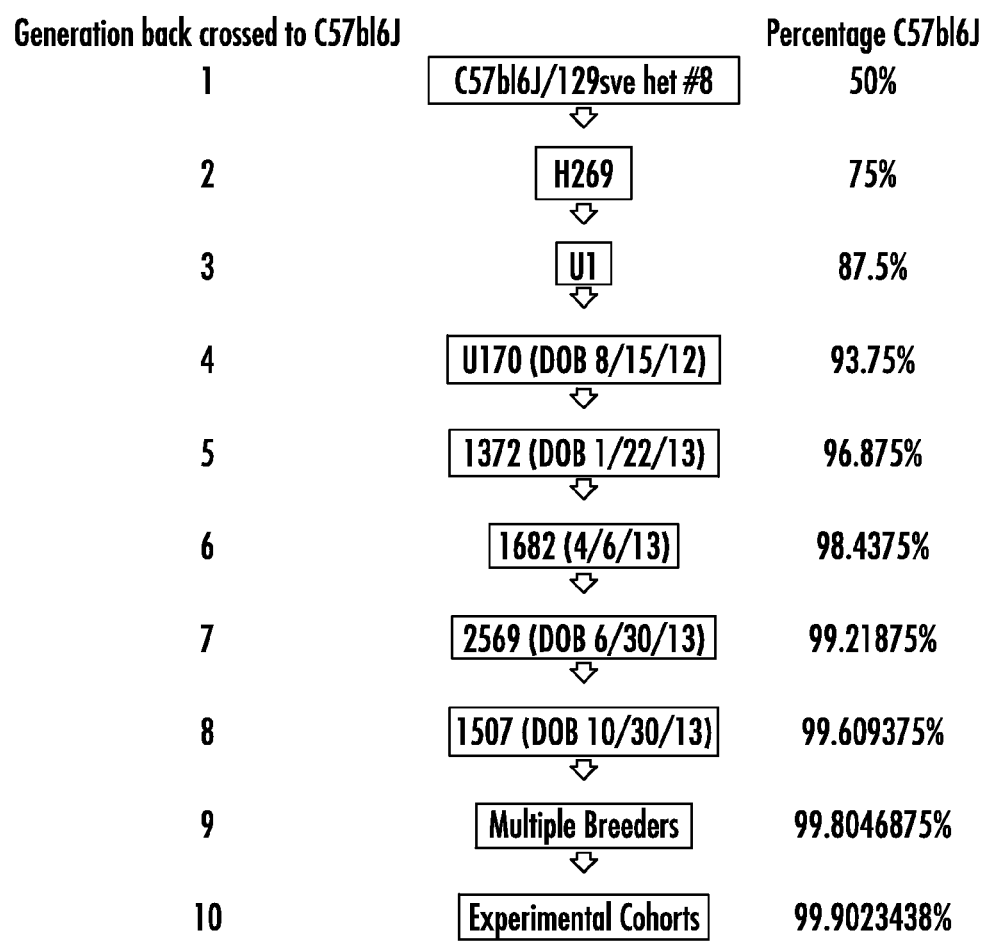
Figure 31A:
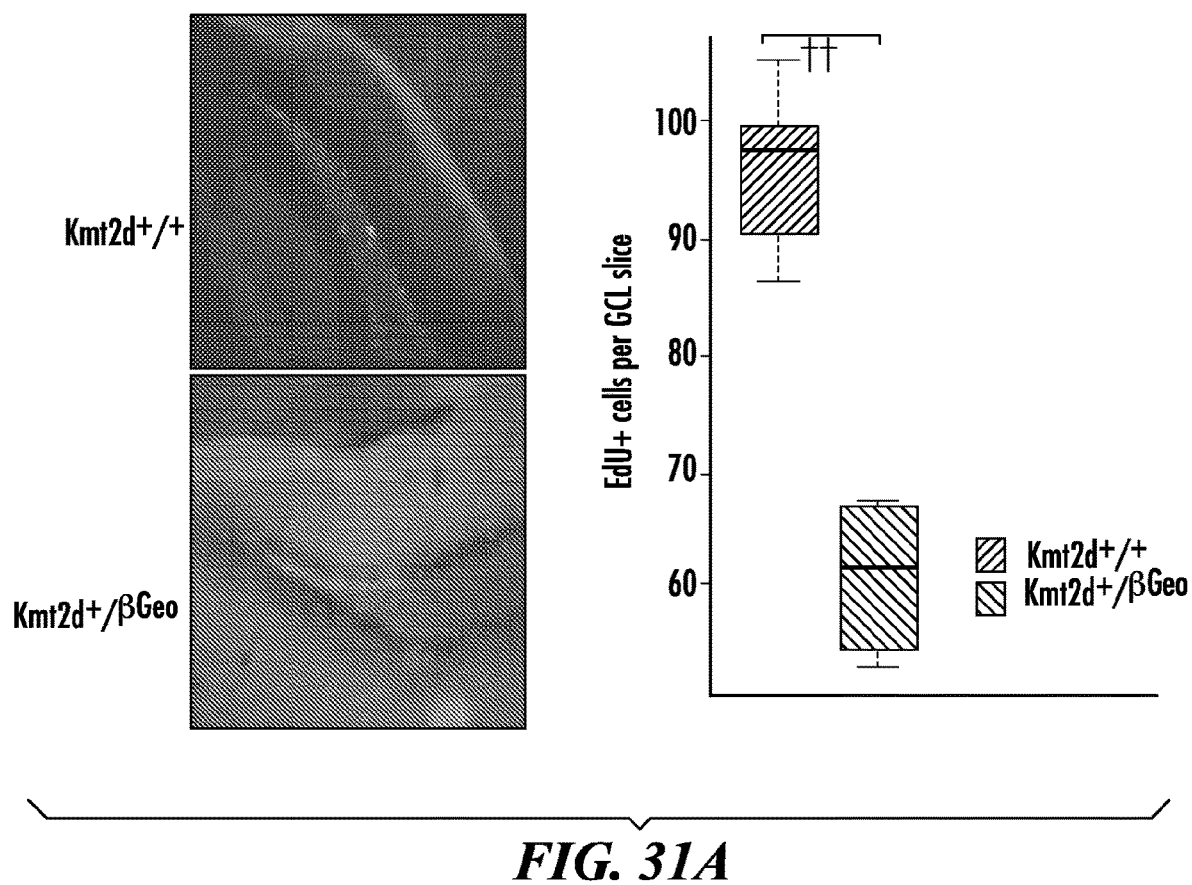
Figure 31B:
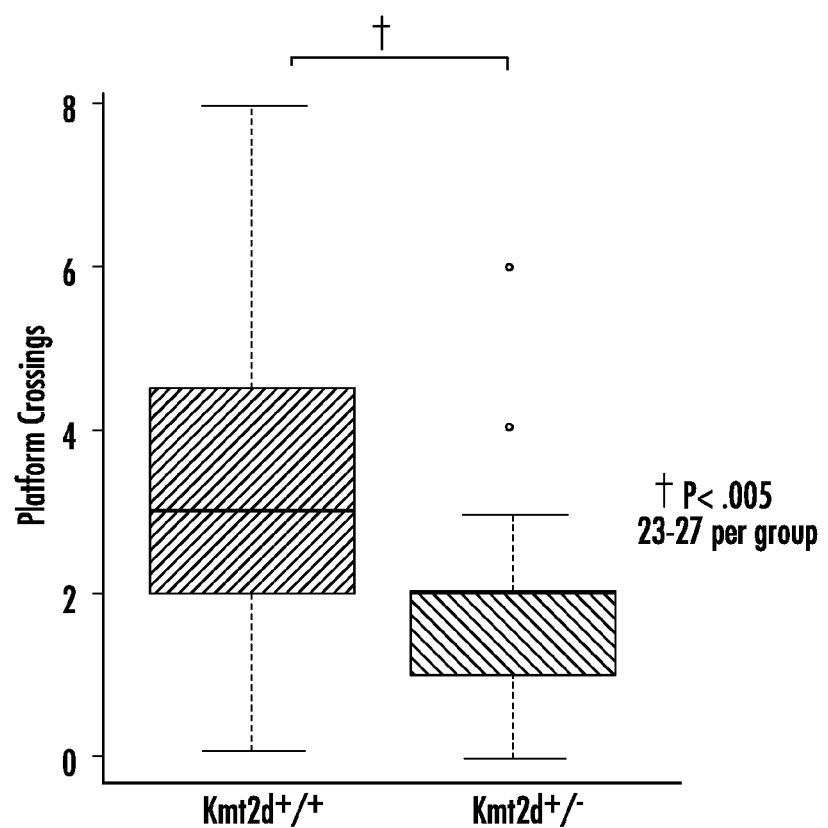
Figure 32A:
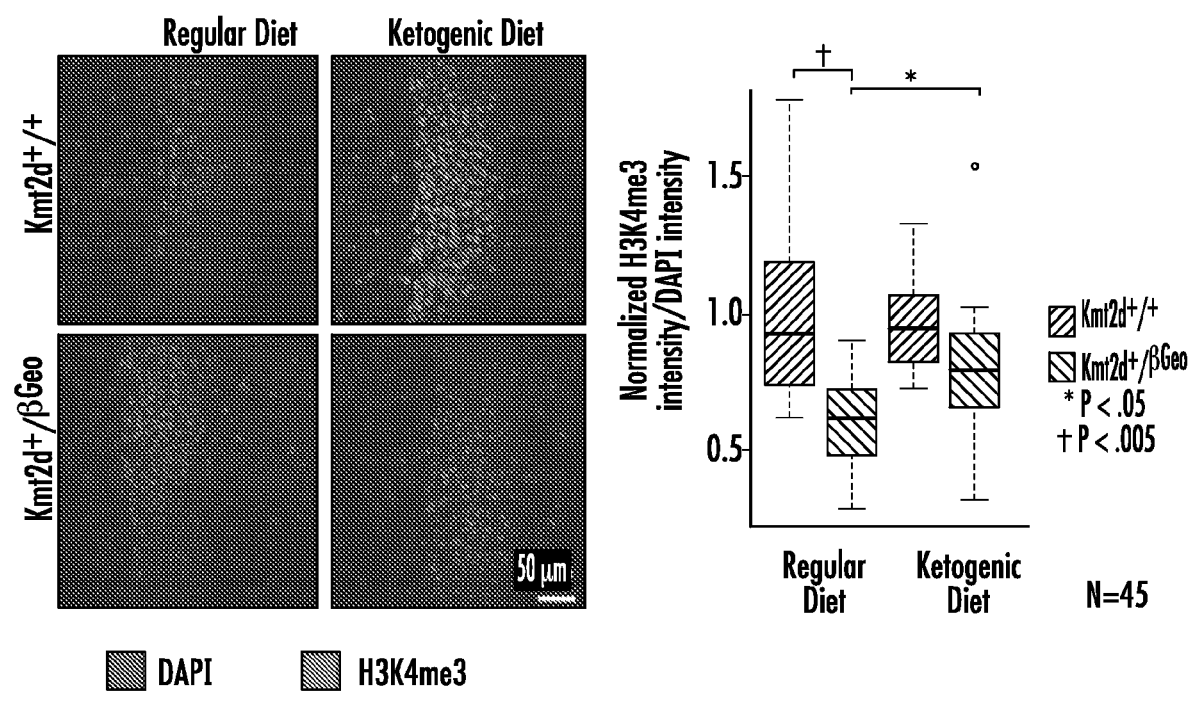
Figure 32B:
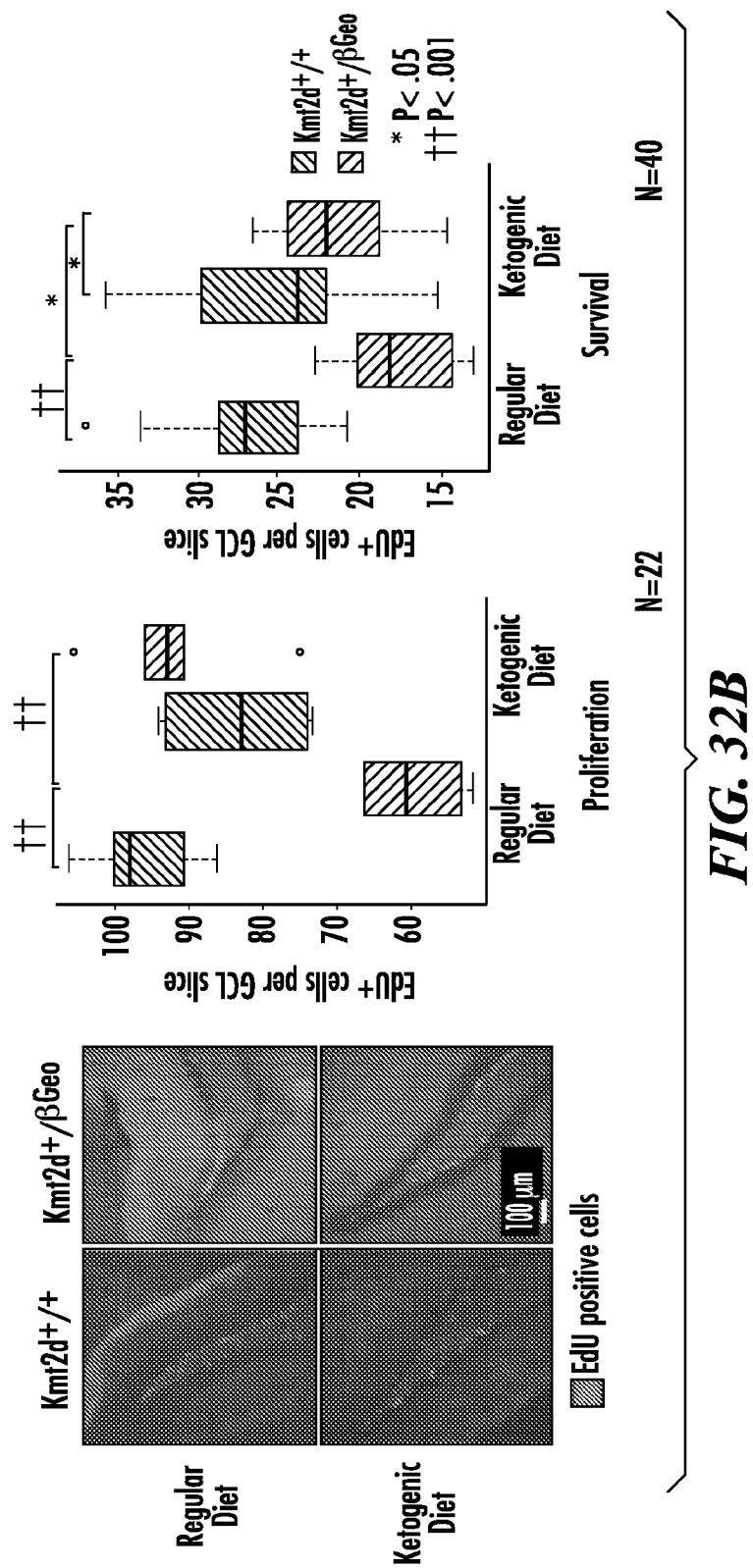
Figure 32C:
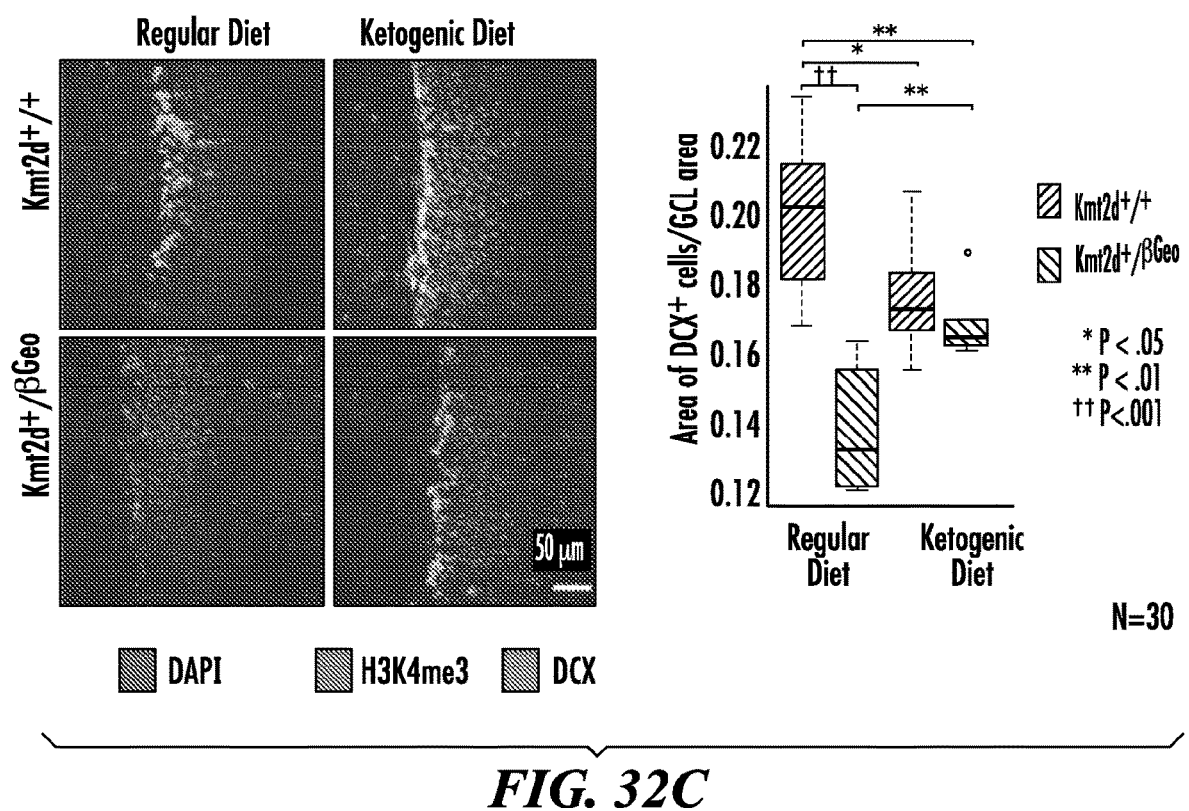
Figure 33:
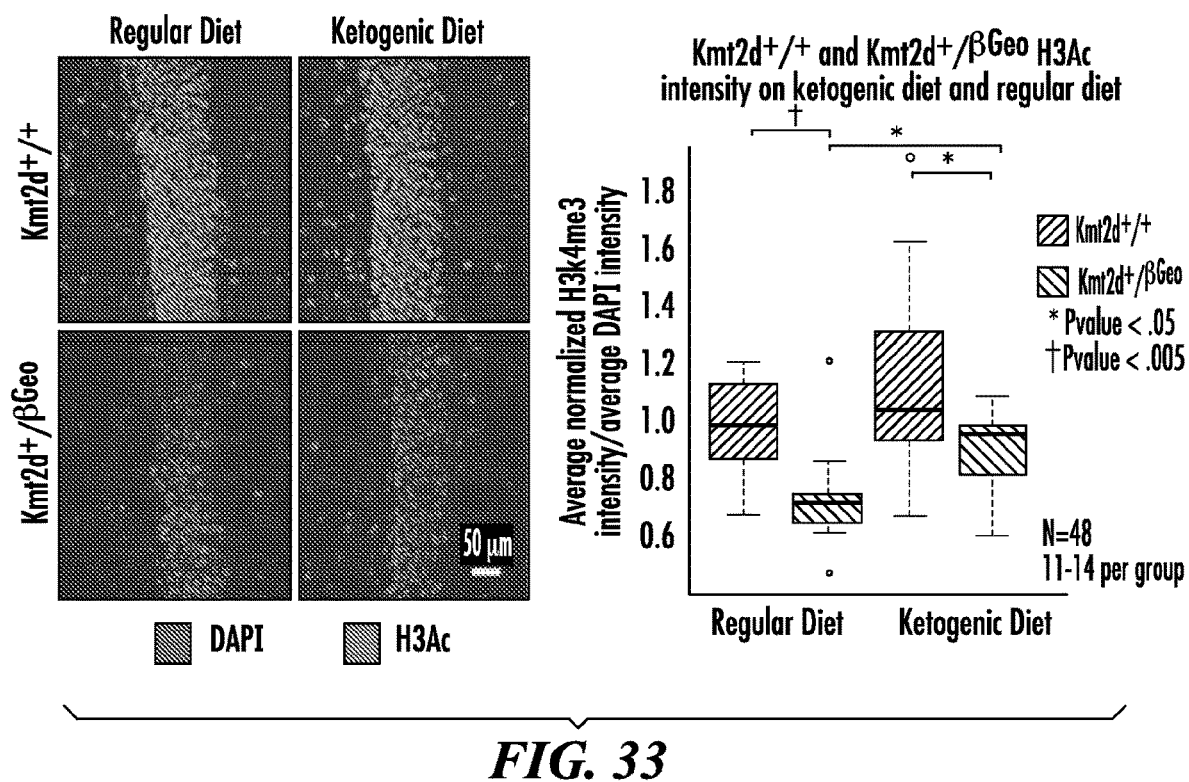
Figure 34A:
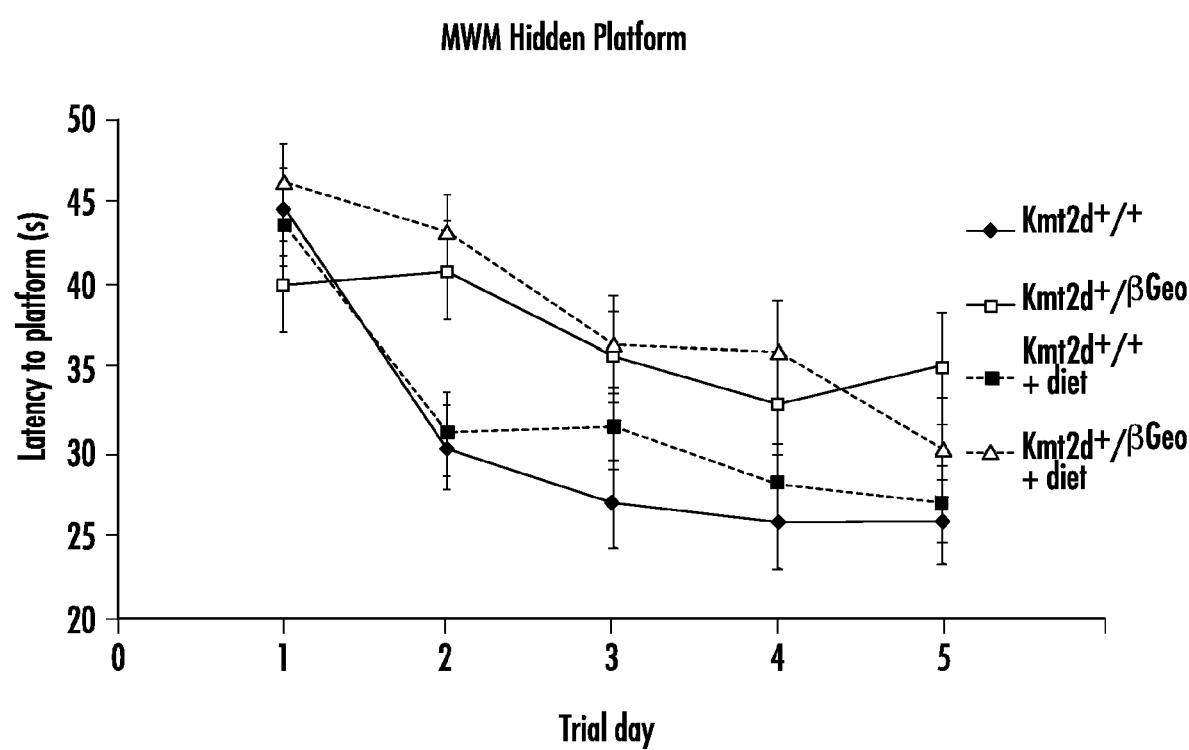
Figure 34B:
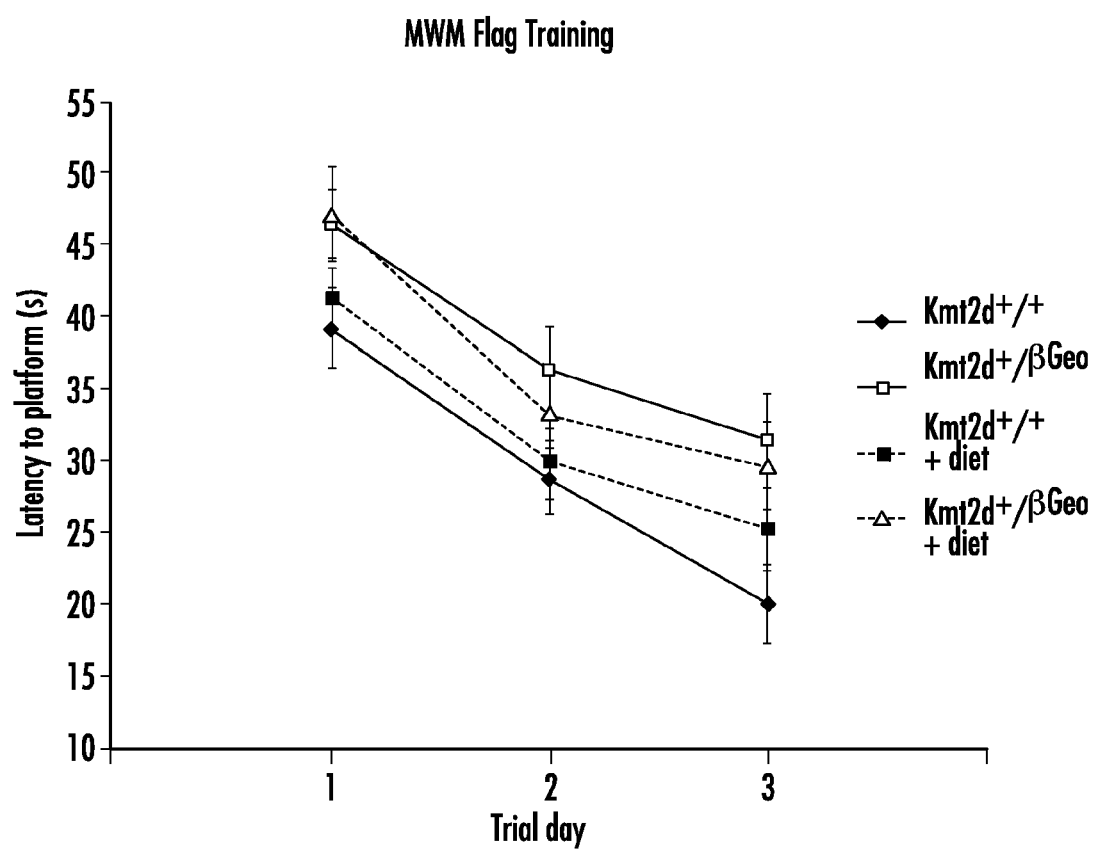
Figure 35A:
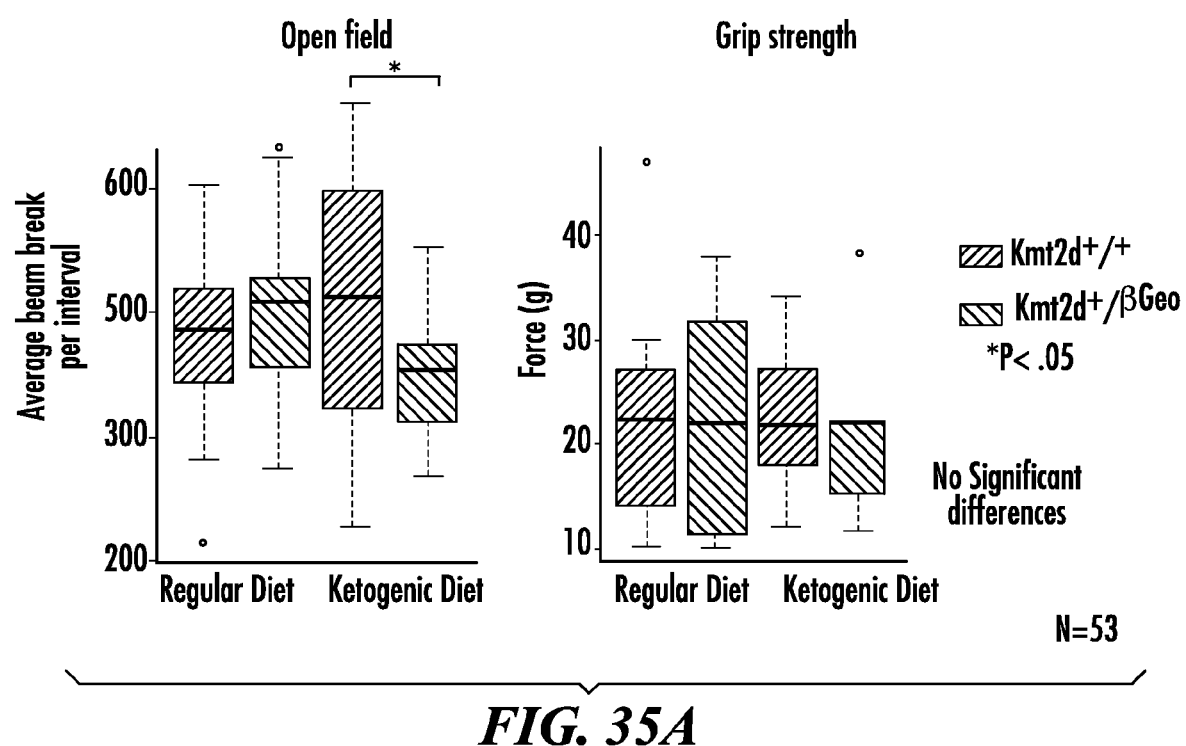
Figure 35B:
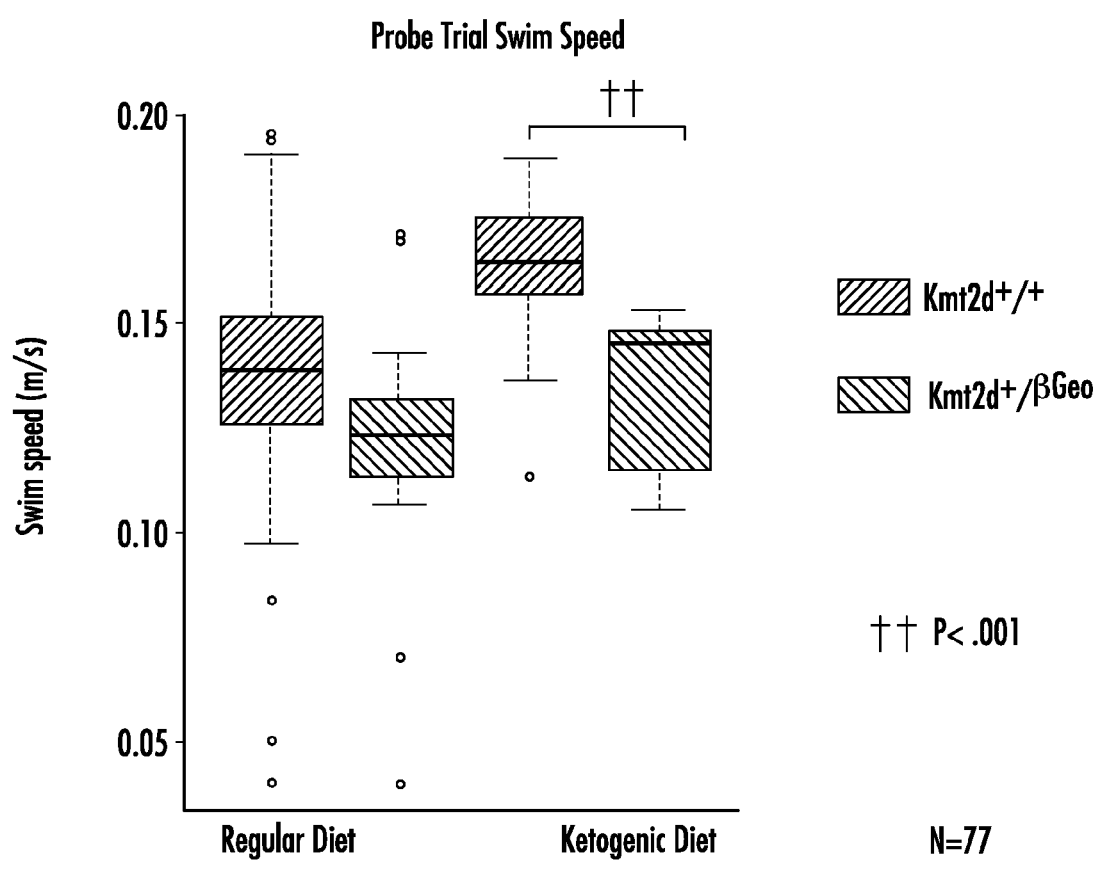
Figure 36A:
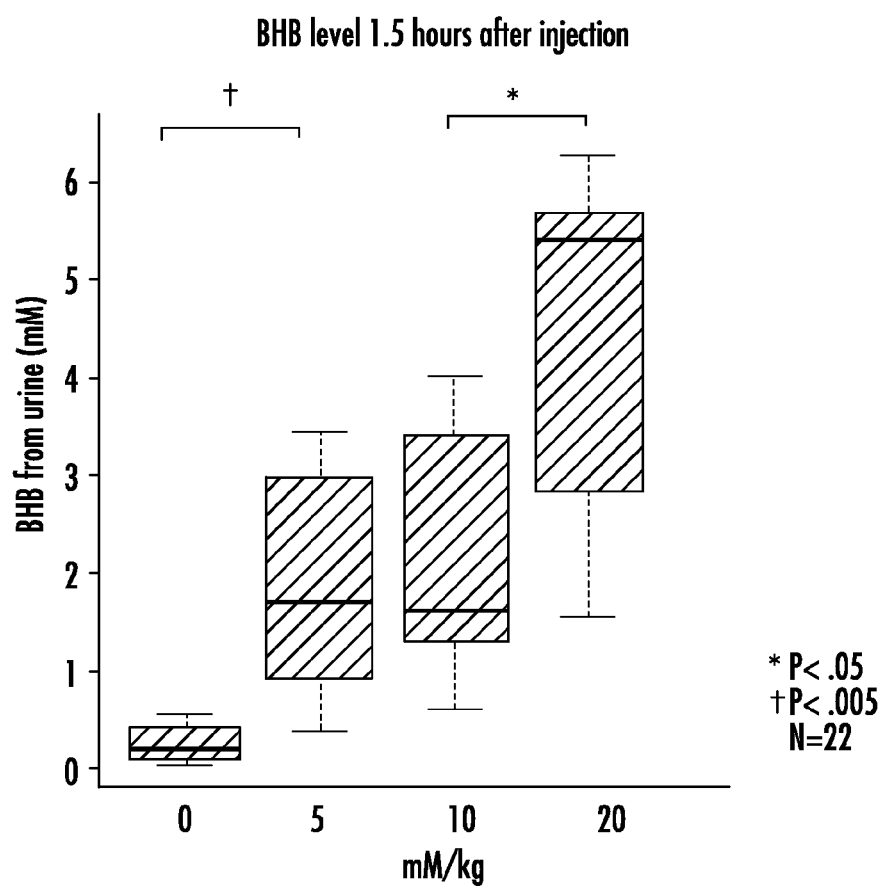
Figure 36B:
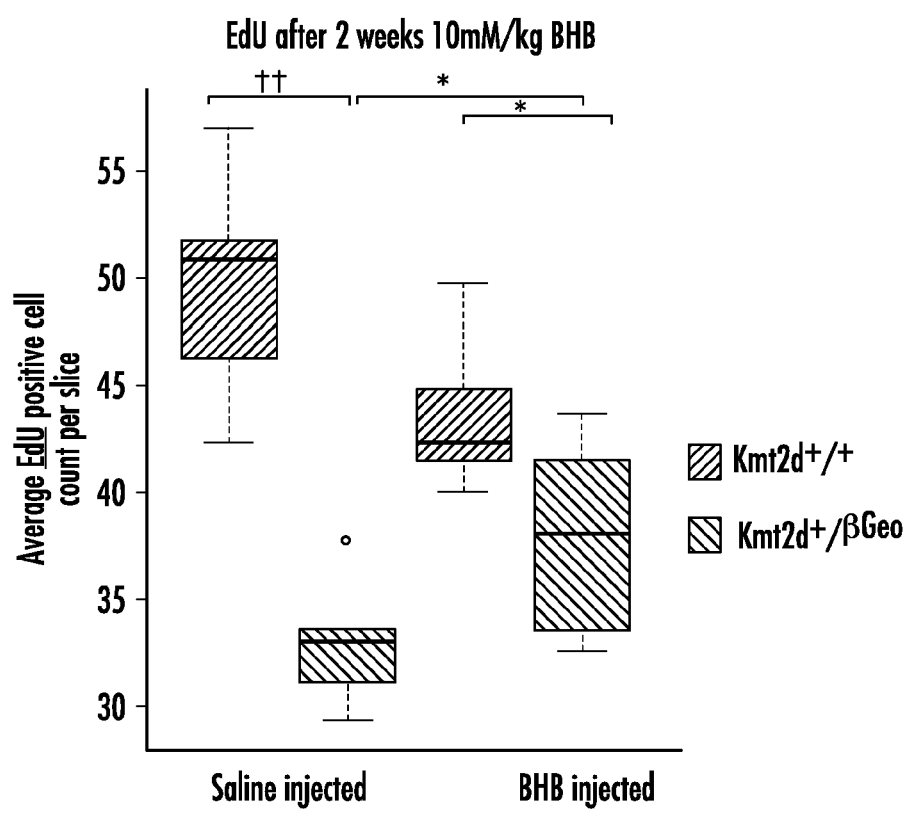
Figure 36C:
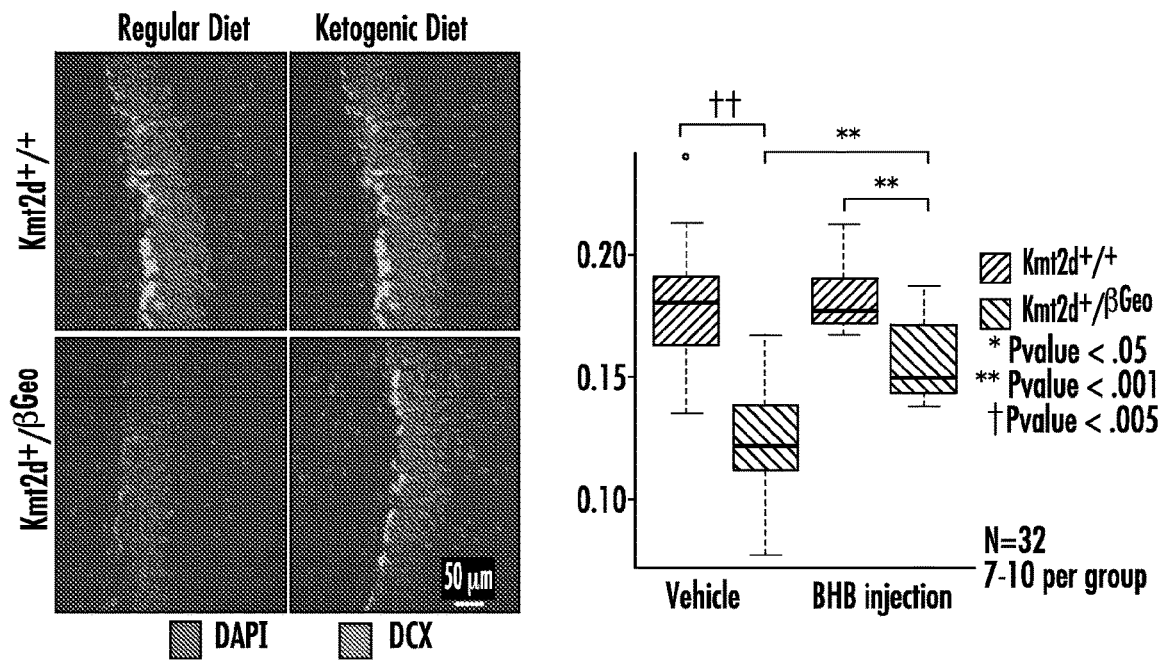
Figure 36D:
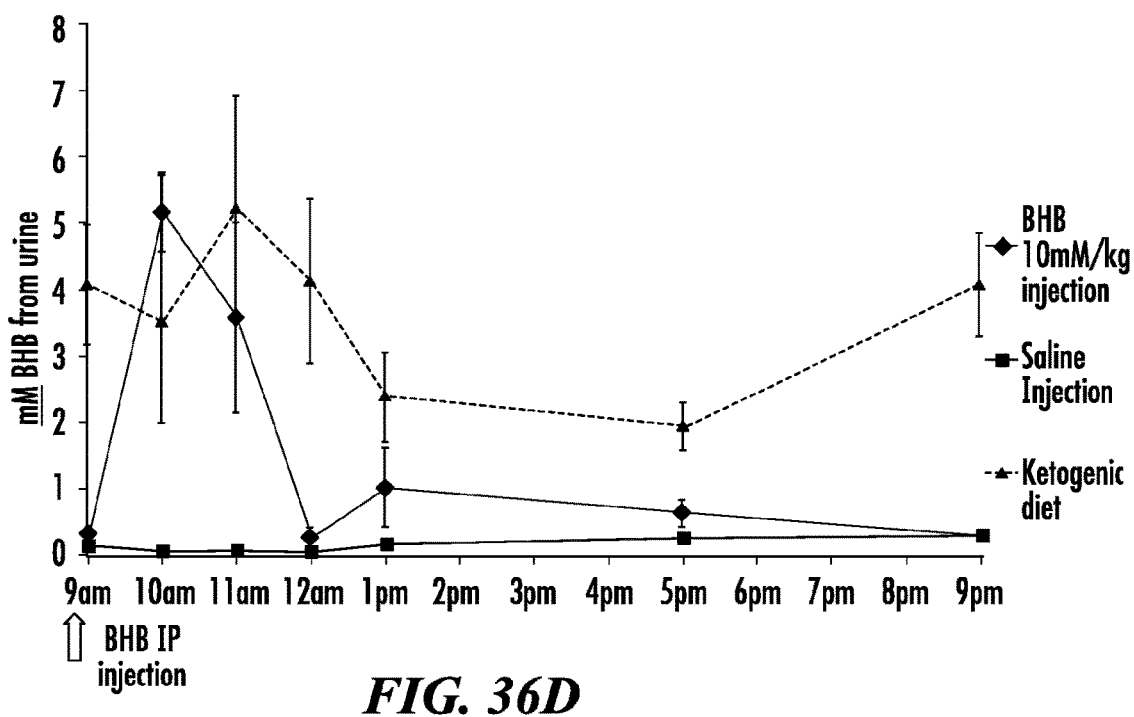

Having thus described the presently disclosed subject matter in general terms, reference will now be made to the accompanying Figures, which are not necessarily drawn to scale, and wherein:

FIG. 1 shows components of the epigenetic machinery. This machinery consists of writers (highlighters) and erasers of marks (for example, trimethylation of lysine 4 on histone H3 (H3K4me3)) as well as readers of those marks. A net balance between systems that remove and add a particular mark must be achieved;

FIG. 2 shows selected Mendelian disorders of the histone machinery caused by alterations of writers (highlighters) and erasers. Acetylation is a binary mark (present or not), and histone lysine methylation a quaternary mark (present as mono-, di-, tri-, or unmethylated). The diagram illustrates these two types of modifications on two of the N-terminal histone tails, histone H3 and histone H4. The writers (highlighters) and erasers place and remove the modifications; some of these are associated with open, permissive chromatin (green), and others are associated with closed, repressive chromatin (red). Based on the enzymatic component of the epigenetic machinery involved and the predicted consequence of the reported mutations for each disorder, the diagram shows conditions that would be expected to shift the balance toward closed chromatin states at target loci (top) and conditions that would be expected to shift the balance toward open chromatin states at target loci (bottom);

FIG. 3 shows therapeutic approaches based on understanding and restoring the balance of chromatin states;

FIG. 4 shows a schematic diagram of an embodiment of the presently disclosed genetically encoded indicator system;

FIG. 5A, FIG. 5B, FIG. 5C, FIG. 5D, FIG. 5E, and FIG. 5F show that the $Kmt2d^{+/\beta Geo}$ mouse model of Kabuki syndrome demonstrates hippocampal memory defects. FIG. 5A shows the domain organization of KMT2D/MLL2 homologs in mouse and human, with the relative position of the H3K4 methyltransferase SET domain indicated in red and other domains by additional colors. The human and murine chromosomal assignment (Chr) is shown. FIG. 5B shows that the $Kmt2d^{\beta Geo}$ targeting event introduces a β-Geo cassette including a strong splice acceptor (SA) sequence and a 3' cleavage and polyadenylation signal (pA) into intron 50 of Kmt2d on mouse chromosome 15. FIG. 5C shows real-time PCR using primers specific for exons 20 or 52 of Kmt2d (arrows) confirms a substantial reduction (~50%) in mRNA corresponding to sequences distal to the β-Geo insertion site when compared to proximal sequences in $Kmt2d^{+/\beta Geo}$ mice, in comparison to $Kmt2d^{+/+}$ littermates. Results reflect three technical replicates for each of 3 $Kmt2d^{+/+}$ and 2 $Kmt2d^{+/\beta Geo}$ mice. FIG. 5D shows that ChIP-seq reveals a genome-wide deficiency of H3K4me3 in cells from $Kmt2d^{+/\beta Geo}$ mice, when compared to cells from $Kmt2d^{+/+}$ littermates. A positive value indicates a higher locus-specific peak in $Kmt2d^{+/\beta Geo}$ mice. Each point corresponds to a genomic location with a peak in at least one sample. Significantly differentially bound loci are red, while others are gray. FIG. 5E shows that there was no difference in positional preference between genotypes during the habituation phase [identical objects (L/R)]. $Kmt2d^{+/\beta Geo}$ mice spent less time with a novel object placed to the left (L) of a habituated object on the right (R) compared to $Kmt2d^{+/+}$ littermates, which also significantly improved from habituation phase [Novel object (L)]. n=13 (+/+), 10 (+/βGeo). FIG. 5F shows that $Kmt2d^{+/\beta Geo}$ mice showed a reduced frequency in platform zone crossings during the probe trial phase of Morris water maze testing, n=48 (+/+), 32 (+/βGeo). *P<0.05. †P<0.005; ††P<0.001;

FIG. 6A and FIG. 6B show the integration site of gene trap in the $Kmt2d^{\beta Geo}$ allele. FIG. 6A shows the DNA sequence of the targeted allele showing the sequence for Kmt2d exon 50 (red) and intron 50 (blue) and the gene trap encoding the β-Geo cassette (purple). FIG. 6B shows immunoprecipitated protein using an antibody directed against KMT2D shows immunoreactivity for β-galactosidase in cellular lysates from Kmt2d$^{+/βGeo}$ mice but not Kmt2d$^{+/+}$ littermates. The presence of this hybrid protein suggests that mRNA from the Kmt2d$^{βGeo}$ allele is both transcribed and translated;

FIG. 7A, FIG. 7B, and FIG. 7C show that Kmt2d$^{+/βGeo}$ mice show overlapping phenotypic features with patients with KS: decreased protrusion of the maxilla over the mandible can be seen (FIG. 7A) when skin is removed and (FIG. 7B) on radiographs in Kmt2d$^{+/βGeo}$ mice, when compared to Kmt2d$^{+/+}$ littermates (n≥5 for both groups). This was verified by a group of investigators blinded to genotype which gave Kmt2d$^{+/+}$ mice a significantly higher maxillary protrusion score than Kmt2d$^{+/βGeo}$ littermates (FIG. 7C). $^{†}$P<0.005;

FIG. 8 shows that Kmt2d$^{+/βGeo}$ mice have context related memory defects. Kmt2d$^{+/βGeo}$ show impaired performance in a fear conditioning assay, when compared to Kmt2d$^{+/+}$ littermates. n=20 (+/+), 8 (+/βGeo). P<0.05 (repeated measures ANOVA comparing two genotypes in all time points);

FIG. 9 shows that Kmt2d$^{+/βGeo}$ mice show no deficit in flag trial. Kmt2d$^{+/βGeo}$ mice and Kmt2d$^{+/+}$ littermates show similar performance during flag trials prior to Morris water maze testing (as reflected by no significant difference in a repeated measures ANOVA), suggesting no inherent impairment to task completion such as visual impairment, in subsequent memory-based testing. N.S., n=15 (+/+), 9 (+/βGeo);

FIG. 10A, FIG. 10B, and FIG. 10C show the assessment of motor function in Kmt2d$^{+/βGeo}$ and Kmt2d$^{+/+}$ mice. Kmt2d$^{+/βGeo}$ mice did not show any deficit in general activity level (as monitored by beam breaks in open field testing)(FIG. 10A) or grip strength (FIG. 10B), when compared to Kmt2d$^{+/+}$ littermates, and had comparable swimming speed in the probe trial of the Morris Water Maze (FIG. 10C). Open field testing: N.S., n=11 (+/+), 11 (+/βGeo); grip strength: N.S., n=18 (+/+), 8 (+/βGeo). MWM probe trial: N.S., n=29 (+/+), 23 (+/βGeo);

FIG. 11A, FIG. 11B, FIG. 11C, and FIG. 11D show the escape latencies during Morris water maze training. FIG. 11A shows average latency to platform zone for Kmt2d$^{+/βGeo}$ (yellow) and Kmt2d$^{+/+}$ animals (blue). Repeated measures ANOVA showed no significant difference between groups across all time points. FIG. 11B shows Kmt2d$^{+/βGeo}$ mice on 10 mg/kg/day of AR-42 (yellow triangle) and Kmt2d$^{+/+}$ animals on 10 mg/kg/day of AR-42 (blue circle). No significant difference is observed. FIG. 11C shows Kmt2d$^{+/+}$ animals with (blue circle) and without (blue square) 10 mg/kg/day of AR-42. Significant difference with P<0.01. FIG. 11D shows Kmt2d$^{+/βGeo}$ animals with (yellow rhombus) and without (yellow triangle) 10 mg/kg/day of AR-42. No significant difference is observed. n=32 (+/βGeo, vehicle), 44 (+/+, vehicle), 9 (+/βGeo, AR-42), 14 (+/+, AR-42);

FIG. 12A, FIG. 12B, FIG. 12C, FIG. 12D, FIG. 12E, FIG. 12F, and FIG. 12G show that Kmt2d$^{+/βGeo}$ mice demonstrate a global deficiency of H3K4me3 in the DG associated with reduced GCL volume and neurogenesis. FIG. 12A shows that immunofluorescence reveals intense expression of KMT2D (red signal) in the dentate gyrus GCL and pyramidal layer of Kmt2d$^{+/+}$ mice. FIG. 12B shows immunofluorescence showing H3K4me3 (red) and DAPI (blue) in the GCL of Kmt2d$^{+/βGeo}$ mice and Kmt2d$^{+/+}$ littermates. FIG. 12C shows that quantification reveals a reduced H3K4me3/ DAPI signal intensity ratio within the GCL of Kmt2d$^{1/βGeo}$ mice compared to Kmt2d$^{+/+}$ littermates. n=9 (+/+), 5 (+/βGeo). FIG. 12D shows that the calculation of GCL area (red outline) in every sixth brain slice allowed demonstration of reduced GCL volume (FIG. 12E) in Kmt2d$^{+/βGeo}$ mice compared to Kmt2d$^{+/+}$ littermates. n=4 (+/+), 5 (+/βGeo). FIG. 12F and FIG. 12G show that immunofluorescence reveals reduced representation of cells positive for doublecortin (DCX), a marker for neurogenesis, in the GCL of Kmt2d$^{+/βGeo}$ mice compared to Kmt2d$^{+/-}$ littermates. n=4 (+/+), 4 (+/βGeo). *P<0.05; $^{††}$P<0.001;

FIG. 13 shows that H3K4me3 is decreased in the pyramidal layer in Kmt2d$^{+/βGeo}$ mice compared to Kmt2d$^{+/+}$ littermates. H3K4me3 is also significantly reduced in the pyramidal layer of the hippocampus, another cell layer with strong expression of KMT2D protein. n=5 (+/+), 5 (+/βGeo). **P<0.01;

FIG. 14A and FIG. 14B show the body and brain size in Kmt2d$^{+/βGeo}$ mice. While Kmt2d$^{+/βGeo}$ animals show a significant reduction in body weight, at 5 months of age when compared to Kmt2d$^{+/+}$ littermates (FIG. 14A), there was no significant difference in brain weight (FIG. 14B). Body, n=10 (+/+), 5 (+/βGeo). Brain, N. S., n=14 (+/+), 12(+/βGeo), *P<0.05;

FIG. 15 shows EdU incorporation. Kmt2d$^{+/βGeo}$ mice showed reduced incorporation of EdU in the GCL 30 days after the onset of injection, suggesting reduced neurogenesis and long-term neuronal survival, when compared to Kmt2d$^{+/+}$ littermates, as assessed by observers blinded to genotype. n=7 (+/+), 4 (+/βGeo) **P<0.01;

FIG. 16 shows decreased dendrites in DCX+ cells in GCL of Kmt2d$^{+/βGeo}$ mice. Immunofluorescence shows that Kmt2d$^{+/βGeo}$ animals show an apparent decrease in dendritic arborization of cells that are DCX+, when compared to Kmt2d$^{+/+}$ littermates;

FIG. 17A, FIG. 17B, FIG. 17C, FIG. 17D, FIG. 17E, FIG. 17F, FIG. 17G, FIG. 17H, and FIG. 17I show that the H3k4me3 epigenetic reporter allele demonstrates decreased activity in Kmt2d$^{+/βGeo}$ cells. FIG. 17A shows the domain organization encoded by the H4ac and H3K4me3 reporter alleles. The H4ac indicator includes H4 (lysine positions indicated), the C- and N-terminal halves of E-GFP separated by a short linker (L), the TAFII binding domain (BD) and a repetitive nuclear localization signal (NLS). The H3K4me3 indicator includes the H3 and the TAF3-PHD. FIG. 17B shows that the recognition of the histone tail mark by the relevant histone reader leads to reconstitution of GFP structure and function (fluorescence). FIG. 17C and FIG. 17D show that the acetylation indicator demonstrates increasing fluorescence with increasing amounts of the histone deacetylase inhibitor SAHA. FIG. 17E shows that activity of the H4ac indicator is lost upon mutagenesis of all potential acetylation sites from lysine to arginine. FIG. 17F shows that the H3K4me3 indicator demonstrates a dose dependent response to the histone deacetylase inhibitor AR-42 with decreased cell numbers at higher doses (red line). FIG. 17G shows that activity is greatly reduced upon mutagenesis of K4 in the H3 tail and D890A/W891A and M882A in the reader pocket. FIG. 17H shows that the H3K4me3 indicator shows reduced activity in murine embryonic fibroblasts (MEFs) derived from Kmt2d$^{+/βGeo}$ mice compared to Kmt2d$^{+/+}$ littermates. Both genotypes show a dose-dependent response to AR-42, with Kmt2d$^{+/βGeo}$ MEFs achieving untreated wild-type levels of activity at a dose of 5 μM. n=3 (+/+), 3 (+/βGeo), biological replicates for each dose. **P<0.01, $^{††}$P<0.001. FIG. 17I shows an experiment demonstrating that lysines on H4 are required for activity of the acetyl reporter: a) 293 cells not transfected but treated with 0 μM, 2.5 μM and 7.5 μM of Vorinostat (left to right); b) 293 cells transfected with reporter that has a single acetylation site with 0 μM, 2.5 μM and 7.5 μM of Vorinostat (left to right); c) 293 cells transfected with reporter with all possible acetylation sites changed from lysine's to arginines with 0 μM, 2.5 μM and 7.5 μM of Vorinostat (left to right);

FIG. 18A and FIG. 18B show that SAHA increases acetylation of the indicator (FIG. 18A) and show the saturation curve of the acetylation indicator as seen by % positive cells (FIG. 18B);

FIG. 19 shows that HDAC3 attenuates signal of the H4ac indicator. HEK293 cells stably expressing the H4ac indicator show increased signal upon stimulation with the histone deacetylase SAHA that is attenuated by recombinant expression of HDAC3. n=3 biologic replicates for each state, stable transfection. **P<0.01;

FIG. 20 shows that both indicators demonstrate a deficiency in Kmt2d$^{+/\alpha Geo}$ mice. Stable expression of the specified indicator into mouse embryonic fibroblasts (MEFs) demonstrates significant deficiencies in both histone H4 acetylation and H3K4 trimethylation activity in Kmt2d$^{+/\beta Geo}$ MEFs compared to Kmt2d$^{+/+}$cells, as assessed by the percentage of GFP positive cells. n=4 (+/+), 3 (+/βGeo). *P<0.05;

FIG. 21A and FIG. 21B show improved H3K4 trimethylation activity in Kmt2d$^{+/\beta Geo}$ cells transiently transfected with H3K4 trimethylation indicator and treated with MS275. Kmt2d$^{+/\beta Geo}$ MEFs show reduced H3K4 trimethylation activity when compared to Kmt2d$^{+/+}$cells, that is improved upon treatment with the histone deacetylase MS275 (FIG. 21A). Transiently transfected cells of both genotypes demonstrate comparable transfection efficiency as estimated by real time PCR when compared to a genomic control (FIG. 21B). n=6 (+/+), 6 (+/βGeo), biological replicates for each concentration, transient transfection. *P<0.05; **P<0.01; ††P<0.001;

FIG. 22A, FIG. 22B, FIG. 22C, and FIG. 22D show the in vivo responses to AR-42. FIG. 22A and FIG. 22B show that immunofluorescence reveals increased H3K4me3 in the GCL of Kmt2d$^{+/+}$ and Kmt2d$^{+/\beta Geo}$ mice upon treatment with 25 mg/kg/day of AR-42, with no difference between genotypes in the treated groups, n=4-5 per group. FIG. 22C shows that 25 mg/kg/day of AR-42 did not improve DCX expression in Kmt2d$^{+/\beta Geo}$ mice and reduced DCX expression in Kmt2d$^{+/+}$ animals, n=4-6 per group. FIG. 22D shows that DCX expression was improved in older mice (5-6 months) upon treatment of Kmt2d$^{+/\beta Geo}$ mice with 10 mg/kg/day of AR-42, n=3-4 per group. *P<0.05; **P<0.01; ††P<0.001;

FIG. 23A, FIG. 23B, FIG. 23C, FIG. 23D, FIG. 23E and FIG. 23F show the in vivo effects of AR-42. 1-2 month old mice of both genotypes show an increase in H3K4me3 (FIG. 23A and FIG. 23B) [n=5-6 per group] associated with a dose-dependent increase in neurogenesis in Kmt2d$^{+/\beta Geo}$ mice (FIG. 23C and FIG. 23D) (monitored by normalized DCX expression) [n=4-6 per group] upon treatment with the HDACi AR-42 with no difference between mutant and wild-type animals at a dose of 10 mg/kg/day. FIG. 23E shows that the genome-wide deficiency of H3K4me3 seen in Kmt2d$^{+/\beta Geo}$ mice is improved upon treatment with 10 mg/kg/day AR-42. FIG. 23F shows that the reduced frequency of platform crossing seen during Morris water maze testing of Kmt2d$^{+/\beta Geo}$ mice was normalized upon treatment with 10 mg/kg/day of AR-42. [n=48 (+/+, no treatment), 32 (+/βGeo, no treatment), 14 (+/+, 10 mg/kg/day AR-42), 9 (+/βGeo, 10 mg/kg/day AR-42)]. *P<0.05; **P<0.01; †P<0.005; ††P<0.001;

FIG. 24 shows the AR-42-induced expression of a known Kmt2d target gene. Klf10, a known target gene of Kmt2d (Guo et al. (2012) *Proc. Natl. Acad. Sci. U.S.A.* 109:17603-8), demonstrates reduced expression in spleen cells of Kmt2d$^{+/\beta Geo}$ mice that is normalized upon treatment with AR-42 n=4 per group. *P<0.054, †P<0.005;

FIG. 25A, FIG. 25B, FIG. 25C, FIG. 25D, and FIG. 25E show MA plots that indicate a shift in the balance of H3K4me3 upon treatment with AR-42significant differences in the locus-specific intensity of H3K4me3 are indicated in red, with the directionality and magnitude of each peak height reflecting the difference between the indicated states (genotype and AR-42 treatment status). Kmt2d$^{+/\beta Geo}$ animals demonstrate a downward shift compared to Kmt2d$^{+/+}$ littermates (FIG. 25A), which is recovered with AR-42 (FIG. 25B). These data indicate there may be some overcorrection which could be improved in future studies by using ChIP-seq as a biomarker. The difference between AR-42 treated and vehicle treated Kmt2d$^{+/+}$ animals is less notable (FIG. 25C), but obvious when comparing Kmt2d$^{+/\beta Geo}$ on AR-42 compared to Kmt2d$^{+/\beta Geo}$ littermates on vehicle (FIG. 25D) or both genotypes on AR-42 (FIG. 25E). CPM: counts per million, FC: fold change. n=3 (+/βGeo, vehicle), 3 (+/+, vehicle), 3 (+/βGeo, AR-42), 3 (+/+, AR-42);

FIG. 26A, FIG. 26B, FIG. 26C, FIG. 26D, and FIG. 26E show a visualization of shifts in balance between states (genotype or AR-42) as a function of intensity demonstrates an abnormality in Kmt2d$^{+/\beta Geo}$ that is responsive to AR-42: Kmt2d$^{+/\beta Geo}$ animals demonstrate a downward shift compared to Kmt2d$^{+/+}$ littermates (FIG. 26A; −2 log Q:589.5, P<2.2e-16), which is normalized (but somewhat over corrected) with AR-42 (FIG. 26B; −2 log Q:146.0, P<2.2e-16). The difference between AR-42-treated Kmt2d$^{+/+}$ mice and vehicle treated Kmt2d$^{+/+}$ littermates is less notable (FIG. 26C), but more evident when comparing Kmt2d$^{+/\beta Geo}$ on AR-42 to Kmt2d$^{+/\beta Geo}$ littermates on vehicle (FIG. 26D) or on both genotypes on AR-42 (FIG. 26E) (−2 log Q:359.9, P<2.2e-16). n=2 (+/βGeo, vehicle), 2 (+/+, vehicle), 2 (+/βGeo, AR-42), 2 (+/+, AR-42);

FIG. 27 shows serum control experiments for antibodies used for immunofluorescence. Non-specific binding was not observed when sections were sequentially exposed to serum from the same species matching the primary antibody for each experiment (i.e. rabbit for KMT2D and H3K4me3 and goat for doublecortin), followed by the secondary antibody used for KMT2D and H3K4me3 (anti-rabbit) or doublecortin (anti-goat);

FIG. 28 shows histone modifications relating to methylation for H3 and H4 tails, such as H3K9me3, H3K27me3, H3K36me3 and H3K20me3;

FIG. 29A, FIG. 29B, FIG. 29C, FIG. 29D, FIG. 29E, FIG. 29F, and FIG. 29G show the potential therapeutic use of BHB for the Kmt2d$^{+/\beta Geo}$ model. FIG. 29A shows a schematic diagram summarizing abnormalities observed in Kmt2d$^{+/\beta Geo}$ mice caused by the haploinsufficiency of the H3K4 methyltransferase Kmt2d which leads to a global deficiency of the open chromatin mark H3K4me3 in association with decreased neurogenesis in the granule cell layer of the dentate gyrus and decreased performance on the Morris water maze. These defects are rescued with AR-42, an HDACi, raising the possibility that BHB (an endogenous HDACi) may be able to provide similar therapeutic benefits to Kmt2d$^{+/\beta Geo}$ FIG. 29B shows that a gene expression microarray of Kmt2d$^{+/\beta Geo}$ and Kmt2d$^{+/+}$ littermates reveals an excess of genes that show decreased expression in the hippocampus of Kmt2d$^{+/\beta Geo}$ mice compared to littermates. FIG. 29C shows that HEK293T cells transfected with either an H4Ac or an H3K4me3 indicator both show a dose-dependent response to increased amounts of BHB in culture media. FIG. 29D shows that mice treated with MKD for two weeks showed a significant increase of BHB in their urine, while Kmt2d$^{+/\beta Geo}$ showed an even further elevation of BHB compared to diet treated Kmt2d$^{+/+}$ counterparts. Serum from diet treated mice revealed both a significant increased BHB/AcAc ratio (FIG. 29E) and lactate/pyruvate ratio (FIG. 29F) in Kmt2d$^{+/\beta Geo}$ compared to diet treated Kmt2d$^{+/+}$. FIG. 29G shows a schematic diagram showing that both the BHB/AcAc and lactate/pyruvate ratios are dependent on NAD+/NADH state. *$P<0.05$; ** $P<0.01$; †$P<0.005$; ††$P<0.001$;

FIG. 30 shows that the Kmt2d$^{+/\beta Geo}$ model has been fully backcrossed. Schematic diagram showing the backcrossing of Kmt2d$^{+/\beta Geo}$ model onto a pure C57b16j background;

FIG. 31A and FIG. 31B show that neurogenesis and hippocampal memory defects are observed in backcrossed B6 Kmt2d$^{+/\beta Geo}$. FIG. 31A shows that the neurogenesis defect (as visualized by EdU expression) that was observed on a mixed background Kmt2d$^{+/\beta Geo}$ is still present when fully backcrossed. FIG. 31B shows that similarly, the hippocampal memory defect (probe crossing in Morris water maze platform) is still present when fully backcrossed. †$P<0.005$; ††$P<0.001$;

FIG. 32A, FIG. 32B, FIG. 32C, and FIG. 32D show results from a representative treatment of Kmt2d$^{+/\beta Geo}$ with a ketogenic diet Immunofluorescence (IF) for H3K4me3 (red) and DAPI (blue) in the granule cell layer of the dentate gyrus (GCL) shows a decreased H3K4me3/DAPI fluorescence ratio between Kmt2d$^{+/\beta Geo}$ and Kmt2d$^{+/+}$ littermates in normal diet treated animals, which is increased on a two-week treatment with a ketogenic diet (FIG. 32A). To measure neurogenesis in the GCL, mice were injected with EdU and either sectioned immediately (proliferation) or after 30 days (survival). Kmt2d$^{+/\beta Geo}$ showed a decrease in both measures compared to Kmt2d$^{+/+}$ on the regular diet (FIG. 32B). Kmt2d$^{+/\beta Geo}$ mice showed a significant increase on a ketogenic diet. Neurogenesis results were confirmed with DCX IF staining (green) in the GCL, which showed a significant increase for Kmt2d$^{+/\beta Geo}$ on a ketogenic diet, correcting a deficiency between Kmt2d$^{+/+}$ and Kmt2d$^{+/\beta Geo}$ on a normal diet (FIG. 32C). Kmt2d$^{+/\beta Geo}$ showed a deficiency on platform crossings during the probe trial of the Morris water maze that was recovered with a two-week ketogenic diet treatment (FIG. 32D). *$P<0.05$; ** $P<0.01$; †$P<0.005$; ††$P<0.001$;

FIG. 33 shows the effects of MKD on H3 acetylation in the granule cell layer of the dentate gyrus. Immunofluorescence (IF) against H3Ac (red) and DAPI (blue) in the granule cell layer of the dentate gyrus shows a significant decrease in the H3Ac/DAPI ratio in Kmt2d$^{+/\beta Geo}$ compared to Kmt2d$^{+/+}$ littermates that is ameliorated with a two-week treatment with a ketogenic diet. *$P<0.05$; ** $P<0.01$; †$P<0.005$;

FIG. 34A and FIG. 34B show hidden platform and flag latencies. The latencies to find the hidden platform during the 5 days of training showed a significant interaction between genotype and treatment for Kmt2d$^{+/\beta Geo}$ compared to Kmt2d$^{+/+}$ as well as regular and MKD treatment (FIG. 34A) and the latencies to find the platform during the flag training did not show a significant interaction for either genotype or treatment (FIG. 34B);

FIG. 35A and FIG. 35B show that there are no significant changes for diet or genotype in test exploring strength or activity levels. Kmt2d$^{+/\beta Geo}$ did not show a significant difference from Kmt2d$^{+/+}$ on the regular diet, and did not decrease activity on the MKD on the open field test, while Kmt2d$^{+/+}$ did show an increase in activity compared to Kmt2d$^{+/\beta Geo}$ when both were treated with the ketogenic diet (FIG. 35A). Additionally, there were no differences for grip strength for either genotype or treatment. Similar to the open field test, Kmt2d$^{+/\beta Geo}$ did not show a significant difference from Kmt2d$^{+/+}$ on the regular diet, and did not decrease activity on MKD on the open field test, while Kmt2d$^{+/+}$ did show an increase in activity compared to Kmt2d$^{+/\beta Geo}$ when both were treated with the ketogenic diet (FIG. 35B). *$P<0.05$; ††$P<0.001$; and FIG. 36A, FIG. 36B, FIG. 36C, and FIG. 36D show the effects of exogenous BHB administration. BHB was injected at several difference doses (0, 5, 10, 20 mM/KG) and urine was taken after 1.5 hours. 10 mM/kg seemed to show a BHB level in the urine most similar to treatment with a ketogenic diet and was selected for further studies (FIG. 36A). After a two-week treatment with a once daily injection of 10 mM/kg IP injection of BHB with subsequent EdU injection for proliferation, a significant increase in EdU positive cells was seen in Kmt2d$^{+/\beta Geo}$ injected with a saline vehicle compared to Kmt2d$^{+/\beta Geo}$ injected with BHB (FIG. 36B). However, this treatment did not lead to a full recovery when compared to Kmt2d$^{+/+}$ injected with BHB. DCX IF staining (green) from the same treatment group showed similar results in that a significant increase in DCX positive cells was seen in Kmt2d$^{+/\beta Geo}$ injected with a saline vehicle compared to Kmt2d$^{+/\beta Geo}$ injected with BHB (FIG. 36C). Again, this treatment did not lead to a full recovery as compared to Kmt2d$^{+/+}$ injected with BHB. Urine taken at different time points throughout a 12 hour day from mice on a ketogenic diet, mice treated with 10 mM/kg BHB at 9 AM or saline vehicle at 9 AM, shows that while the one injection of BHB raised BHB levels in the urine to levels comparable to what was seen for MKD for a short period, this decreased to vehicle injected levels over a matter of hours so the total exposure to BHB was much less than for MKD (FIG. 36D). *$P<0.05$; ** $P<0.01$; †$P<0.005$; ††$P<0.001$.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Methods of Treating Mendelian Disorders of the Epigenetic Machinery

The presently disclosed subject matter provides a method of treating a Mendelian disorder of the epigenetic machinery in a subject in need thereof, the method comprising administering a therapeutically effective amount of an agent that restores balance between open and closed chromatin states at one or more target genes is an agent that ameliorates the effect of a defective gene encoding a component of the epigenetic machinery. In particular, the presently disclosed subject matter relates to the discovery that a reversible deficiency of postnatal neurogenesis in the granule cell layer of the dentate gyrus associated with intellectual disability in KS can be ameliorated postnatally by agents that favor open chromatin states. The term "open chromatin states" is used herein since the agent used is a histone deacetylase inhibitor expected to lead to an increase in histone acetylation, a histone modification exclusively seen in open chromatin. For example, as described elsewhere herein, treatment with a histone deacetylase inhibitor (AR-42) rescued postnatal neurogenesis in the granule cell layer of the dentate gyrus even though the epigenetic defect in mouse model of KS has to do with histone methylation system (a deficiency of H3K4me3 mark, see FIG. 5D). H3K4me3, like histone acetylation, is an open chromatin mark. Therefore, these results showed that one epigenetic modification can be targeted (histone acetylation) to make up for a deficiency in another epigenetic modification (histone methylation). In addition, these results showed that balancing the chromatin states of target genes, either by favoring open chromatin in diseases with a defect in epigenetic component leading to increased closed chromatin (see KS in FIG. 3) or favoring closed chromatin in disease with too much open chromatin (see BDMR in FIG. 3) offers a generalized treatment strategy for this group of disorders—the Mendelian disorders of the histone machinery.

In addition, the presently disclosed subject matter provides a method of treating a subject in need of therapy for a Mendelian disorder of the epigenetic machinery, comprising administering to the subject a ketogenic composition in an amount sufficient to produce a physiologically acceptable ketosis in the subject. For example, it has been found that a ketogenic diet or exogenous administration of an agent that promotes chromatin opening, e.g., a histone deacetylase inhibitor, e.g., beta-hydroxybutyrate (BHB), is an effective therapeutic approach for Kabuki syndrome and other related disorders of the histone machinery.

A. Balance Between Open and Closed Chromatin States

The DNA methylation machinery and the histone machinery affect the expression of many genes in trans (Berdasco & Esteller (2013) *Hum. Genet.* 132:359-83; Wolffe (1994) *Trends Biochem. Sci.* 19:240-44). Within this group, genetic mutations may occur in writers, erasers, or readers of epigenetic marks. The writers of epigenetic marks, which can be conceptualized as a set of highlighters, place the appropriate modifications on particular regions of the genome based on the cell type, developmental stage, and metabolic state of the cell. These marks "highlight" individual regions for use or disuse depending on whether the mark favors a more open or more closed chromatin state (FIG. 1). The erasers of epigenetic marks remove these same marks, favoring the opposite chromatin states (FIG. 1). The readers of epigenetic marks recognize and interpret particular marks locally and give cells a mechanism for keeping track of the overall chromatin state (FIG. 1).

Components of the epigenetic machinery are shown in FIG. 1. This machinery consists of writers (highlighters) and erasers of marks (for example, trimethylation of lysine 4 on histone H3 (H3K4me3)) as well as readers of those marks. A net balance between systems that remove and add a particular mark must be achieved. In many ways, the interacting epigenetic systems have certain distinct aspects that make them powerful final integrators of cellular signals (Jaenisch and Bird (2003) *Nat. Genet.* 33(Suppl.):245-545). For instance, many of the marks placed/removed by writers/erasers can directly affect gene expression, either in a permissive (H3K4me3, shown) or nonpermissive (H3K9me3, not shown) manner. This change in expression, presumably of multiple genes, has the potential to form feedback loops by affecting the amount and availability of the modification in question. Various internal metabolites can directly affect the prevalence of marks. For instance, S-adenosyl-methionine (SAM) is a donor for methylation reactions, including both DNA and histone methylation. Use of critical metabolic intermediates like SAM as donors for histone tail modifications or for DNA methylation allows environmental influences to impact and be integrated into the system and to potentially affect gene expression directly (Lu and Thompson (2012) *Cell Metab.* 16:9-177).

To ensure appropriate cell type-specific gene expression, a balance must be achieved between the activity of the two opposing systems (writers and erasers) and the subsequent placement of their respective marks (FIG. 1), ensuring that the appropriate composition of chromatin is present at particular gene promoters. Although a steady-state balance of chromatin marks is likely achieved at any given time, the opposing histone systems are likely to be dynamic in nature (Ficz et al. (2005) *Development* 132:3963-76; Mito et al. (2007) *Science* 315:1408-11), allowing the cell to rapidly respond to changes in environmental signals by altering gene expression at specific loci. The histone machinery (as well as some components of the DNA methylation machinery) is enormously redundant, perhaps reflecting the critical importance of maintaining this balance in many different cell types (FIG. 1).

Multiple lines of evidence suggest that Mendelian disorders of the epigenetic machinery result from perturbations of a delicate balance between open and closed chromatin states at one or more target genes is an agent that ameliorates the effect of a defective gene encoding a component of the epigenetic machinery. Many of these conditions can result from both point mutations within a gene and chromosome microdeletions containing the same gene, suggesting haploinsufficiency as a common disease mechanism (e.g., Breuning et al. (1993) *Am. J. Hum. Genet.* 52:249-54; Kleefstra et al. (2006) *Am. J. Hum. Genet.* 79:370-77; Kurotaki et al. (2002) *Nat. Genet.* 30:365-66; Lederer et al. (2012) *Am. J. Hum. Genet.* 90:119-24). The majority of the writer/eraser systems, which are composed of enzymes that either add or remove chromatin modifications, demonstrate autosomal dominant inheritance (see Table 1). This is intriguing because, in contrast, the majority of other Mendelian enzyme deficiencies are autosomal recessive conditions. Given the prolific efficacy of most enzymes, biallelic mutations with concomitant reduction of enzymatic activity to <5% of control levels are necessary to cause the expression of disease phenotypes; heterozygotes retaining approximately 50% of enzymatic activity are typically asymptomatic.

TABLE 1

Mendelian disorders of the epigenetic machinery.

| Epigenetic function | Gene | Gene function | Disease | Inheritance pattern |
|---|---|---|---|---|
| *Disorders of the DNA methylation machinery* | | | | |
| Writer | DNMT1 | DNA methyltransferase | Hereditary sensory and autonomic neuropathy with dementia and hearing loss (HSAN1E) | AD |
| | | | Autosomal dominant cerebellar ataxia, deafness, and narcolepsy (ADCADN) | AD |
| | DNMT3b | DNA methyltransferase | Immunodeficiency, centromeric instability, and facial anomalies syndrome (ICF) | AR |
| Reader | MeCP2 | Methyl-CpG binding protein | Rett syndrome | XL |
| | MBD5 | Methyl-CpG binding protein | 2q23.1 microdeletion/microduplication syndrome | AD |
| *Disorders of the histone machinery* | | | | |
| Writer | CREBBP | Histone acetyltransferase | Rubinstein-Taybi syndrome (RTS) | AD |
| | EP300 | Histone acetyltransferase | Rubinstein-Taybi syndrome (RTS) | AD |
| | KAT6B | Histone acetyltransferase | Genitopatellar syndrome (GPS) | AR |
| | | | Say-Barber-Biesecker-Young-Simpson syndrome (SBBYS) | AD |
| | KMT2D (or MLL2) | Histone methyltransferase (H3K4) | Kabuki syndrome (KS) | AD |
| | MLL | Histone methyltransferase (H3K4) | Wiedemann-Steiner syndrome (WSS) | AD |
| | EHMT1 | Histone methyltransferase (H3K9) | Kleefstra syndrome (KLFS) | AD |
| | EZH2 | Histone methyltransferase (H3K27) | Weaver syndrome (WS) | AD |
| | NSD1 | Histone methyltransferase (H3K36, H4K20) | Sotos syndrome (SS) | AD |
| Eraser | HDAC4 | Histone deacetylase | Brachydactyly-mental retardation syndrome (BDMR) | AD |
| | HDAC8 | Histone deacetylase | Cornelia de Lange syndrome 5 (CDLS5) | XL |
| | | | Wilson-Turner syndrome (WTS) | XL |
| | KDM5C* | Histone demethylase (H3K4) | Claes-Jensen syndrome (CJS) | XL |
| | KDM6A* | Histone demethylase (H3K27) | Kabuki syndrome (KS) | XL |
| | PHF8** | Plant homeodomain finger protein | Siderius X-linked mental retardation syndrome (MRXSSD) | XL |
| Reader | PHF6 | Plant homeodomain finger protein | Borjeson-Forssman-Lehmann syndrome (BFLS) | XL |
| | BRWD3 | Bromodomain-containing protein | X-linked mental retardation and macrocephaly | XL |

*Indicates genes known to escape X-inactivation.
**Indicates gene encoding a component of the epigenetic machinery that functions as both an eraser and a reader.
Abbreviations:
AD, autosomal dominant;
AR, autosomal recessive;
XL, X linked.

The dosage sensitivity for Mendelian disorders of the epigenetic machinery is intriguing in light of the enormous redundancy of some of the protein components with apparently overlapping functions. For instance, there are dozens of enzymes described with H3K4me3 activity, many of which are ubiquitously expressed (Eissenberg & Shilatifard (2010) *Dev. Biol.* 339:240-49). Despite this seemingly evident redundancy, loss of a single allele of one of these enzymes is sufficient to cause the multisystem disease KS. However, without being bound by theory, perhaps this redundancy limits the number of affected cell-types and thereby leads to a more benign phenotype that is compatible with life despite the wide expression of this component of the epigenetic machinery. Although alternative explanations exist for dosage sensitivity in humans, and without being bound by theory, one hypothesis is that the total activity of writers and erasers, the epigenetic marks that they place, and thus the resulting open (active) and closed (silent) chromatin states, must remain tightly balanced in cells at particular gene promoters (FIG. 1). The dosage sensitivity of components of the epigenetic machinery could suggest that levels of coactivators are carefully controlled in cells to fine-tune gene expression levels. For instance, cellular systems with CREBBP deficiency reveal dose-dependent effects on gene expression, which are dependent on the diversity of modification systems available for a particular target site and/or the strength of recruitment to a particular site (Kasper et al. (2010) *EMBO J*. 29:3660-72). Alternatively, given that each individual epigenetic player within a cell acts on multiple downstream target genes and genomic regions and that each works in close cooperation with transcription factors, which are also known to be finely titrated, disruption of just one allele of one of these genes is sufficient to alter this delicate balance.

A balance hypothesis is supported by the observation that KS exhibits identical phenotypes upon disruption of either a writer of H3K4me3 (an active mark) or an eraser of H3K27me3 (a silencing mark). This indicates that the transition between open and closed chromatin states is critical to disease pathogenesis. Similarly, defects in either deposition of histone acetylation (RTS) or removal of histone acetylation marks (BDMR) lead to disease phenotypes. A one-sided deficiency might be expected to have genome-wide effects, but perhaps similarly to ATRX, there are a limited number of disease-relevant target genes that are particularly sensitive in each case. At target gene promoters in cells haploinsufficient for MLL2, for example, one might expect to see decreased H3K4me3 and thus increased H3K4me0. Although most genes might tolerate this deficiency, perhaps a small number of disease-relevant target genes in key cell populations are critically affected by this disrupted balance, resulting in altered gene expression. Alternatively, this might promote placement of other marks—possibly H3K9me3, DNA methylation, and H3K27me3—which also could affect transcription.

A number of Mendelian disorders of the epigenetic machinery are known to involve disruption of histone writers and erasers (See Table 1). If the delicate balance of histone marks and the subsequent effects on the predisposition toward open or closed chromatin states are central to pathogenesis, then it might be critical to determine whether the effect of disruption of each component of the epigenetic machinery would be expected to lead to a defect in open chromatin (likely leading to downregulation of gene expression) or a defect of closed chromatin (likely leading to upregulation of gene expression) at downstream target genes. FIG. 2 categorizes disorders based on expected effects on chromatin states.

Furthermore, the hypothesis that a delicate balance of chromatin marks and target gene expression is important in the pathogenesis of Mendelian disorders of the epigenetic machinery is not limited to the histone modification system. Disruption of a dosage-sensitive reader of epigenetic marks, MBD5, can lead to similar phenotypic differences if MBD5 is deleted or duplicated. Indeed, MBD5 expression is reduced in individuals with haploinsufficiency of the predicted reader of epigenetic marks, regardless of mutation mechanism (Talkowski et al. (2011) *Am. J. Hum. Genet*. 89:551-63), and MBD5 expression is increased when the region is duplicated (Mullegama et al. (2014) *Eur. J. Hum. Genet*. 22:57-63). However, downstream epigenetic and cellular consequences and particular target loci have not been identified. Similarly, a protein closely related to MBD5 and a known reader of DNA cytosine methylation, MeCP2, exhibits marked dosage sensitivity, which is illustrated nicely by the varying phenotypic severity of the corresponding X-linked disorder. Rett syndrome, based on the number of copies of the MeCP2 gene expressed (Guy et al. (2011) *Annu. Rev. Cell Dev. Biol*. 27:631-52). The disorder is more severe in males, who have no functional copies of the gene; for females, the phenotype can vary greatly depending on the pattern of X inactivation, as well as on the type and severity of mutation. The more skewed the X inactivation pattern is toward the normal X, the less severe the disease phenotype (Guy et al. (2011) *Annu. Rev. Cell Dev. Biol*. 27:631-52). That both MeCP2 and MBD5, two readers of epigenetic marks, appear to be so exquisitely dosage sensitive suggests the importance of maintaining not only a critical balance of epigenetic marks and chromatin states within cells but also a critical number of interpreters of those marks. Furthermore, the phenotypic findings in these disorders along with the distinct neurobehavioral-predominant pathogenic features of each suggest that this balance is particularly delicate within the central nervous system.

It was hypothesized that observed gene dosage sensitivity in KS involved a relative imbalance between open and closed chromatin states for critical target genes. If this was the case, it was hypothesized that this balance could be restored with drugs that promote open chromatin states, such as a histone deacetylase inhibitor (HDACi). The presently disclosed subject matter relates to the discovery that a reversible deficiency of postnatal neurogenesis in the granule cell layer of the dentate gyrus associated with intellectual disability in KS can be ameliorated postnatally by agents that favor open chromatin states, as described more fully in the Examples below.

B. Mendelian Disorders of the Epigenetic Machinery

Selected Mendelian disorders of the histone machinery caused by alterations of writers (highlighters) and erasers are shown in FIG. 2. Acetylation is a binary mark (present or not), and histone lysine methylation a quaternary mark (present as mono-, di-, tri-, or unmethylated). The diagram illustrates these two types of modifications on two of the N-terminal histone tails, histone H3 and histone H4. The writers (highlighters) and erasers place and remove the modifications; some of these are associated with open, permissive chromatin (FIG. 2, green), and others are associated with closed, repressive chromatin (FIG. 2, red). Based on the enzymatic component of the epigenetic machinery involved and the predicted consequence of the reported mutations for each disorder, the diagram shows conditions that would be expected to shift the balance toward closed chromatin states at target loci (FIG. 2, top) and conditions that would be expected to shift the balance toward open chromatin states at target loci (FIG. 2, bottom). The former category includes Rubinstein-Taybi syndrome (RTS) (Petrij et al. (1995) *Nature* 376:348-5192; Roelfsema et al. (2005) *Am. J. Hum. Genet*. 76:572-80), Kabuki syndrome (KS) (Lederer et al. (2012) *Am. J. Hum. Genet*. 90:119-24; Ng et al. (2010) *Nat. Genet*. 42:790-93), Wiedemann-Steiner syndrome (WSS) (Jones et al. (2012) *Am. J. Hum. Genet*. 91:358-64), and possibly Weaver syndrome (WS) and Sotos syndrome (SS) (Gibson et al. (2012) *Am. J. Hum. Genet*. 90:110-18; Tatton-Brown et al. (2011) *Oncotarget* 2:1127-33; Kurotaki et al. (2002) *Nat. Genet*. 30:365-66); the latter category includes brachydactyly-mental retardation syndrome (BDMR) (Williams et al. (2010) *Am. J. Hum. Genet.* 87:219-28), Kleefstra syndrome (KLFS) (Kleefstra et al. (2006) *Am. J. Hum. Genet.* 79:370-776), Claes-Jensen syndrome (CJS) (Jensen et al. (2005). *Am. J. Hum. Genet.* 76:227-366), and Sotos syndrome (SS) (Kurotaki et al. (2002) *Nat. Genet.* 30:365-666). In some embodiments, the Mendelian disorder of the epigenetic machinery is not epilepsy. In some embodiments, the Mendelian disorder of the epigenetic machinery is not a convulsive encephalopathy. In some embodiments, the Mendelian disorder of the epigenetic machinery is not neural degeneration produced by traumatic brain injury, cerebral ischemia, or hypoglycemia. In some embodiments, the Mendelian disorder of the epigenetic machinery is not amyotrophic lateral sclerosis. In some embodiments, the Mendelian disorder of the epigenetic machinery is not Alzheimer's disease. In some embodiments, the Mendelian disorder of the epigenetic machinery is not Parkinson's disease. In some embodiments, the Mendelian disorder of the epigenetic machinery is not Lewy body dementia. In some embodiments, the Mendelian disorder of the epigenetic machinery is not Huntington's disease.

Accordingly, in some embodiments of the methods of the presently disclosed subject matter for treating a Mendelian disorder of the epigenetic machinery in a subject in need thereof, the defective gene encoding a component of the epigenetic machinery encodes a histone methyltransferase and the Mendelian disorder of the epigenetic machinery is selected from the group consisting of Kabuki syndrome (KS), Wiedemann-Steiner syndrome (WSS), Kleefstra syndrome (KLFS), Weaver syndrome (WS), and Sotos syndrome (SS). In still further embodiments, where the Mendelian disorder of the epigenetic machinery is KS, the defective gene encoding a component of the epigenetic machinery is KMT2D.

KS, which can be caused by a defect in either a writer or an eraser (FIG. 2). KS is an autosomal dominant or X-linked intellectual disability syndrome with specific dysmorphic features, including a flattened facial appearance with characteristic eyes exhibiting long palpebral fissures, eversion of the lower lids, highly arched eyebrows, and long eyelashes, as well as short stature.

KS is caused by heterozygous loss-of-function mutations in either of two genes with complementary functions, lysine-specific methyltransferase 2D (KMT2D) on human chromosome 12 (also known as mixed lineage leukemia 2 or MLL2; Ng et al. (2010) *Nat. Genet.* 42:790-3) or lysine-specific demethylase 6A (KDM6A) on human chromosome X (Lederer et al. (2012) *Am. J. Hum. Genet.* 90:119-24) (FIG. 2). KMT2D is a methyltransferase that adds a trimethylation mark to H3K4 (H3K4me3, an open chromatin mark) while KDM6A is a demethylase that removes trimethylation from histone 3 lysine 27 (H3K27me3, a closed chromatin mark). Both genes facilitate the opening of chromatin and promote gene expression (Ng et al. (2010) *Nat. Genet.* 42:790-3; Lederer et al. (2012) *Am. J. Hum. Genet.* 90:119-24; Miyake et al. (2013) *Hum. Mutat.* 34:108-10). These defects lead to indistinguishable conditions (KS1 and KS2).

It may seem counterintuitive that loss-of-function mutations in a writer and an eraser lead to similar phenotypes; however, this makes sense when the specific functions are examined KDM6A is a histone H3K4 methyltransferase that adds trimethylation to H3K4 (Issaeva et al. (2006) *Mol. Cell. Biol.* 27:1889-903), a mark exclusively seen in open chromatin (ENCODE Proj. Consort. (2007) *Nature* 447:799-816). KDM6A is a demethylase that removes trimethylation from H3K27, a closed chromatin mark (ENCODE Proj. Consort. (2007) *Nature* 447:799-816; Sengoku & Yokoyama (2011) *Genes Dev.* 25:2266-77). KDM6A is a transcriptional coactivator that interacts with transcriptional machinery at the promoters of target genes to facilitate gene expression (Issaeva et al. (2006) *Mol. Cell. Biol.* 27:1889-903). Decreased KDM6A (or KDM6A) levels would therefore be expected to interfere with the upregulation of numerous critical target genes in susceptible cell types. Interestingly, KDM6A is a Trithorax ortholog, but in *Drosophila* the opposing Trithorax/Polycomb systems are known to compete to establish a dynamic balance that determines the gene expression levels of particular target genes (Schwartz & Pirrotta (2008) *Curr. Opin. Cell Biol.* 20:266-73).

A novel mouse model of KS with deletion of the SET domain of KDM6A (KMT2D) was recently characterized that appears to have a significant deficiency of H3K4me3 in the granule cell layer of the dentate gyrus, which is associated with defective neurogenesis and hippocampal memory defects (see Experimental Section below). This work indicates that specific cell populations may have particular sensitivity to decreased levels of histone-modifying enzymes and the marks that they place. The fact that a deficiency in either removing a closed chromatin mark or placing an open chromatin mark leads to the same disease state suggests that the balance between systems that place open and closed chromatin marks at particular loci may be central to the pathogenesis of KS.

In another embodiment of the presently disclosed methods, the defective gene encoding a component of the epigenetic machinery encodes a histone deacetylase and the Mendelian disorder of the epigenetic machinery is selected from the group consisting of Brachydactylymental retardation syndrome (BDMR), Cornelia de Lange syndrome 5 (CDLS5), and Wilson-Turner syndrome (WTS). In still further embodiments, where the Mendelian disorder of the epigenetic machinery is BDMR, the defective gene encoding a component of the epigenetic machinery is HDAC4.

Brachydactyly-mental retardation syndrome (BDMR) provides an example of the opposite scenario: a disorder whose molecular abnormality tips the balance toward open chromatin at target loci (Williams et al. (2010) *Am. J. Hum. Genet.* 87:219-2) (FIG. 2). In this condition, caused by haploinsufficiency of a histone deacetylase gene (HDAC4), patients have skeletal abnormalities, including brachycephaly and brachydactyly, as well as intellectual disability (Williams et al. (2010) *Am. J. Hum. Genet.* 87:219-2). This condition also demonstrates dosage sensitivity, as the severity of the phenotype appears to be dictated by the amount of residual function of HDAC4 (Morris et al. (2012) *Am. J. Med. Genet. A* 158A:2015-20). HDAC4 is an eraser of the same marks deposited by CREBBP/EP300 (Wang et al. (1999) *Mol. Cell. Biol.* 19:7816-27), tilting the balance toward closed chromatin states. For instance, decreased amounts of HDAC4 appear to upregulate the MEF2 gene in neurons, a possible explanation for the intellectual disability seen in the syndrome (Ronan et al. (2013) *Nat. Rev. Genet.* 14:347-59). In addition, HDAC$^{-/-}$ mice have skeletal abnormalities resembling those of humans with BDMR, as well as increased expression of RUNX2, a known target of HDAC4 repression (Vega et al. (2004) *Cell* 119:555-66). Therefore, either too much or too little open chromatin at target genes can lead to disease, indicating that the balance between open and closed chromatin states at those sites must be tightly regulated.

In another embodiment of the presently disclosed methods, the defective gene encoding a component of the epigenetic machinery encodes a histone acetyltransferase and the Mendelian disorder of the epigenetic machinery is selected from the group consisting of Rubinstein-Taybi syndrome (RTS), Genitopatellar syndrome (GPS), and Say-Barber-Biesecker-Young-Simpson syndrome (SBBYS).

Rubinstein-Taybi syndrome (RTS), is inherited in an autosomal dominant manner and is characterized by specific dysmorphic features, including talon cusps, broad thumbs and great toes with angulation, a grimacing smile, short stature, and intellectual disability (Petrij et al. (1995) *Nature* 376:348-51; Roelfsema et al. (2005) *Am. J. Hum. Genet.* 76:572-80). The condition is caused by haploinsufficiency of either of two histone acetyltransferase enzyme genes (CREBBP and EP300) (Petrij et al. (1995) *Nature* 376:348-51; Roelfsema et al. (2005) *Am. J. Hum. Genet.* 76:572-80), which have overlapping functions (Bannister & Kouzarides (1996) *Nature* 384:641-43; Ogryzko et al. (1996) *Cell* 87:953-59) (FIG. 2). RTS is therefore a deficiency of two different writers, both targeting critical sites on histone tails and leading to the same phenotype. Histone acetylation is a binary mark (present or not) and is seen exclusively in open chromatin. The fact that a defect in either CREBBP or EP300 leads to highly overlapping phenotypes might indicate that both histone acetyltransferases are targeted to an overlapping set of genes. Lymphoblastic cell lines from patients with mutations in CREBBP demonstrate global deficiency of histone acetylation (Lopez-Atalaya et al. (2012) *J. Med. Genet.* 49:66-74), and mouse models with targeted CREBBP alleles have demonstrated hippocampal memory defects associated with reduced histone acetylation (Alarcón et al. (2004) *Neuron* 42:947-59; Korzus et al. (2004) *Neuron* 42:961-72; Valor et al. (2011) *J. Neurosci.* 31:1652-63). A deficiency of histone acetylation might lead to a deficiency of open chromatin states in critical cell populations, with correspondingly lowered levels of target gene expression. Although both KS and RTS might be expected to tilt the balance toward less open chromatin states, the phenotypes are quite different. This probably reflects different target gene specificities for the KDM6A/KDM6A (Guo et al. (2012) *Proc. Natl. Acad. Sci. USA* 109:17603-8) and CREBBP/EP300 (Wood et al. (2006) *Learn. Mem.* 13:609-17) systems.

In another embodiment of the presently disclosed methods, the defective gene encoding a component of the epigenetic machinery encodes a plant homeodomain finger protein and the Mendelian disorder of the epigenetic machinery is selected from the group consisting of Siderius X-linked mental retardation syndrome (MRXSSD) and Borjeson-Forssman-Lehmann syndrome (BFLS).

Although the deposition of epigenetic modifications can directly affect expression, reading of those marks must also be important to coordinate members of the epigenetic machinery (Portela & Esteller (2010) *Nat. Biotechnol.* 28:1057-68), link chromatin-modifying systems to other systems (Yun et al. (2011) *Cell Res.* 21:564-78), and ultimately affect downstream gene expression. In that regard, some readers contain distinct domains that confer the ability to place histone modifications (writers) or remodel chromatin (Qiu et al. (2010) *Cell Res.* 20:908-18). Borjeson-Forssman-Lehmann syndrome (BFLS), however, is an X-linked recessive intellectual disability syndrome caused by missense mutations in PHF6, encoding a protein that appears to be a reader without other functional domains (Lower et al. (2002) *Nat. Genet.* 32:661-65), although PHF6 is known to bind to the NuRD complex (Denslow & Wade (2007) *Oncogene* 26:5433-38; Todd & Picketts (2012) *J. Proteome Res.* 11:4326-37) and may help to lock in repression through this interaction. BFLS patients have intellectual disability, dysmorphic features, and obesity (Turner et al. (1989) *Am. J. Med. Genet.* 34:463-69). Loss-of-function mutations in the same gene have also been found in a number of leukemias (Todd & Picketts (2012) *J. Proteome Res.* 11:4326-37).

In another embodiment of the presently disclosed methods, the defective gene encoding a component of the epigenetic machinery encodes a histone demethylase and the Mendelian disorder of the epigenetic machinery is selected from the group consisting of Claes-Jensen syndrome (CJS) and KS.

In another embodiment of the presently disclosed methods, the defective gene encoding a component of the epigenetic machinery encodes a DNA methyltransferase and the Mendelian disorder of the epigenetic machinery is selected from the group consisting of Hereditary sensory and autonomic neuropathy with dementia and hearing loss (HSAN1E), Autosomal dominant cerebellar ataxia, deafness, and narcolepsy (ADCADN), and Immunodeficiency, centromeric instability, and facial anomalies syndrome (ICF).

In another embodiment of the presently disclosed methods, the defective gene encoding a component of the epigenetic machinery encodes a Bromodomain-containing protein and the Mendelian disorder of the epigenetic machinery is X-linked mental retardation and macrocephaly.

C. Treatment Methods for Mendelian Disorders

In some embodiments, the presently disclosed subject matter provides a method of treating a subject in need of therapy for a Mendelian disorder of the epigenetic machinery, comprising administering to the subject a ketogenic composition in an amount sufficient to produce a physiologically acceptable ketosis in the subject.

In some embodiments, "physiologically acceptable ketosis" is characterized by β-hydroxybutyrate blood levels of between 0.5 and 10 mM. In some embodiments, the total concentration of (R)-3-hydroxybutyrate in the blood is raised to between 1 and 6 mM (Pfeifer H H, Thiele E A. Low-glycemic-index treatment: a liberalized ketogenic diet for treatment of intractable epilepsy. Neurology. 2005 Dec. 13; 65(11):1810-2). In some embodiments, the urinary excretion level of β-hydroxybutyrate in a subject with a physiologically acceptable ketosis is from about 5 to about 200 mg/dL.

In some embodiments, a "ketogenic composition" comprises a ketogenic diet.

Generally, a ketogenic diet is a high lipid, low carbohydrate date that results in increased blood ketones in a subject on the diet. In some embodiments, the ketogenic diet comprises a diet in which about 2% to about 15% by weight of its caloric content is carbohydrates, about 60% to about 90% by weight of its caloric content is fat, and about 8% to about 30% by weight of its caloric content is protein. In some embodiments, the ketogenic diet comprises a diet in which about 2% to about 4% by weight of its caloric content is carbohydrates, about 87% to about 90% by weight of its caloric content is fat, and less than or equal to about 8% by weight of its caloric content is protein.

In some embodiments, the ketogenic composition comprises a nutritionally balanced ketogenic diet. As used herein, a "nutritionally balanced" ketogenic diet refers to a ketogenic diet in which protein intake is increased as compared to a ketogenic diet to avoid amino acid nutritional deficiency that may ensue during administration of the ketogenic diet. In some embodiments, the nutritionally balanced ketogenic diet comprises a diet in which about 2% to about 15% by weight of its caloric content is carbohydrates, about 60% to about 90% by weight of its caloric content is fat, and about 8% to about 30% by weight of its caloric content is protein. In some embodiments, the nutritionally balanced ketogenic diet comprises a diet in which about 1% by weight of its caloric content is carbohydrates, about 90% by weight of its caloric content is fat, and about 9% by weight of its caloric content is protein. In some embodiments, the nutritionally balanced ketogenic diet comprises a 4:1 ratio of caloric fat content to caloric protein content.

In some embodiments, the ketogenic composition comprises any compound or formulation that produces a physiologically acceptable ketosis in a subject. For example, the ketogenic composition may be a food supplement, such as drinking water, beverage, liquid concentrate, gel, yogurt, powder, granule, paste, suspension, chew, morsel, treat, snack, pellet, pill, capsule, tablet, or any other delivery form. In some embodiments, the ketogenic composition can comprise a ready-to-drink beverage, powdered beverage formulation, nutritional or dietary supplement selected from the group consisting of gelatin capsule or tablet, suspension, parenteral solution, or a food product formulated for human consumption. In some embodiments, the ketogenic composition comprises an infant formula, e.g., for treatment of a postnatal human subject that has or is suspected of having a Mendelian disorder of the epigenetic machinery (e.g., Kabuki syndrome). In some embodiments, the ketogenic composition may require admixing with water or the like prior to administration to the subject, for example to adjust the dose, to make it more palatable, or to allow for more frequent administration in smaller doses.

Ketogenic compounds generally enhance endogenous fat metabolism (oxidation) by the recipient and thereby raise the blood ketone levels, and include, for example, C3-8 ketones such as acetone, D-β-hydroxybutyrate, metabolic precursors of D-β-hydroxybutyrate (for example, acetoacetyl precursors such as acetoacetyl-1,3-butanediol, 1,3-butanediol, acetoacetyl-D-β-hydroxybutyrate and acetoacetylglycerol; esters such as esters of D-β-hydroxybutyrate with monohydric, dihydric or trihydric alcohols; or polyesters of D-β-hydroxybutyrate such as poly-D-β-hydroxybutyrate or terminally oxidised poly-D-β-hydroxybutyrate having from about 2 to about 100 repeats, e.g. from about 3 to about 10 repeats); R,S-1,3-butanediol acetoacetate diester (D'Agostino D P et al. Therapeutic ketosis with ketone ester delays central nervous system oxygen toxicity seizures in rats. Am J Physiol Regul Integr Comp Physiol. 2013 May 15; 304(10); glycerol esters of acetoacetate and D-β-hydroxybutyrate (Hashim S A, Vanitallie T B. Ketone body therapy: from the ketogenic diet to the oral administration of ketone ester. J Lipid Res. 2014 September; 55(9):1818-26); medium chain triglycerides (MCTs) (Huttenlocher P R, Wilbourn A J, Signore J M. Medium-chaintriglycerides as a therapy for intractable childhood epilepsy. Neurology (1971) 21:1097-103); metabolic precursors of acetoacetate, or any combination thereof.

In some embodiments, the ketogenic composition comprises at least one ketogenic compound selected from the group consisting of: i) a ketogenic amino acid selected from the group consisting of isoleucine, leucine, tryptophan, lysine, phenylalanine, tyrosine, aspartate β-semialdehyde, β-aspartylphosphate, saccharopine, α-aminoadipate δ-semialdehyde, and α-aminoadipate; ii) an immediate precursor of a ketogenic amino acid selected from the group consisting of α-ketoglutarate, indole, α-ketobutarate, L-histadinol, phenylpyruvate, 4-hydroxyphenylpyruvate, methyltetrahydrofolate, α-keto-β-methylvalerate, and α-ketoisovalerate; iii) an amino acid increasing molecule selected from the group consisting of a glutamate dehydrogenase, a valine aminotransferase, an arginosuccinate lyase, a tyrosine transaminase, an aromatic amino acid transaminase, a tryptophan synthase, and a histidinol dehydrogenase; iv) a medium chain triglyceride; and v) combinations thereof.

As used herein, an "amino acid" refers to a chemical compound having amino and carboxylate functional groups covalently bound to the same carbon. As used herein, a "ketogenic amino acid" is an amino acid that gives rise to acetyl-CoA or acetoacetyl-CoA. Nonlimiting examples ketogenic amino acids include isoleucine, leucine, threonine, tryptophan, lysine, phenylalanine, tyrosine, aspartate β-semialdehyde, β-aspartylphosphate, saccharopine, α-aminoadipate δ-semialdehyde, and α-aminoadipate.

In some embodiments, the ketogenic composition comprises at least one agent that promotes open chromatin states at one or more target genes in the subject. The target gene can be any gene that is involved in a Mendelian disorder of the epigenetic machinery. For example, the target gene may be a developmental gene which may be aberrantly regulated when there is an aberrant chromatin state at the gene. In some embodiments, the agent decreases the level and/or activity of a histone deacetylase protein in the subject. In some embodiments, the agent decreases the level and/or activity of histone deacetylase 1 (HDAC1). In some embodiments, the agent decreases the level and/or activity of histone deacetylase 3 (HDAC3). In some embodiments, the agent decreases the level and/or activity of histone deacetylase 4 (HDAC4). In some embodiments, the agent decreases the level and/or activity of histone deacetylase 6 (HDAC6). In some embodiments, the agent decreases the level and/or activity selected from the group consisting of HDAC1, HDAC3, HDAC4 and HDAC6. In some embodiments, the agent decreases the level and/or activity of at least two HDACs selected from the group consisting of HDAC1, HDAC3, HDAC4 and HDAC6. In some embodiments, the agent decreases the level and/or activity of at least three HDACs selected from the group consisting of HDAC1, HDAC3, HDAC4 and HDAC6. In some embodiments, the agent decreases the level and/or activity of HDAC1, HDAC3, HDAC4 and HDAC6.

In other embodiments, the ketogenic composition comprises at least one agent that decrease the level and/or activity of a NAD+ dependent deacetylase protein. In some embodiments, the NAD+ dependent deacetylase protein is selected from the group consisting of SIRT1, SIRT2, SIRT3, SIRT4, SIRT5, SIRT6, and SIRT7. In some embodiments, the NAD+ dependent deacetylase protein is SIRT1. In some embodiments, the NAD+ dependent deacetylase protein is SIRT2. In some embodiments, the NAD+ dependent deacetylase protein is SIRT2. In some embodiments, the NAD+ dependent deacetylase protein is SIRT3. In some embodiments, the NAD+ dependent deacetylase protein is SIRT4. In some embodiments, the NAD+ dependent deacetylase protein is SIRT5. In some embodiments, the NAD+ dependent deacetylase protein is SIRT6. In some embodiments, the NAD+ dependent deacetylase protein is SIRT7.

In some embodiments, the agent decreases deacetylation of and/or increases acetylation of lysine 4 of histone 3 in the subject. In some embodiments, the agent increases the level of H3K4me3. In some embodiments, the agent modulates the methylation of lysine 4 of histone 3 in the subject. In some embodiments, the agent increases the global methylation level of H3K4me3. In other embodiments, the agent decreases the global methylation level of H3K4me3.

In some embodiments, the presently disclosed subject matter also provides a method of instructing a subject in need of therapy for a Mendelian disorder of the epigenetic machinery by providing instructions to receive a treatment comprising a ketogenic composition in an amount sufficient to produce a physiologically acceptable ketosis in the subject. The term "instructing" a patient as used herein means providing directions for applicable therapy, medication, treatment, treatment regimens, and the like, by any means, but preferably in writing. Instructing can be in the form of prescribing a course of treatment, or can be in the form of package inserts or other written promotional material.

In some embodiments, the presently disclosed subject matter provides a method of promoting a treatment for a subject in need of therapy for a Mendelian disorder of the epigenetic machinery, wherein the treatment comprises a ketogenic composition in an amount sufficient to produce a physiologically acceptable ketosis when administered to a subject in need of therapy for a Mendelian disorder of the epigenetic machinery. The term "promoting" as used herein means offering, advertising, selling, or describing a particular drug, combination of drugs, or treatment modality, by any means, including writing, such as in the form of package inserts. Promoting herein refers to promotion of a ketogenic composition for an indication, such as the treatment of a Mendelian disorder of the epigenetic machinery, such as Kabuki syndrome, where such promoting is authorized by the Food and Drug Administration (FDA) as having been demonstrated to be associated with statistically significant therapeutic efficacy and acceptable safety in a population of subjects. In some embodiments, promoting is not authorized by the Food and Drug Administration (FDA) (or other health regulatory agency, such as the European Medicines Agency (EMA), and promoting is for an off-label use. In some embodiments, the package insert provides instructions to receive treatment with a ketogenic composition. In some embodiments, the promotion is by a package insert accompanying a formulation comprising the ketogenic composition. In some embodiments, the promotion is by written communication to a physician or health care provider. In some embodiments, the promotion is by oral communication to a physician or health care provider.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant an agent that restores balance between open and closed chromatin states at one or more target genes, as described elsewhere herein. In particular, the agent that restores balance between open and closed chromatin states at one or more target genes is an agent that ameliorates the effect of a defective gene encoding a component of the epigenetic machinery. As used herein, an agent that ameliorates the effect of a defective gene encoding a component of the epigenetic machinery may decrease, suppress, attenuate, diminish, arrest, or stabilize the effect of a defective gene encoding a component of the epigenetic machinery. In some contexts, "agent" refers to an agent that promotes open chromatin states at one or more target genes.

More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient.

The subject treated by the presently disclosed methods in their many embodiments is desirably a human subject, such as a postnatal human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments).

D. Agents that Restore Balance Between Open and Closed Chromatin States

Therapeutic approaches based on understanding and restoring the balance of chromatin states are shown in FIG. 3. If abnormalities of the expression of target genes are the culprit, the target genes would be expected to be fully functional, albeit improperly expressed, in patients with these disorders. For instance, Kabuki syndrome (KS) is related to a deficiency of trimethylation of lysine 4 on histone H3 (H3K4me3) or an inability to remove H3K27me3, marks that are predominantly seen in open and repressive chromatin, respectively (FIG. 28). If the pathophysiology of KS is related to an imbalance between open and closed chromatin states (FIG. 3, top left), with an inability to use critical gene transcripts, then this balance could be restored by inhibiting the transition to closed chromatin with a histone deacetylase (HDAC) inhibitor (FIG. 3, bottom left). In contrast, brachydactyly-mental retardation syndrome (BDMR) would be expected to lead to an overrepresentation of open chromatin states (FIG. 3, top right), with excessive transcription of disease-relevant target genes. Therefore, a histone acetyltransferase (HAT) inhibitor could be a useful therapeutic strategy (FIG. 3, bottom right).

Accordingly, in some embodiments of the methods of the presently disclosed subject matter for treating a Mendelian disorder of the epigenetic machinery in a subject in need thereof, the defective gene encoding a component of the epigenetic machinery encodes a histone methyltransferase and the agent that restores balance between open and closed chromatin states at the defective gene encoding a component of the epigenetic machinery is a histone deacetylase inhibitor (HDACi).

HDACi compounds induce hyperacetylation of histones that modulate chromatin structure and gene expression. These inhibitors also induce growth arrest, cell differentiation, and apoptosis of tumor cells. Recently it was reported that HDACi can restore the expression of functional ERα to ER-breast cancer cells (Sharma et al: (2006) Cancer Res. 66:6370-8; Yang et al. (2000) Cancer Res. 60:6890-4: Keen et al. (2003) Breast Cancer Res. Treat. 81:177-86). The discovery of recruitment of histone deacetylase (HDAC) enzymes in cancer has provided a rationale for using inhibition of HDAC activity to release transcriptional repression as viable option toward achieving eventual therapeutic benefit (Vigushin et al. (2002) Anticancer Drugs 13:1-13). HDACi compounds block deacetylation function, causing cell cycle arrest, differentiation, and/or apoptosis of many tumors (Vigushin et al. (2002) Anticancer Drugs 13:1-13). Silencing of genes that affect growth and differentiation has been shown to occur by aberrant DNA methylation in promoter region and by changes in chromatin structure that involve histone deacetylation. Recent studies have established a link between oncogene-mediated suppression of transcription and recruitment of HDAC into nuclear complex. HDACi compounds such as butyric acid (BA), 4-phenylbutyric acid and trichostatin A reverse this suppression by specific inhibition of HDAC activity, leading to histone hyperacetylation, chromatin relaxation, and enhanced transcription.

The HDACs are a family including at least eighteen enzymes, grouped in three classes (Class I, II and III). Class I HDACs include, but are not limited to, HDACs 1, 2, 3, 8 and 11. Class I HDACs can be found in the nucleus and are believed to be involved with transcriptional control repressors. Class II HDACs include, but are not limited to, HDACs 4, 5, 6, 7, and 9 and can be found in both the cytoplasm as well as the nucleus. Class III HDACs are believed to be $NAD^+$ dependent proteins and include, but are not limited to, members of the Sirtuin family of proteins. Non-limiting examples of sirtuin proteins include SIRT1-7. As used herein, the term "selective HDAC" refers to an HDAC inhibitor that does not substantially interact with all three HDAC classes. The term "Class I Selective HDAC" refers to an HDAC inhibitor that does not substantially interact with Class II or Class III HDACs.

In some embodiments, at least one agent is a histone deacetylase inhibitor. In some embodiments, at least one agent is a Class I HDAC inhibitor e.g., a Class I selective HDAC inhibitor. In some embodiments, at least one agent is a Class II HDAC inhibitor, e.g., a Class II selective HDAC inhibitor. In some embodiments, at least one agent is a Class III HDAC inhibitor, e.g., a Class II selective HDAC inhibitor. In some embodiments, at least one agent is a HDAC1 inhibitor. In some embodiments, at least one agent is a HDAC2 inhibitor. In some embodiments, at least one agent is a HDAC3 inhibitor. In some embodiments, at least one agent is a HDAC4 inhibitor. In some embodiments, at least one agent is a HDAC5 inhibitor. In some embodiments, at least one agent is a HDAC6 inhibitor. In some embodiments, at least one agent is a HDAC7 inhibitor. In some embodiments, at least one agent is a HDAC8 inhibitor. In some embodiments, at least one agent is a HDAC9 inhibitor. In some embodiments, at least one agent is a HDAC11 inhibitor.

In some embodiments, at least one agent is D-β-hydroxybutyrate, a salt of D-β-hydroxybutyrate, a metabolic precursor of D-β-hydroxybutyrate, an ester or polyester of D-β-hydroxybutyrate, and combinations thereof. In some embodiments, at least one agent is a metabolic precursor or salt of D-β-hydroxybutyrate, including, but not limited to, sodium (R)-3-hydroxybutyrate, (R)-1,3-butandiol, acetoacetylbutandiol dimer and trimer D-β-hydroxybutyrate, acetoacetyl-tri-3-hydroxybutyrate, mid chain triglyceride, triolide, D-β-hydroxybutyrate-triglyceride, and D-β-hydroxybutyrate multimers.

In some embodiments, the HDACi is selected from the group consisting of: (S)—N-hydroxy-4-(3-methyl-2-phenylbutanamido)benzamide (AR-42); 2-Propylpentanoic acid (valproic acid); N'-hydroxy-N-phenyl-octanediamide (vorinostat); and 5H-dibenz[b,f ]azepine-5-carboxamide (carbamazepine).

In various embodiments, the HDAC inhibitor is a non-selective HDAC inhibitor. In specific embodiments, the non-selective HDAC inhibitor includes, but is not limited to:
  (S)—N-hydroxy-4-(3-methyl-2-phenylbutanamido)benzamide (AR-42).
  2-Propylpentanoic acid (valproic acid);
  N'-hydroxy-N-phenyl-octanediamide (suberoylanilide hydroxamic acid or SAHA or vorinostat);
  5H-dibenz[b,f ]azepine-5-carboxamide (carbamazepine);
  N-Hydroxy-N'-3-pyridinyloctanediamide (pyroxamide);
  N-hydroxy-3-[3-(hydroxyamino)-3-oxo-1-propen-1-yl]-benzamide (CBHA);
  7-[4-(dimethylamino)phenyl]-N-hydroxy-4,6-dimethyl-7-oxohepta-2,4-dienamide (trichostatin A or TSA);
  7-[4-(Dimethylamino)phenyl]-N-(β-D-glucopyranosyloxy)-4,6-dimethyl-7-oxo-2,4-heptadienamide (trichostatin C);
  2-Hydroxybenzenecarbohydroxamic acid (salicylihydroxamic acid or SBHA);
  N,N'-dihydroxynonanediamide (azelaic bihydroxamic acid or ABHA);
  azelaic-1-hydroxamate-9-anilide (AAHA);
  (1S,4S,7Z,10S,16E,21R)-7-ethylidene-4,21-diisopropyl-2-oxa-12,13-dithia-5,8,20,23-tetrazabicyclo[8.7.6]tricos-16-ene-3,6,9,19,22-pentone (romidepsin or FK228);
  6-(3-chlorophenylureido) carpoic hydroxamic acid (3Cl-UCHA);
  (2E)-5-[3-(Phenylsulfonylamino)phenyl]-pent-2-en-4-ynohydroxamic acid (oxamflatin);
  7-[4-(4-cyanophenyl)phenoxy]-heptanohydroxamic acid (A-161906);
  6-(1,3-Dioxo-1H, 3H-benzo[de]isoquinolin-2-yl)-hexanoic acid hydroxyamide (scriptaid);
  N-hydroxy-3-[3-](phylamino)sulfonyl phenyl]-2-propenamide (Belinostat or PXD-101);

(E)-3-(4-(((2-(1H-indol-3-yl)ethyl)(2-hydroxyethyl) amino)methyl)phenyl)-N-hydroxyacrylamide (LAQ-824);

MW2796 (see Andrews et al. (2000) *International J. Parasitology* 30,761-768);

(2E)-N-hydroxy-3-[4-({[2-(2-methyl-1H-indol-3-yl) ethyl]amino}methyl)phenyl]acrylamide (Panobinostat or LBH589);

4-acetylamino-N-(2'-aminophenyl)-benzamide (CI-994);

N-hydroxy-2-(4-(naphthalen-2-ylsulfonyl)piperazin-1-yl) pyrimidine-5-carboxamide (R306465);

{6-[(diethylamino)methyl]naphthalen-2-yl}methyl [4-(hydroxycarbamoyl)phenyl]carbamate (givinostat or ITF2357);

3-[(Dimethylamino)methyl]-N-{2-[4-(hydroxycarbamoyl)phenoxy]ethyl}-1-benzofuran-2-carboxamide (abexinostat or PCI-24781);

3-[2-butyl-1-[2-(diethylamino)ethyl]-1H-benzimidazol-5-yl]-N-hydroxy-2E-propenamide (SB-939);

MW2996 (see Andrews et al. (2000) *International J. Parasitology* 30,761-768);

(E)-3-(1-((4-((dimethylamino)methyl)phenyl)sulfonyl)-1H-pyrrol-3-yl)-N-hydroxyacrylamide (resminostat); or 7-(4-(3-ethynylphenylamino)-7-methoxyquinazolin-6-yloxy)-N-hydroxyheptanamide (CUDC-101).

In other embodiments, the HDACi is a Class I Selective HDACi, including but not limited to:

N-(2-amino-phenyl)-4-[(4-pyridin-3-yl-pyrimidin-2-ylamino)-methyl]-benzamide) (MGCD-0103 or mocetinostat);

Pyridin-3-ylmethyl N-[[4-[(2-aminophenyl)carbamoyl] phenyl]methyl]carbamate (Entinostat or SNDX-275 or MS-275);

(1S,5S,6R,9S,15E,20R)-5-hydroxy-20-methyl-6-(propan-2-yl)-2-oxa-11,12,dithia-7,19,22-triazabicyclo [7.7.6]docos-15-ene-3,8,18,21-tetrone (spiruchostatin A);

4-(dimethylamino)-N-[[4-[(E)-3-(hydroxyamino)-3-oxoprop-1-enyl]phenyl]methyl]benzamide (SK-7041);

SK7068 (see Park et al. (2002) Eur. J. Cancer 38: Abst 318); or 6-amino nicotinamides.

In further embodiments, the HDACi is selected from one of the following groups: short-chain fatty acids; hydroxamic acids; epoxyketone-containing cyclic tetrapeptides; non-epoxyketone-containing cyclic tetrapeptides; benzamides; and other miscellaneous structures (e.g., Savicol, Bacecca, MG98, Depudecin, Organosulfur compounds). Short-chain fatty acids include butyrate and phenylbutyrate, isovalerate, valproate, 4-phenyl butyrate (4-PBA), phenylbutyrate propionate, butyaramide, isobiltyaramide, phenylacetate, 3-bromopropionate, tributyrin, valproic acid, and Pivanex. Hydroxamic acids include the trichosta ins such as TSA and TSC, SAHA and its derivatives, Oxamflatin, ABHA, AAHA, SBHA, CBHA, pyrozamide, salicylbishyudoxamic acid, Scriptaid, Pyroxamide, Propenamides, LBH589, CHAP, MY29996, MW2976, and any of the hydroximic acids disclosed in U.S. Pat. Nos. 5,369,108; 5,932,616; 5,700,811; 6,087,367; and 6,511,990. Epoxyketone-containing cyclic tetrapeptides include trapoxins, depeudecin, depsipeptide FK228, FR 225497 Apicidin, cyclic tetrapeptide. Anicidin Ia, Apicidin Ib, Apicidin Ic, Apicidin IIa, Apicidin III, a cyclic tetrapeptide containing a 2-amino-8-oxo-9,10-epoxy-decanoyl moiety, a cyclic peptide without the 2-amino-8-oxo-9,10 epoxy-decanoyl moiety, HC-toxin, Chlamydocin, Diheteropeptin, WF-3161, Cyl-1 and Cyl-2).

Non-epoxyketone-containing cyclic tetrapeptides include FR901228, Apicidin, cyclic-hydroxamic-acid-containing peptides (CHAPs). Benzamides include MS-275, N-acetyldinaline, CI-994, MGCD0103, AR-42, and other benzamide analogs.

In other embodiments of the methods of the presently disclosed subject matter for treating a Mendelian disorder of the epigenetic machinery in a subject in need thereof, the defective gene encoding a component of the epigenetic machinery encodes a histone deacetylase, and the agent that restores balance between open and closed chromatin states at one or more target genes is a histone acetyltransferase (HAT) inhibitor. In further embodiments, the HAT inhibitor is selected from the group consisting of: (1E,6E)-1,7-Bis(4-hydroxy-3-methoxyphenyl)-1,6-heptadiene-3,5-dione (curcumin); and 2-hydroxy-6-pentadecyl-benzoic acid (anacardic acid).

One of skill in the art will recognize that agents for use within the methods of the presently disclosed subject matter include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When agents for use within the methods of the presently disclosed subject matter contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When agents for use within the methods of the presently disclosed subject matter contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the agents for use within the methods of the presently disclosed subject matter may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of an agents for use within the methods of the presently disclosed subject matter is selected from the group consisting of HCl, a sulfonate, a sulfate, phosphate, a malonate, a succinate, a fumarate, a maleate, a tartrate, a 3-sulfopropanoic acid salt, and a citrate.

Certain agents for use within the methods of the presently diclosed subject matter can exist in unsolvated forms, as well as solvated forms, including hydrated forms. In general, the solvated forms are equivalent to unsolvated forms and are encompassed within the scope of the present disclosure. Certain agents for use within the methods of the presently disclosed subject matter may exist in multiple crystalline or amorphous forms. In general, all physical forms are equivalent for the uses contemplated by the present disclosure and are intended to be within the scope of the present disclosure.

In addition to salt forms, the present disclosure provides agents for use within the methods that can be in a prodrug form. Prodrugs of the agents for use within the methods of the presently disclosed subject matter are those compounds that readily undergo chemical changes under physiological conditions to provide the compounds of the present disclosure. Additionally, prodrugs can be converted to the agents for use within the methods of the presently disclosed subject matter by chemical or biochemical methods in an ex vivo environment. For example, prodrugs can be slowly converted to the agents for use within the methods of the presently disclosed subject matter when placed in a transdermal patch reservoir with a suitable enzyme or chemical reagent.

E. Dosage and Mode of Administration

Agents that restore balance between open and closed chromatin states at one or more target genes as described elsewhere herein can be administered using a variety of methods known in the art. The administering can be carried out by, for example, intravenous infusion; injection by intravenous, intraperitoneal, intracerebral, intramuscular, intraocular, intraarterial or intralesional routes; or topical or ocular application.

More particularly, as described herein, agents within the methods of the presently disclosed subject matter can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intraarticullar, intra -sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound of Formula (Ia) or Formula (II) together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, agents within the methods of the presently disclosed subject matter can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Agents for use within the methods of the presently disclosed subject matter can be manufactured in a manner known in the art, e.g. by means of conventional mixing, dissolving, granulating, dragee-making, levitating, emulsifying, encapsulating, entrapping or lyophilizing processes.

More particularly, agents within the methods of the presently disclosed subject matter for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the agents for use within the methods of the presently disclosed subject matter can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133, 988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544, 545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, pre-determined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, agents for use within the methods of the presently disclosed subject matter also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

Regardless of the route of administration selected, agents for use within the methods of the presently disclosed subject matter, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., Mendelian disorders of the epigenetic machinery), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the agents for use within the methods of the presently disclosed subject matter at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological may be different from the amount of compound effective for another purpose.

In general, a suitable daily dose of an agent for use within the methods of the presently disclosed subject matter will be that amount of the compound that is the lowest dose effective to produce a therapeutic effect. Such an effective dose will generally depend upon the factors described above. Generally, doses of the agents for use within the methods of the presently disclosed subject matter will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of an agent for use within the methods of the presently disclosed subject matter can be administered as two, three, four, five, six or more sub-doses administered separately at appropriate intervals throughout the day, optionally, in unit dosage forms.

In some embodiments, the ketogenic composition is administered at least once daily. In some embodiments, the ketogenic composition is administered as part of a daily treatment regimen that lasts for at least two weeks. In some embodiments, the ketogenic composition is administered as part of a daily treatment regimen that lasts for at least 5 years or longer. In some embodiments, the ketogenic composition is administered as part of a daily treatment regimen that lasts from 1 to 5 years. In some embodiments, the ketogenic composition is administered as part of a daily treatment regimen that lasts from 6 months to 1 year. In some embodiments, the ketogenic composition is administered as part of a daily treatment regimen that lasts from 3 months to 9 months. In some embodiments, the ketogenic composition is administered as part of a daily treatment regimen that lasts about 6 months.

F. Selection Methods for Mendelian Disorders

In some embodiments, the presently disclosed subject matter provides methods for selecting a subject for treatment with a therapy for a Mendelian disorder of the epigenetic machinery by determining whether the subject has an imbalance between open and closed chromatin states at one or more target genes. In some embodiments, the presently disclosed subject matter provides methods for selecting a subject for treatment with a therapy for a Mendelian disorder of the epigenetic machinery by determining whether the subject has a redox imbalance. In some embodiments, the subject is selected by determining whether the subject has a redox imbalance and whether the subject has an imbalance between open and closed chromatin states at one or more target genes. The subject may have, or is suspected of having, a redox imbalance. As used herein, the term "redox imbalance" refers to a change in an oxidation-reduction reaction in a subject with a Mendelian disorder of the epigenetic machinery as compared to the oxidation-reduction reaction in a normal subject without the disorder. Examples of oxidation-reduction reactions include the conversion of pyruvate to lactate, which is catalyzed by lactate dehydrogenase, and the conversion of β-hydroxybutyrate to acetoacetate, which is catalyzed by 3-hydroxybutyrate dehydrogenase. A variety of methods for determining whether a subject has an imbalance between open and closed chromatin states at one or more target genes are available to the skilled artisan, e.g., by measuring histone marks, and/or DNA methylation, e.g., by quantifying global levels of H3K4me3 in Kabuki syndrome (expected to be decreased), H3K27me3 in Kabuki syndrome (expected to be increased) and Weaver syndrome (expected to be decreased), and histone acetylation in Rubinstein-Taybi syndrome (expected to be decreased) and Brachydactyly-Mental Retardation (expected to be increased).

In some embodiments, the presently disclosed subject matter provides a method of selecting a subject for treatment with a therapy for a Mendelian disorder of the epigenetic machinery, the method comprising: (a) obtaining a biological sample from the subject; (b) assaying the biological sample for levels of: (i) acetoacetate and β-hydroxybutyrate; and/or (ii) pyruvate and lactate; (c) determining a ratio of: (i) the levels of acetoacetate in the biological sample relative to the levels β-hydroxybutyrate in the biological sample; and/or (ii) the levels of pyruvate in the biological sample to the levels of lactate in the biological sample; (d) comparing the ratios determined in (c)(i) and/or (c)(ii) to control ratios of (c)(i) and/or (c)(ii) from biological samples of normal individuals lacking a redox imbalance; and (e) selecting a subject for treatment with a therapy for a Mendelian disorder of the epigenetic machinery if the ratios determined in (c)(i) and/or (c)(ii) are decreased relative to the control ratios.

As used herein, the term "biological sample" encompasses a variety of sample types obtained from a subject and useful in the procedure of the presently disclosed subject matter. In one embodiment of the presently disclosed subject matter, the biological sample comprises whole blood, hemocytes, serum, plasma, or urine. However, biological samples may include, but are not limited to, solid tissue samples, liquid tissue samples, biological fluids, aspirates, cells and cell fragments. Specific examples of biological samples include, but are not limited to, solid tissue samples obtained by surgical removal, pathology specimens, archived samples, or biopsy specimens, tissue cultures or cells derived therefrom and the progeny thereof, and sections or smears prepared from any of these sources. Non-limiting examples of biological samples include samples obtained from breast tissue, lymph nodes, and breast tumors. Biological samples also include any material derived from the body of a vertebrate animal, including, but not limited to, blood, cerebrospinal fluid, serum, plasma, urine, nipple aspirate, fine needle aspirate, tissue lavage such as ductal lavage, saliva, sputum, ascites fluid, liver, kidney, breast, bone, bone marrow, testes, brain, ovary, skin, lung, prostate, thyroid, pancreas, cervix, stomach, intestine, colorectal, brain, bladder, colon, nares, uterine, semen, lymph, vaginal pool, synovial fluid, spinal fluid, head and neck, nasopharynx tumors, amniotic fluid, breast milk, pulmonary sputum or surfactant, urine, fecal matter and other liquid samples of biologic origin.

In some embodiments, the control ratio of the levels of acetoacetate relative to the levels of β-hydroxybutyrate in a biological sample of a normal individual lacking a redox imbalance is about 1:1.

In some embodiments, the subject is selected for treatment with a therapy for a Mendelian disorder of the epigenetic machinery when the determined ratio of the levels of acetoacetate relative to the levels of β-hydroxybutyrate in the biological sample is less than about a 1:1 ratio, such as less than about 0.9.

In some embodiments, the control ratio of the levels of lactate relative to the levels of pyruvate in a biological sample of a normal individual lacking a redox imbalance is about 20 to 25.

In some embodiments, the subject is selected for treatment with a therapy for a Mendelian disorder of the epigenetic machinery when the determined ratio of the levels of lactate relative to the levels of pyruvate in the biological sample is about 30 or higher. In some embodiments, the subject is selected for treatment with a therapy for a Mendelian disorder of the epigenetic machinery when the determined ratio of the levels of lactate relative to the levels of pyruvate in the biological sample is about 40 or higher. In some embodiments, the subject is selected for treatment with a therapy for a Mendelian disorder of the epigenetic machinery when the determined ratio of the levels of lactate relative to the levels of pyruvate in the biological sample is about 30 to about 40.

In some embodiments, the biological sample is selected from the group consisting of serum, whole blood, plasma, hemocytes, and urine. In some embodiments, the step of assaying comprises an assay selected from the group consisting of a colorimetric assay, a fluorometric assay, gas chromatography-mass spectrometry, fingerstick and handheld monitor. If the subject has a redox imbalance, the methods may further comprise administering to the subject a presently disclosed ketogenic composition. In some embodiments, the Mendelian disorder of the epigenetic machinery is Kabuki syndrome.

G. Kits for Selecting or Treating a Subject with a Mendelian Disorder of the Epigenetic Machinery The presently disclosed subject matter also relates to kits for practicing the methods of the presently disclosed subject matter. In general, a presently disclosed kit contains some or all of the components, reagents, supplies, and the like to practice a method according to the presently disclosed subject matter. In some embodiments, the term "kit" refers to any intended article of manufacture (e.g., a package or a container) comprising at least one ketogenic composition, and a set of particular instructions for practicing the methods of the presently disclosed subject matter. In some embodiments, the term "kit" refers to any intended article of manufacture comprising at least one reagent for detecting a redox imbalance in a biological sample. The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components.

In some embodiments, a kit comprises (a) a ketogenic composition in an amount sufficient to produce a physiologically acceptable ketosis in the subject; and (b) a package insert or label with directions to treat a subject with a Mendelian disorder of the epigenetic machinery by administering the ketogenic composition. In some embodiments, the kit can be used to treat Kabuki syndrome. In some embodiments, the amount is sufficient to produce a physiologically acceptable ketosis in the subject when the ketogenic composition is administered according to the package insert or label at a prescribed frequency and for a prescribed period of time.

In some embodiments, the prescribed frequency is at least once daily, at least twice daily, or at least thrice daily. In some embodiments, the prescribed period of time is at least two weeks, at least three weeks, at least 30 days, at least two months, at least three months, at least four months, at least five months, at least six months, at least seven months, at least eight months, at least nine months, at least 10 months, at least 11 months, at least one year, at least 18 months, at least 24 months, at least 30 months, at least 36 months, at least 42 months, at least 48 months, at least 54 months, at least 60 months, or more.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Disease Associated Kabuki Syndrome Phenotypes

Materials and Methods

Study design: The purpose of this study was to explore the pathophysiological sequence in KS, a Mendelian disorder of the epigenetic machinery, and to seek robust disease associated phenotypes, which could be used to monitor therapeutic response. It was hypothesized that since both causes of KS involve the transition from closed to open chromatin, this disorder might be caused by a general imbalance between open and closed chromatin states (favoring closed chromatin) and this ongoing deficiency might be ameliorated with agents that favor chromatin opening such as HDACi. At least 3-4 biological replicates were used for each biochemical analysis, while a sample size of at least 8-10 per group was used for behavioral testing. Data collection occurred for a pre-determined and of consistent duration, as dictated by literature-based or core facility-based standards and no exclusion criteria were applied. All analyses were performed by examiners blinded to genotype and/or treatment arm. For drug treatments, animals were randomly assigned to treatment arms with approximately equivalent numbers in each group. Box and whisker plots identify RStudio-defined outliers (shown as circles), but all data points were used in statistical analyses.

Design of the indicator constructs. A genetically encoded histone reporter allele system has been developed which can be used to monitor activity of any histone maintenance machinery component in live cells. Previously, FRET based epigenetic activity systems have been created (Lin and Ting (2004) *Angew Chem Int Ed Engl.* 24;43 (22):2940-3; Lin et al. (2004) *J. Am. Chem. Soc.* 19;126(19):5982-3; U.S. Pat. No. 7,056,683). However, FRET-based assays need a complex technological setup which is not widely available and FRET-based assays have been much more difficult to introduce into transgenic mouse models. Here, the presently disclosed non-FRET-based histone indicator system is demonstrated through examples of two well understood histone modifications, histone acetylation and histone H3K4 trimethylation. The particular construct design is based on a circularly permutated green fluorescent protein (GFP) that lacks fluorescence unless the two parts of GFP are brought into close proximity by external forces (Baird et al. (1999) *Proc. Natl. Acad. Sci. U.S.A.* 28;96(20):11241-6). The constructs are targeted to the nucleus through a nuclear localization signal (NLS). Mutants were also created that knocked out the activity of the indicator allele.

The acetyl reporter protein quantifies the activity of the acetylation machinery (acetylation of H4 specifically at the 5th, 8th, 12th and 16th Lysine's) and comprises an H4 tail on one end (the target for acetylation) and a TBP associated factor II (TAFII) bromodomain on the other end of the reporter protein. The TAFII bromodomain only recognizes and binds to the acetylated H4 tail, resulting in reconstitution of GFP structure and function (i.e. fluorescence). Therefore, the reporter protein has no fluorescence unless it is acetylated by the acetylation system of the nucleus of the cell.

An H3K4 trimethylation reporter was also created. This reporter is based on the H3 tail on one end and the TBP associated factor III (TAFIII) homeodomain on the other end; the TAFIII homeodomain only identifies and binds to trimethylated K4 on H3. When the H3K4 site gets trimethylated, the TAFIII homeodomain can bind to the modified H3 tail and bring the two parts of the separated GFP in close proximity. The activity of the epigenetic modification system can be quantified through fluorescence.

Epigenetic reporter alleles: Epigenetic reporter alleles were synthesized (OriGene, Rockville, Md.) using published sequences for component elements (Baird et al. (1999) *Proc. Nail. Acad. Sci.* 96:11241-6; Souslova et al. (2007) *BMC Biotechnol.* 7:37). Single nucleotide mutations were created using the QuickChange Lightening kit (Agilent Technologies Inc, Santa Clara, Calif.). For H4ac indicator, K5R, K8R, K12R, K16R and K20R (MUT indicator) were introduced. For H3K4me3 indicator, K4Q and D890A/W891A and M882A (three separate constructs) were introduced. For transient transfections, mouse embryonic fibroblasts (see below) were transfected with Fugene HD (Promega, Madison, Wis.), 48 hours prior to FACS. Transfection efficiency of reporter alleles was comparable in transiently-transfected murine embryonic fibroblasts (MEFs) derived from mice of both genotypes (Kmt2d$^{+/\beta Geo}$ and Kmt2d$^{+/+}$), as measured by real-time PCR of genomic DNA. For drug stimulation, drug was added to the media 24 hours prior to FACS. For stable transfections in T293 (American Type Culture Collection) cells, 10 μg/ml of Blastocidin (Life Technologies, Carlsbad, Calif.) was added to the media for several weeks. For stable transfection in MEFs, the reporter was transferred to a ViraPower Lentiviral Expression System (Life Technologies, Carlsbad, Calif.). After selection with Blastocidin, the drug of interest was added 24 hours prior to FACS. SAHA, AR-42 and MS275 were purchased from Selleck (Selleck Chemicals, Houston, Tex.). FACS was performed using either a FACSCalibur (BD Biosciences, San Jose, Calif.) or FACSverse (BD Biosciences, San Jose, Calif.) system with comparable results. FACS data were analyzed using FlowJo (Tree Star Inc, Ashland, Oreg.). A plasmid expressing HDAC3 was acquired from Addgene (Cambridge, Mass., plasmid 13819) and transfected into a stable cell line carrying the H4 acetyl reporter allele.

Animals: Kmt2d$^{+/\beta Geo}$ mice, also named Mll2Gt$^{(RRt024)Byg}$, were acquired from Bay Genomics (University of California). All experimental mice were on a mixed C57BL/6J and 129/SvEv background. Expected Mendelian ratios were observed when heterozygous animals were bred to wild-type. In heterozygous crosses, however, there was uniform embryonic lethality of homozygotes by ED12, the earliest developmental stage assayed. For treatment with AR-42 mice were orally gavaged daily with drug (Selleck Chemicals, Houston, Tex.) solubilized in vehicle (0.5% methylcellulose, 0.1% Tween-80, water) or with vehicle alone. Drug delivery information was kindly provided by Drs. Chen and Kulp from Ohio State University (Huang et al. (2011) *Mol. Pharmacol.* 79:197-20619). Drug was administered for 14 days and mice were sacrificed on day 15. Morris water maze testing was initiated at day 7 and a dose of 10 mg/kg/day was used for these studies. For quantification of DCX positive cells, doses of 0, 5, 10 and 25 mg/kg/day were used. Genotyping was performed using primers B-GeoF-(CAAATGGCGATTACCGTTGA; SEQ ID NO: 1) and B-GeoR-(TGCCCAGTCATAGCCGAATA; SEQ ID NO: 2) that are specific for the targeted allele and TcrdF-(CAAATGTTGCTTGTCTGGTG; SEQ ID NO: 3) and TcrdR-(GTCAGTCGAGTGCACAGTTT; SEQ ID NO: 4) that control for sufficient DNA concentration. Real-time PCR using the same primers allows discrimination between the heterozygous and homozygous state for the targeted allele. Maxillary protrusion was evaluated by ten investigators blinded to genotype and they were asked to rate maxillary protrusion on radiographs as either large (2) or small (1). When results were unblinded and average scores for each animal determined, the Kmt2d$^{+/\beta Geo}$ animals had a significantly lower score than Kmt2d$^{+/+}$ littermates. All experiments were performed using mouse protocols approved by the Animal Care and Use Committee of Johns Hopkins University School of Medicine. The mouse protocols used for this study are in accordance with the guidelines used by the NIH for mouse care and handling.

Perfusion and cryosectioning: Mice were sacrificed with a xylazine ketamine combination, transcardially flushed with PBS/Heparin and then perfused with 4% PFA/PBS. Brains were dissected and cryopreserved in 30% sucrose 0.1M phosphate solution overnight at 4° C. Brains were frozen and sectioned using a Microm HM 550 cryostat (Thermo Scientific, Waltham, Mass.). Sectioning was performed at 30 μm intervals and every section of the brain was collected and stored in glycerine etheleyne glycol phosphate storage solution.

EdU administration and staining: For EdU experiments, mice were injected IP over ten days, with injections on the first three and last three days, with 50 mg/kg EdU (Life Technologies, Carlsbad, Calif.). Mice were sacrificed 30 days after the initial start of injection, and EdU staining was done with the Click-iT EdU Alexa Fluor 488 Imaging Kit (Life Technologies, Carlsbad, Calif.) as well as DAPI mounting with Vectamount (Vector Laboratories, Burlingame, Calif.). EdU quantification was performed by an individual blinded to genotype. Positive cells were counted in every sixth slice in the GCL and the average number per slice was calculated for each brain.

Real time PCR: Real-time PCR was performed using Kmt2d-specific probes for exons 20 and 52 (Mm_02600438 and Mm_01717664, respectively) from TaqMan® Gene Expression Assays (Life Technologies, Carlsbad, Calif.). For a comparison of transfection efficiencies for indicator constructs in transient transfection studies, real-time PCR was performed using SYBR Green Real-Time PCR Master Mix (Life Technologies, Carlsbad, Calif.) and primers IND-F-(CTGCGCGCAAGTCAACGGGTG; SEQ ID NO: 5) and IND-R-(ATGCCGTTCTTCTGCTTGTCG; SEQ ID NO: 6) that are specific for the H3K4 methylation indicator. For expression analysis for KMT2D target gene KLF10, real-time PCR was performed using Klf10-specific expression assay (Mm00449812_m1) from TaqMan® Gene Expression Assays (Life Technologies, Carlsbad, Calif.).

Immunoblotting: Total protein lysates from Kmt2d$^{+/\beta Geo}$ and Kmt2d$^{+/+}$ littermates were isolated and immunoprecipitated with an antibody against the amino terminus of KMT2D (sc-292359, Santa Cruz Biotechnology, Dallas, Tex.). Isolated protein was applied to a membrane and immunoblotted with an antibody against beta-galactosidase (ab9361, Abcam, Cambridge, ENG) as previously described (Loeys et al. (2010) *Sci. Transl. Med.* 23: 23ra20).

Immunofluorescence: Every $6^{th}$ brain section was selected and then blocked with 5% Bovine Serum Albumin (BSA) at room temperature followed by incubation with primary antibodies overnight at 4° C. Secondary antibodies were then applied for 1 hour at room temperature, after which sections were mounted onto microscope slides with Vectamount with DAPI (Vector Laboratories, Burlingame, Calif.). Primary antibodies included Doublecortin (DCX) (SC-8066, Santa Cruz Biotechnology, Dallas, Tex., 1:200 goat), trimethylated H3K4 (9727L, Cell Signaling Technology, Beverly, Mass., 1:500 rabbit), and Kmt2d H-300 (SC-292359, Santa Cruz Biotechnology, Dallas, Tex., 1:500 rabbit). Non-specific binding was not observed when sections were sequentially exposed to serum (or IgG when appropriate) from the same species as the primary antibody for each experiment (i.e. rabbit for KMT2D and H3K4me3 and goat for doublecortin), followed by the secondary antibody used for KMT2D and H3K4me3 (anti-rabbit) or doublecortin (anti-goat, FIG. 27).

Confocal microscopy: Z-stack images of slides were taken at either 10× using Zeiss Axiovert 200 with 510-Meta confocal module (Carl Zeiss, Jena, GER) or 25× using Zeiss AxioExaminer with 710NLO-Meta multiphoton (Carl Zeiss, Jena, GER). From 10× pictures, the GCL was highlighted and fluorescent intensities for both DAPI and H3K4me3 were measured at the midpoint of the entire z-stack (Zen software, Carl Zeiss, Jena, GER) with the value for Kmt2d$^{+/+}$ animals set equal to one. A Students t-test with significance value set at P<0.05 was used to compare H3K4 trimethylation intensity referenced to DAPI intensity.

GCL and doublecortin area: The area of both the GCL and DCX+ cells was measured using the NS elements 2.0 software (Nikon, Tokyo, JPN). Normalized DCX area was calculated by measuring the DCX+ area of the GCL and setting the baseline (Kmt2d$^{+/+}$) fraction to 1. A Student t-test with significance value set at P<0.05 was used for comparison of DCX+ area referenced to GCL area between genotypes and treatment arms.

Behavioral testing: Mice ranged from two to three months of age in all tests, and all experiments were performed in the late morning or early afternoon.

Novel object recognition: On the first day of the novel object recognition test, mice were individually placed into a square plastic arena (25 cm×25 cm×25 cm) that contained two identical plastic objects along the midline of the arena. Each mouse was allowed to explore the objects for 10 minutes and then placed back in its home cage. The following day, each mouse was placed in the same arena with the same two identical objects and the time interacting with each object was recorded over 10 minutes. On the third day, one object was removed and was replaced by a novel object. Mice were placed in the arena for five minutes and timed for interaction with the familiar object compared to the novel object. Interactions with objects were recorded and measured in a way that was blinded to both genotype and drug treatment. Differences in interaction time between the novel object and the familiar object for Kmt2d$^{+/+}$ and Kmt2d$^{+/\beta Geo}$ mice were calculated by computing time spent with the novel object divided by the total time spent with both objects. These values were analyzed for significance with a Student's t-test with significance value set at P<0.05.

Morris water maze: Mice were placed in a 1.1 meter diameter tank filled with room temperature water dyed with non-toxic white paint. For analysis purposes, the tank was divided into four quadrants, with one quadrant containing a small platform submerged 1.5 cm beneath the water. On each day of training, mice were placed in the tank in a random quadrant facing away from the center and were allowed to swim until they found the platform and were left there for 30 seconds. If they did not reach the platform after 60 s they were placed on it for 30 seconds. Each mouse was given 4 trials per day (for 5 days) with no inter-trial interval and subsequently returned to its home cage. Latency to reach the platform was measured during each trial. The day after the final day of training, the platform was removed for a probe trial where mice were placed in the tank for 90 s. Average number of crossings of the platform's previous location was recorded. Visible/flagged platform training was also performed for 3 days either before the hidden platform or after the probe trial, where a visible flag was placed on the submerged platform, and the time for each mouse to reach the platform was measured for each 60 second trial, four of which were run in the same way as the hidden platform training. For all training and probe testing, data was recorded both manually and electronically with ANY-maze software (San Diego Instruments, San Diego, Calif.) when applicable. All data were collected and analyzed by an individual blinded to genotype and treatment group. Differences in the number of platform crossings during the probe trial were compared between groups with a Student's t-test with significance value set at P<0.05.

Fear conditioning testing: On day 1, both Kmt2d$^{+/\beta Geo}$ mice and Kmt2d$^{+/+}$ littermates were placed in chamber and allowed to explore the chamber freely. After 120 seconds (2 minutes), a 2000 Hz sound was played for 30 seconds. For the last 2 seconds of sound (seconds 148-150), the sound co-occurred with a 0.35 mAmp electrical shock (2 seconds) administered through the floor grid. Mice were observed for a total of 300 seconds. Freezing behavior was measured using the FreezeScan software (CleverSys Inc, Reston, Va.). On days 2 and 14 (FIG. 8), contextual freezing was assessed over 300 seconds (no cue). On days 3 and 15, cued freezing was assessed over 300 seconds.

Open field testing: Mice were placed in the open field chamber and activity was monitored using the Photobeam activity system (San Diego Instruments, San Diego, Calif.). Activity levels (ten 180 second intervals) were pooled to yield a general activity level (Adamczyk et al. (2012) *Behav Brain Res.* 229: 265-72).

Grip strength testing: Grip strength testing was performed as previously described (Adamczyk et al. (2012) *Behav Brain Res.* 229: 265-72). Three trials were performed and averaged for each mouse.

Retrospective analysis of neuropsychological testing on patients with Kabuki syndrome: A retrospective chart review was performed using data from patients that had clinically indicated neuropsychological testing at the Kennedy Krieger Institute in years 2004-2014. Test results were analyzed from the three individuals with most extensive testing available and a known disease associated mutation in KMT2D. All patient data was collected after consenting patients and stored in secure electronic database at KKI. For this particular analysis per Kennedy Krieger and Johns Hopkins organizational policy, additional IRB review was not required (three or fewer patients). The individual tasks were divided into 16 categories, and literature was used to identify tasks known to be associated with dentate gyrus (Kesner (2013) *Behav. Brain Res.* 254:1-7; Morris et al. (2012) *Neurobiol. Learn. Mem.* 97:326-31; Epp et al., (2011) *Neurobiol. Learn. Mem.* 95:316-25) or hippocampus (non-dentate gyrus).

ChIP-seq: Spleens were dissected from eight mice, four from each kmt2d genotype (+/βGeo or +/+) where half of each genotype was treated with AR-42 and half with vehicle only. Spleens were minced and passed through a 40 mm cell strainer to obtain single cell suspensions. 10 million cells were used for each ChIP-seq experiment following the native chromatin immunoprecipitation protocol, as previously described (Gilfillan et al. (2012) *BMC Genomics* 13:645), using a ChIP-grade antibody against H3K4me3 (9727, Cell Signaling Technology, Beverly, Mass.).

ChIP-seq data analysis: Sequencing was performed using a MiSeq system (Illumina, San Diego, Calif.). 4.8-9.6 million paired-end 26 by reads were obtained per sample (Table 2; nReads=number of reads, alignRate=fraction aligned to genome; FRIP=fraction of reads in peaks). Reads were aligned to the *m. musculus* genome, version mm10, using Bowtie 2 (Langmead and Salzberg (2012) *Nat. Methods.* 9: 357-9). Each sample was examined with regard to alignment rate as well as FRIP (fraction of reads in peaks), a measure of the ChIP efficiency (Table 2). FRIP was computed based on peaks called only on specific samples using MACS version 1.4.2 (Zhang et al. (2008) *Genome Biol.* 9: R137). For analysis, reads were merged into one meta-sample and peak calling was performed using MACS version 1.4.2 (Zhang et al. (2008) *Genome Biol.* 9: R137). This allowed definition of a superset of 33,517 peaks in one or more samples. The number of reads overlapping a peak was computed using bedtools version 2.17.0 (Quinlan and Hall (2010) *Bioinformatics* 26:841-2) in the following way: each paired-end read was converted to a single interval containing both mate coordinates (effectively filling in the insert) and these intervals were examined for overlaps with the superset of peaks. This created a peak by sample matrix of read counts. Differential binding was assessed using the GLM functionality (McCarthy et al. (2012) *Nucleic Acids Res.* 40:4288-97) in edgeR version 3.5.27 (Robinson et al. (2010) *Bioinformatics.* 26:139-40). A single model was fit, using all 8 samples, with Tagwise variance estimation. Different contrasts were examined corresponding to the different hypotheses considered in the main text, and peaks were considered differentially bound if they had a Benjamini-Horchberg corrected p-values less than 5%. Fold change and overall abundance was calculated as per edgeR.

For FIG. 5D, FIG. 23E, and FIG. 25, each point corresponds to a genomic location with an H3K4me3 peak in at least one of the samples. A positive value indicates that the peak is higher in the Kmt2d$^{+/\beta Geo}$ compared to the Kmt2d$^{+/+}$. Peaks which are significantly differentially bound are shown in red, and other peaks are shown in gray. In FIG. 25A, FIG. 25B. FIG. 25C, FIG. 25D, and FIG. 25E, the expected medium is demonstrated with a broken line, but unbroken line shows the median in the observed comparison. FIG. 26A, FIG. 26B, FIG. 26C, FIG. 26D, and FIG. 26E illustrates whether the balance is shifting up (blue) or down in a particular comparison. To examine whether there was a directional balance between differentially bound genes, the following test was developed. For Kmt2d$^{+/+}$ (vehicle) compared to Kmt2d$^{+/\beta Geo}$ (vehicle), 454 peaks are observed to be stronger bound in the mutant, 1499 to be stronger bound in the wild-type and 27,052 peaks to not be differentially bound. The model assumes that these three numbers follow a multinomial distribution with a probability vector (p1, p2, p3). To test for directional balance, a standard likelihood-ratio test for the hypothesis p1=p2 is constructed. Per standard results, two times the negative log-likelihood ratio test statistic is asymptotically chi-square distributed with 1 degree of freedom.

TABLE 2

A summary of genotypes, drugs and quality measures of ChIP-seq experiments.

| Genotype | Drug | Run | nReads | alignRate | FRIP |
|---|---|---|---|---|---|
| Kmt2d$^{+/\beta Geo}$ | AR-42 | run4 | 5890117 | 0.92 | 0.508 |
| Kmt2d$^{+/\beta Geo}$ | Vehicle | run4 | 7520215 | 0.93 | 0.556 |
| Kmt2d$^{+/+}$ | AR-42 | run4 | 9614420 | 0.92 | 0.48 |
| Kmt2d$^{+/+}$ | Vehicle | run4 | 6828962 | 0.92 | 0.571 |
| Kmt2d$^{+/\beta Geo}$ | AR-42 | run5 | 7604137 | 0.93 | 0.53 |
| Kmt2d$^{+/\beta Geo}$ | Vehicle | run5 | 6016687 | 0.92 | 0.55 |
| Kmt2d$^{+/+}$ | AR-42 | run5 | 4846490 | 0.93 | 0.545 |
| Kmt2d$^{+/+}$ | Vehicle | run5 | 8682723 | 0.93 | 0.573 |

Statistics and plots: For all box plots generated through RStudio (RStudio Inc, Boston, Mass.), the margins of the box show the upper and lower quartiles, the central line shows the median, and the whiskers show the range. Circles denote outliers as defined by the RStudio algorithm. For all column, line, and scatter-plot graphs (generated through Microsoft Excel), the error bars represent standard error of the mean, with the data point representing the mean of each applicable group. Unless otherwise stated, significance between two groups was calculated with a Student's t-test with a significance value of P<0.05. Two-way repeated measures ANOVAs were calculated with SPSS (IBM, Armonk, N.Y.). For every calculated P value the stated n represents the number of animals for each group contributing to that comparison. For P value nomenclature, *=P<0.05, **=P<0.01, †=P<0.005, ††=P<0.001.

Results

Kmt2d$^{+/\beta Geo}$ mice: KMT2D is a member of the mixed lineage leukemia (MLL) family of *Drosophila* Trithorax orthologs that is encoded on human chromosome 12 and mouse chromosome 15. An alternative name for KMT2D is mixed lineage leukemia 2 (MLL2). All members of this family contain a SET domain, which confers the H3K4 methyltransferase activity, as well as other domains (Hunter et al. (2012) *Nucleic Acids Res.* 40: 306-12) that delineate individual functions (FIG. 5A). A mouse model harboring a loss-of-function allele for Kmt2b, encoded on human chromosome 19 and mouse chromosome 7, has been characterized previously (Kerimoglu et al. (2013) *J. Neurosci.* 33, 3452-64), demonstrating hippocampal memory defects. This gene has been alternatively designated Mll4 or Mll2, leading to confusion in the literature regarding nomenclature for this particular gene family, as discussed in a recent publication by Bögerhausen et al. ((2013) *Clin. Genet.* 83: 212-4). To specifically assess the underlying pathogenesis of KS, a novel mouse model has been characterized with insertion of an expression cassette encoding a β-galactosidase neomycin resistance fusion protein (β-Geo) into intron 50 of Kmt2d (Mll2) on mouse chromosome 15. Inclusion of a splice acceptor sequence and a 3'-end cleavage and polyadenylation signal at the 5' and 3' ends of the β-Geo cassette, respectively, is predicted to generate a truncated KMT2D protein with peptide sequence corresponding to the first 50 exons of Kmt2d fused to β-Geo, but lacking the SET domain and therefore methyltransferase activity (FIG. 5B and FIG. 6A). As predicted from this targeting event, quantitative real-time polymerase chain reaction analysis of Kmt2d messenger RNA in Kmt2d$^{+/\beta Geo}$ mice demonstrates normal abundance of sequence corresponding to exon 20 but a 50% reduction for exon 52, when compared to Kmt2d$^{1/}$ littermates (FIG. 5C). Expression of a KMT2D-β-galactosidase fusion protein in Kmt2d$^{+/\beta Geo}$ animals demonstrates transcription and translation of the targeted allele (FIG. 6B). Furthermore, chromatin immunoprecipitation followed by next generation sequencing (ChIP-seq) on splenic cells from Kmt2d$^{+/\beta Geo}$ mice and Kmt2d$^{+/+}$ littermates using an antibody against H3K4me3 reveals an overall genome-wide decrease in H3K4me3 in Kmt2d$^{-/\beta Geo}$ mice (FIG. 5D), supporting the predicted functional consequences of the mutant allele. Finally, Kmt2d$^{+/\beta Geo}$ mice demonstrate facial features that are consistent with KS including flattened snout (FIG. 7A) and downward rotation of the ear canal (FIG. 7B). Blinded analysis of X-rays of Kmt2d$^{+/\beta Geo}$ mice revealed a significantly shorter maxilla (P<0.005) when compared to Kmt2d$^{+/+}$ littermates (FIG. 7B and FIG. 7C), as judged by the extent of protrusion beyond the mandible (FIG. 7C).

Kmt2d$^{+/\beta Geo}$ mice demonstrate hippocampal memory defects: Disruption of several histone modifying enzyme genes has been shown to lead to hippocampal memory defects in mice, illustrating a critical role for epigenetic homeostasis in memory acquisition (Guan et al. (2002) *Cell.* 111: 483-93; Gupta et al. (2010) *J. Neurosci.* 30: 3589-99; Cohen-Armon et al. (2004) *Science* 304:1820-2). Kmt2d$^{+/\beta Geo}$ mice show significant deficits in novel object recognition, (FIG. 5E), Morris water maze tests (FIG. 5F) and contextual fear conditioning (FIG. 8) when compared to Kmt2d$^{+/+}$ littermates, all consistent with hippocampal memory dysfunction. When performed before the hidden platform stage of training, the flag-training phase of the Morris water maze did not reveal significant differences between Kmt2d$^{+/\beta Geo}$ and Kmt2d$^{+/+}$ littermates (FIG. 9). Importantly, Kmt2d$^{+/\beta Geo}$ mice did not show decreased activity (FIG. 10A), reduced grip strength (FIG. 10B) or slower swim speeds (FIG. 10C), any of which would be indicative of a more generalized limitation of performance potential in these assays. There were no significant differences in the time that it took Kmt2d$^{+/\beta Geo}$ mice to identify the platform (escape latency) compared to Kmt2d$^{+/+}$ mice during the training phase (FIG. 11A, FIG. 11B, FIG. 11C, and FIG. 11D).

Decreased dentate gyrus volume and defective neurogenesis in Kmt2d$^{+/\alpha Geo}$ mice: Immunofluorescence analyses revealed particularly high levels of expression of KMT2D protein in the dentate gyrus GCL of the hippocampus in Kmt2d$^{+/+}$ mice (FIG. 12A) and a striking deficiency of H3K4me3 in the dentate gyrus GCL of Kmt2d$^{+/\beta Geo}$ mice compared to wild-type (WT) littermates (FIG. 12B and FIG. 12C). A similar deficiency of H3K4me3 was also seen in the pyramidal layer of the hippocampus (FIG. 13). The levels of H3K4me3 showed substantial cell-to-cell variability in Kmt2d$^{+/\beta Geo}$ animals (FIG. 12B), suggesting that variation in cell state or identity within the GCL or dentate gyrus might influence vulnerability to the consequences of heterozygous Kmt2d disruption. Kmt2d$^{+/\beta Geo}$ mice showed a significant decrease in body but not brain weight (FIG. 14A and FIG. 14B), and had reduced dentate gyrus GCL volume when standardized to brain weight (FIG. 12D and FIG. 12E). This correlated with reduced neurogenesis in the GCL of Kmt2d$^{+/\beta Geo}$ mice, as evidenced by significantly reduced expression of both doublecortin (DCX; Rao and Shetty (2004) *Eur. J. of Neurosci.* 19: 234-246) (FIG. 12F and FIG. 12G) and 5-ethynyl-2'-deoxyuridine (EdU) staining, a marker of both neurogenesis in the GCL and a marker of neuronal survival when monitored 30 days after labeling (FIG. 15). Confocal microscopy revealed an apparent decrease in dendritic branching complexity of DCX positive cells (DCX+) in the GCL of Kmt2d$^{+/\beta Geo}$ mice (FIG. 16). However, given the decreased amounts of DCX+ cells in these mice, further work is needed to determine if this is a true or primary manifestation of Kmt2d deficiency. To explore whether there are hippocampal memory defects in patients with KS, comprehensive neuropsychological testing performed on three patients with known disease causing mutations in KMT2D was analyzed (Table 3; N/A=not adequately tested with utilized testing regimen; ↓=deficient area (defined as >1 standard deviation below the mean and lower than full scale IQ or, if unavailable, highest individual test score; metrics linked to the dentate gyrus are indicated in yellow (Kesner (2013) *Behav. Brain Res.* 254:1-7; Morris et al. (2012) *Neurobiol. Learn. Mem.* 97:326-31; Epp et al., (2011) *Neurobiol. Learn. Mem.* 95:316-25); metrics more broadly linked to the hippocampus are indicated with an asterisk (Brickman et al. (2011) *Hippocampus.* 21:923-8)). Although, not all deficiencies observed can be explained by hippocampal dysfunction, patients consistently had abnormalities of tasks known to be associated with dentate gyrus function (Kesner (2013) *Behav. Brain Res.* 254:1-7; Morris et al. (2012) *Neurobiol. Learn. Mem.* 97:326-31; Epp et al., (2011) *Neurobiol. Learn. Mem.* 95:316-25). Other functions linked to other regions of the hippocampus (Brickman et al. (2011) *Hippocampus.* 21:923-8) were also abnormal in some patients as were some tasks not linked to hippocampus indicating that other cell populations in the central nervous system may also play a role. These data support the hypothesis that observations in Kmt2d$^{+/\beta Geo}$ mice are, at least in part, reminiscent of those seen in KS.

TABLE 3

A retrospective analysis of neuropsychological testing on three patients with mutations in KMT2D reveals consistent abnormalities of functions that have been associated with the dentate gyrus. Neuropsychological testing of patients with known disease causing mutations in KMT2D.

| Neuropsychological process/function | Patient 1 28 yrs Female | Patient 2 15 yrs Female | Patient 3 14 yrs Male |
|---|---|---|---|
| Affected Gene | KMT2D | KMT2D | KMT2D |
| Full Scale IQ | 87 | 84 | 66 |
| Perceptual or Non-verbal Reasoning* | ↓ | ↓ | ↓ |
| Verbal Reasoning/ Comprehension | Normal | Normal | ↓ |
| Verbal Fluency* | ↓ | Normal | N/A |
| Naming* | Normal | Normal | Normal |
| Vocabulary/ Reading | Normal | Normal | N/A |
| Processing Speed | ↓ | ↓ | ↓ |
| Basic Math Calculation | Normal | ↓ | N/A |
| Visual Selective Attention* | ↓ | ↓ | N/A |
| Visual Working Memory* | ↓ | ↓ | ↓ |
| Verbal Working Memory* | Normal | Normal | ↓ |
| Visual Delayed Memory* | ↓ | ↓ | ↓ |
| Verbal Delayed Memory* | ↓ | ↓ | Normal |
| Switching/ Inhibition | ↓ | ↓ | N/A |
| Verbal Organization | Normal | Normal | N/A |
| Visual Organization* | ↓ | ↓ | ↓ |
| Fine Motor | ↓ | ↓ | ↓ |

Application of reporter alleles for epigenetic modifications in embryonic fibroblasts from Kmt2d$^{+/\beta Geo}$ mice: Epigenetic reporter systems were created that monitor either H4 acetylation or H3K4 trimethylation machinery activity in an effort to determine whether there is an ongoing activity deficiency in cells from Kmt2d$^{+/\beta Geo}$ mice (FIG. 17A). Both reporter alleles encode halves of green fluorescent protein separated by a flexible linker region (Baird et al. (1999) *Proc. Natl. Acad. Sci.* 96: 11241-6) with a histone tail and a histone reader at the N- and C-termini, respectively. When the histone tail corresponding to either H4 or H3 is modified by acetylation or methylation, respectively, GFP structure and function are reconstituted, as detected by a fluorescent readout (FIG. 17B). The acetyl reporter protein quantifies the activity of the acetylation machinery (acetylation of H4 specifically at sites K5, K8, K12, and K16) and comprises an H4 tail (residues 1-30) on one end and a TATA binding protein (TBP)-associated factor II (TAFII) bromodomain on the other end (FIG. 17A). The TAFII bromodomain only recognizes and binds to the acetylated H4 tail. This acetylation-dependent reporter protein demonstrates a linear fluorescence response when quantified by fluorescence-activated cell sorting (FACS) in the presence of increasing amounts of suberoylanilide hydroxamic acid (SAHA), an HDACi, in culture systems (FIG. 17C, FIG. 17D, FIG. 18A, FIG. 18B, FIG. 18C, and FIG. 18D). For example, only 5% of cells were easily discriminated from auto fluorescence with 1 μM of SAHA, but increased to 20% with 2.5 μM of SAHA, 40% at 7.5 μM of SAHA and 45% at 10 μM of SAHA (FIG. 17D). Saturation of this response correlates well with immunoblot data using antibodies to the modified H4 tail (Munshi et al. (2006) *Mol. Cancer Ther.* 5:1967-74). This response is attenuated by co-transfection with a construct encoding a histone deacetylase (FIG. 19) and absent upon mutagenesis of all potential acetylation sites (FIG. 17E and FIG. 17I), attesting to its specificity. The H3K4 trimethylation reporter allele encodes the H3 tail (residues 1-40) on one end and the TBP-associated factor III (TAF3) plant homeodomain (PHD) on the other end, which binds to trimethylated K4 on H3 (FIG. 17A). The H3K4 trimethylation reporter also demonstrates a dose response with increasing levels of the HDACi AR-42 (FIG. 17F), in keeping with prior work suggesting that AR-42 can also influence the methylation status of H3K4 through inhibition of demethylases (Huang et al. (2011) *Mol. Pharmacol.* 79:197-206). Activity is greatly attenuated upon mutagenesis of critical residues (M882A, W891A; Vermeulen et al. (2007) *Cell* 131, 58-69; van Ingen et al (2008) *Structure* 16, 1245-56) in the TAF3 reader domain (FIG. 17G) or with mutation of K4 (H3K4Q) in the H3 tail (FIG. 17G). Both reporter alleles show decreased activity when stably introduced into embryonic fibroblasts derived from Kmt2d$^{+/\beta Geo}$ mice, when compared to Kmt2d$^{+/+}$ littermates (FIG. 20). H3K4 trimethylation activity is enhanced upon treatment of Kmt2d$^{+/\beta Geo}$ cells with HDAC inhibitors AR-42 or MS275 (FIG. 17H and FIG. 21A). An analysis of transfection efficacy in cells with both genotypes indicated comparable transfection efficacy (FIG. 21B).

Impaired neurogenesis and H3K4 trimethylation deficiency in Kmt2d$^{+/\beta Geo}$ mice is rescued upon treatment with the HDACi AR-42: Because of the ability of HDACi to increase H3K4 trimethylation in vitro in Kmt2d$^{+/\beta Geo}$ cells, it was next asked whether the H3K4 trimethylation deficiency seen in the dentate gyrus GCL of Kmt2d$^{+/\beta Geo}$ mice could be attenuated or reversed upon in vivo postnatal treatment with an HDACi. Previously, the HDACi's AR-42 and MS275 have both been shown to increase H3K4 trimethylation and histone acetylation (Huang et al. (2011) *Mol. Pharmacol.* 79:197-206). AR-42 appeared to have the strongest effect on H3K4me3 and was therefore chosen for in vivo studies (Huang et al. (2011) *Mol. Pharmacol.* 79:197-206). An AR-42 dose of 25 mg/kg/day was started, previously used in mouse models of prostate cancer (Huang et al. (2011) *Mol. Pharmacol.* 79:197-206), commencing at 20 weeks of age and continuing for two weeks. This dose increased H3K4 trimethylation in the GCL in Kmt2d$^{+/\beta Geo}$ mice, compared to untreated mutant littermates (FIG. 22A and FIG. 22B), to a level that was indistinguishable from treated Kmt2d$^{+/+}$ animals. Unexpectedly, however, this dose of AR-42 was associated with decreased DCX expression in the GCL in both young (1-2 month-old) and old (5-6 month-old) Kmt2d$^{+/+}$ and Kmt2d$^{+/\beta Geo}$ mice (FIG. 22C and FIG. 22D). Given the known cytotoxic potential of AR-42 (Huang et al. (2011) *Mol. Pharmacol.* 79:197-206; Zhang et al. (2011) *Int. J. Cancer.* 129:204-13), 5 and 10 mg/kg/day doses were next tested, and a dose-dependent increase in H3K4me3 and preservation or restoration of DCX expression in Kmt2d$^{+/+}$ or Kmt2d$^{+/\beta Geo}$ animals in both age groups, respectively, were observed (FIG. 23A, FIG. 23B, FIG. 23C, and FIG. 23D). This dose also led to a genome-wide increase in H3K4me3 in spleen cells from Kmt2d$^{+/\beta Geo}$ mice, when compared to Kmt2d$^{+/+}$ littermates on vehicle (FIG. 23E) in association with normalization of expression of Klf10 (FIG. 24), a known Kmt2d target gene (Guo et al. (2012) *Proc. Natl. Acad. Sci. U.S.A.* 109:17603-8). In fact, this dose appeared to overcorrect the deficiency (FIG. 23E) which can be observed when representing data as MA plots (FIG. 25A, FIG. 25B, FIG. 25C, FIG. 25D, and FIG. 25E) or visualizing the shifts in balance among the two states (FIG. 26A, FIG. 26B, FIG. 26C, FIG. 26D, and FIG. 26E). Other state combinations with the same representations were also compared, showing a relative normalization of genome-wide H3K4me3 in Kmt2d$^{+/\beta Geo}$ mice treated with AR-42, when compared to Kmt2d$^{+/+}$ littermates that did (FIG. 25E) or did not (FIG. 25B) receive drug. The bigger effect at lower intensity Log 2 (CPM) fits with data from ablation of Rubinstein-Taybi gene (CBP) which has dose dose-dependent effects on gene expression thought to depend on the strength of recruitment for a particular site (Kasper et al. (2010) *EMBO J.* 29:3660-72).

Improvement of hippocampal memory defects in Kmt2d$^{+/\beta Geo}$ mice treated with AR-42: In keeping with the hypothesis that abnormal GCL neurogenesis contributes to functional deficits, it was found that performance in hippocampal memory testing correlated with AR-42 dose-dependent effects on DCX expression. Specifically, both Kmt2d$^{+/+}$ and Kmt2d$^{+/\beta Geo}$ mice showed improved performance on Morris water maze platform crossing during probe trial (Garthe and Kempermann (2013) *Front Neurosci.* 7:63) in response to 10 mg/kg/day of AR-42, with a greater response in Kmt2d$^{+/\beta Geo}$ animals and no significant difference between genotypes in the treatment group (FIG. 23F).

Discussion

Prior studies have associated structural abnormalities of the dentate gyrus with impaired neurogenesis and hippocampal memory defects (Ansorg et al. (2012) *BMC Neurosci.* 13: 46; Denis-Donini et al. (2008) *J. Neurosci.* 28:3911-3919). In accordance with the previously observed phenotype in Mll4-targeted mice ((Kerimoglu et al. (2013) *J. Neurosci.* 33, 3452-64), it has been found that heterozygosity for a loss-of-function Kmt2d allele associates a deficiency of H3K4me3 in the dentate gyrus GCL with hippocampal memory defects in a mouse model of KS. Support for a causal relationship is now greatly enhanced by the observation disclosed herein that memory deficits can be prevented or even reversed through systemic delivery of drugs that directly influence the histone modification events that favor chromatin opening.

The data support the hypothesis that the neurodevelopmental deficiency in KS is maintained by an impairment of adult neurogenesis due to an imbalance between open and closed chromatin states for critical target genes. In this light, other Mendelian disorders involving the histone modification machinery (now numbering over 40; Berdasco and Esteller (2013) *Hum. Genet.* 132: 359-83) might be amenable to therapeutic intervention with HDAC inhibition (Dash et al. (2009) *Neuroscience* 163:1-8; Vecsey et al. (2007) *J. Neurosci.* 27: 6128-6140; Gräff and Tsai (2013) *Annu. Rev. Pharmacol. Toxicol.* 53:311-30). In keeping with this concept, neurological phenotypes in mouse models of Rubinstein-Taybi syndrome with haploinsufficiency for the gene encoding the histone acetyl transferase CREB binding protein (Cbp) respond to intracerebroventricular or intraperitoneal administration of the histone deacetylase inhibitors SAHA or trichostatin A, respectively (Korzus et al. (2004) *Neuron.* 42, 961-72; Alarcón et al. *Neuron.* 42, 947-59 (2004), however no cellular mechanism was described. The specific correlation between H3K4me3 and neurogenesis within the dentate gyrus of KS mice offers a potential unifying mechanism for hippocampal memory defects seen in inherited defects of the histone modification machinery (Gupta et al. (2010) *J. Neurosci.* 30:3589-99; Cohen-Armon et al. (2004) *Science* 304:1820-2; Korzus et al. (2004) *Neuron.* 42:961-72; Alarcón et al. (2004) *Neuron.* 42:947-59). The further positive correlation of these events with functional outcome supports the hypothesis that the fate of the GCL in the dentate gyrus is a critical determinant of both disease pathogenesis and treatment. More work is needed to determine the relative contribution of precursor cell recruitment, differentiation, proliferation and/or survival (Yang et al. (2012) *Mol. Cell. Biol.* 32:3121-31; Lubitz et al. (2007) *Mol. Biol. Cell.* 18:2356-66). Future studies using lineage-specific Kmt2d targeting will help elucidate the contribution of individual cell populations (GCL, pyramidal layer, molecular layer of the cerebellum) to specific neurodevelopmental phenotypes.

Although there is an overall decrease in H3K4me3 in the dentate gyrus GCL of Kmt2d$^{+/\beta Geo}$ mice, substantial cell-to-cell variation is noted. This might reflect redundancy of enzymes capable of adding the H3K4 trimethylation mark (Hunter et al. (2012) *Nucleic Acids Res.* 40: 306-12) that could vary in their expression level (and therefore compensation capacity) in a cell type—(e.g. differentiation state) or cell state—(e.g. electrochemical environment) dependent manner. Alternatively, this could indicate that stochastic events thought to contribute to epigenetic individuality (Bjornsson et al. (2004) *Trends Genet.* 20: 350-8) play a role.

There is precedent that HDACi not only increases histone acetylation, but also H3K4 trimethylation (Huang et al. (2011) *Mol. Pharmacol.* 79:197-206). The presently disclosed indicators nicely illustrate coupling between H4 acetylation and H3K4 trimethylation, with Kmt2d$^{+/\beta Geo}$ mice having defects in both systems. The novel reporter alleles described here have the potential for application in small molecule screens to identify drugs with greater potency, specificity and tolerance. There are also many FDA-approved medications, some with longstanding clinical use, that influence epigenetic modifications in addition to their originally established functions. An example is the anti-epileptic agent valproic acid, which was recently shown to be a potent HDACi (Phiel et al. (2001) *J. Biol. Chem.*

276:36734-41). Several widely-used supplements or dietary substances, such as folic acid, genestein, and curcumin, are known to influence epigenetic modifications (Meeran et al. (2010) *Clin. Epigenetics.* 1:101-116). A recent publication suggests that ketosis, as achieved in a ketogenic diet, might favor chromatin opening through beta-hydroxybutyrate, an endogenous HDACi (Shimazu et al. (2013) *Science* 339: 211-4). This indicates the potential that dietary manipulations, such as a ketogenic diet, might be another therapeutic avenue for treatment in disorders with a deficiency of open chromatin, such as KS. These observations may inform the question of potential toxicity of interventions that have broad effects on pervasive epigenetic events. The apparent tolerance to chronic use of such agents during postnatal life likely reflects, at least in part, the complex context within which gene transcription and ultimate function is achieved. Contributing factors include DNA modifications, a repertoire of both positive and negative effectors of transcription, and feedback mechanisms that titrate both gene expression and protein function. In this light, the predominant influence of agents such as HDACi as therapies may prove permissive for correction of pathologic alterations in physiologic gene expression and function rather than obligate and therefore less conducive to homeostasis.

Although a beneficial effect of AR-42 treatment on neurogenesis at two different ages (1-2 months and 5-6 months) was demonstrated, suggesting that this sub-phenotype of KS may be treatable even in adulthood, it is well established that neurogenesis potential is age-restricted (Martinez-Canabal et al. (2013) *Hippocampus* 23:66-74). It will be essential to further refine the window of opportunity to influence neurogenesis in the GCL in both mouse models and patients. It is also possible, but as yet unproven, that brief treatment in early postnatal stages will result in the expansion of a stable population of cells within the GCL (despite an ongoing relative deficiency of methyltransferase function) and hence achieve long-term recovery of neurologic function. Finally, the ChIP-seq experiments suggest that AR-42 at a dose of 10 mg/kg/day led to the most improvement in functional studies (FIG. 23D), but over-correction of genome-wide H3K4me3 (FIG. 23E). Given the favorable tolerance profile of high-dose HDACi when used for cancer treatment, this may not be a limiting factor. However, new challenges may arise when HDACi are used chronically for KS or other neurodevelopmental disorders. The combination of in vivo ChIP-seq analyses and in vitro reporter allele performance with regard to H3K4me3 status may ultimately allow optimization in the selection of agent and dose for therapeutic purposes.

Recent advances in Chromatin Immunoprecipitation-Sequencing (ChIP-seq) technologies (Brind'Amour et al. (2015) *Nat Commun.* 21;6:6033; Gilfillan G D et al. (2012) *BMC Genomics* November 21; 13:645) and related techniques, such as ATAC-seq (Buenrostro et al. (2015) *Curr Protoc Mol Biol.* 109:21.29.1-21.29.9), have been performed on cell numbers that can be practical to extract from patients (500-10,000 cells) with a simple blood draw. Accordingly, regarding the Mendelian disorders of the epigenetic machinery, chromatin immunoprecipitation of a mark defective in a particular disorder (e.g., H3K4me3 for KS and H4Ac for RTS) followed by some form of quantification (e.g., real time PCR, microarrays, or next generation sequencing) can be used as a diagnostic tool or a measurement of therapeutic efficiency. Examples include, but are not limited to, quantifying global levels of H3K4me3 in Kabuki syndrome (expected to be decreased), H3K27me3 in Kabuki syndrome (expected to be increased) and Weaver syndrome (expected to be decreased), and histone acetylation in Rubinstein-Taybi syndrome (expected to be decreased) and Brachydactyly-Mental Retardation (expected to be increased).

In conclusion, this work suggests that a postnatally ongoing and reversible deficiency of GCL H3K4me3 in association with adult neurogenesis underlies intellectual disability in a mouse model of KS. This work adds to the emerging view that multiple genetic etiologies of intellectual disability may be amenable to postnatal therapies (Guy et al. (2007) *Science* 315:1143-7; Das et al. (2013) *Sci. Transl. Med.* 5: 201ra120; Henderson et al. (2012) Sci. Transl. Med. 4:152ra128).

Example 2

Elevation of Beta-Hydroxybutyrate through Either Dietary Intervention or Exogenous Administration Rescues a Neurogenesis Defect in Kabuki Syndrome Introduction Kabuki syndrome (KS) is a rare genetic disease resulting in intellectual disability, seen in association with postnatal growth retardation, immunological dysfunction and characteristic facial features. Currently, there are two known genes, KMT2D and KDM6A, mutations in either of which can lead to KS (Ng et al. (2010) *Nat. Genet.* 42:790-3; Lederer et al. (2012) *Am. J. Hum. Genet.* 90:119-24; Miyake et al. (2013) *Hum. Mutat.* 34:108-10). Interestingly, each of these genes plays an independent role in the process of chromatin opening. KMT2D adds the open chromatin mark, H3K4me3, and KDM6A removes the closed chromatin mark H3K27me3 (Ng et al. (2010) *Nat. Genet.* 42:790-3; Lederer et al. (2012) *Am. J. Hum. Genet.* 90:119-24; Miyake et al. (2013) *Hum. Mutat.* 34:108-10). If a deficiency of chromatin opening plays a role in the pathogenesis of the disease, agents that favor chromatin opening, such as the histone deacetylase inhibitors (HDACi), could ameliorate any ongoing disease processes. Previously, a deficiency of adult neurogenesis, a dynamic process, has been observed in a mouse model of KS (Kmt2d$^{+/\beta Geo}$) associated with hippocampal memory deficits. These defects normalize upon a two-week course of the HDACi AR-42 (FIG. 29A). However, AR-42, like many other HDACis, is a cancer therapeutic agent (Zhang et al. (2008) *Genome Biol.* 9: R137) that will be difficult to transition to the clinic. An alternative approach would be to modify dietary intake to increase levels of beta-hydroxybutyrate (BHB), a ketone body and an endogenous HDACi (Shimazu et al. (2013) *Science* 339: 211-4) or alternatively inject BHB exogenously. While AR-42 has additional properties as an H3K4 demethylase inhibitor (Huang et al. (2011) *Mol. Pharmacol.* 79:197-20619) and this function may contribute to the previously observed therapeutic effect, it seems likely that BHB would be able to modulate histone modifications to influence the disease state, and thereby acting as a potential therapy for the previously described phenotypes of Kmt2d$^{+/\beta Geo}$ (FIG. 29A). Here, normalization of H3K4me3 in the granule cell layer (GCL) of the dentate gyrus (DG), rescue of the neurogenesis defect in the GCL of the DG and a rescue of the hippocampal memory defects in the mouse model of KS after mice were exclusively on ketogenic diet for two weeks is demonstrated. Furthermore, due to an abnormal NAD$^+$/NADH ratio, the KS mice have a natural propensity to elevate BHB preferentially compared to acetoacetate, the other endogenous ketone, making this a particularly effective intervention in these mice. A similar effect was also observed with exogenous administration of BHB. Taken together, these data suggest that dietary modulation of epigenetic modifications through natural elevation of BHB or exogenous administration of BHB may be a feasible treatment strategy for KS and related disorders.

Materials and Methods

Animals and treatment: The mouse model, Kmt2d$^{+/\beta Geo}$, also known as (Mll2Gt$^{(RRt024)Byg}$), was generated by BayGenomics (University of California, CA) through insertion of a gene trapped vector, and was used on a fully backcrossed C57BL/6J background. The original unbalanced (6:1 fat to protein ration) diet was purchased from Bio-Sery (Ketogenic Diet AIN-76A-Modified High Fat Paste F3666; Flemington, N.J.), while the balanced diet (4:1 ratio) was also from Bio-Serv (F6689 Rodent Diet, Ketogenic, Fat: Paste). Mice were treated for two weeks on the diet, with the paste replaced several times a week. During MWM testing, given the length of testing (week), the mice were treated for three weeks.

BHB injection and BHB assay: For injections into mice, (R)-(−)-3-hydroxybutyric acid sodium salt (Santa Cruz Biotechnology, Dallas, Tex.) was used at an experimental dose of (10 mM/kg). To detect BHB in the urine (from either injections or ketogenic diet), the β-Hydroxybutyrate (Ketone Body) Colorimetric Assay Kit (Cayman Chemical Company, Ann Arbor, Mich.) was used. Urine from injections was drawn approximately 2 hours after injection and urine from mice on the ketogenic diet was taken in the early afternoon (unless otherwise stated in the text).

Indicator experiments: HEK 293 cells were transfected with lipofectamine LTX (Invitrogen, Carlsbad, Calif.) with either the H3K4me3 indicator or the H4ac indicator, synthesized by OriGene Technologies (Rockville, Md.). Stable transfections were maintained through positive selection with blastacidin 10 mg/ml (Life Technologies, Grand Island, N.Y.). For BHB treatment, (R)-(−)-3-Hydroxybutyric acid sodium salt (Santa Cruz Biotechnology) was added to the medium 24 hours before FACS analysis (FACSVerse, BD Biosciences, Franklin Lakes, N.J.). Data was analyzed using FlowJo (Tree Star Inc., Ashland, Oreg.).

Serum lactate and pyruvate analysis: Serum was extracted from whole blood (spun down at 3500 g for 10 minutes and supernatant removed) and stored at −20° C. Serum samples were assayed for levels of lactate and pyruvate with the Lactate Assay Kit (Sigma-Aldrich, St. Louis, Mo.) and Pyruvate Assay Kit (Sigma-Aldrich).

Mass spectrometry for acetoacetate and beta-hydroxybutyrate: Acetoacetate and beta-hydroxybutyrate were prepared via acid extraction and BSTFA derivitization, and detected via gas chromatography-mass spectrometry. The mass spectrometer was set in SCAN mode to detect all mass fragments in a range of m/z 50-600. Compounds were identified based on their characteristic retention time and ion peaks. Results were reported as a ratio of acetoacetate to beta-hydroxybutyrate.

RNA extraction, microarray and QPCR: Hippocampi were dissected from four wild type regular diet and three Kmt2d+/− on a regular diet. RNA was extracted from hippocampi using the Qiagen RNeasy kit with the optional DNase treatment (Qiagen, Valencia, Calif.). RNA was preprocessed by the JHMI High Throughput Biology Center and hybridized to Affymetrix Mouse Gene 1.0 microarrays (Santa Clara, Calif.). Results were filtered by bar coding method and included for analysis if expression in two or more individual mice (Zilliox and Irizarry (2007) *Nat. Methods.* 4(11):911-3). Volcano plots were generated in Spotfire (TIBCO, Palo Alto, Calif.).

Perfusion, sectioning and, staining: For perfusion, cryosectioning and immunofluorescence staining, see Bjornsson et al. (2014). EdU (Life Sciences) in PBS/6% DMSO (10 mg/ml) injections (50 µg/g/day) were performed either with seven consecutive days followed by immediate perfusion or seven consecutive days of injection and then perfusion on the 30$^{th}$ day after the first injection. For staining, every sixth brain section was used, and blocking was done with 5% BSA. EdU was imaged with Click-iT EdU Alexa Flour 488 Imaging Kit (Invitrogen) as well as DAPI mounting with Vectamount (Vector Laboratories, Burlingame, Calif.). EdU quantification was done blinded to genotype. Labeled cells were counted in every sixth slice in the granule cell layer of the dentate gyrus and average number per slice was calculated for each brain. For immunofluorescence, primary antibodies included Doublecortin (Santa Cruz Biotechnology, 1:200 goat), trimethylated H3K4 (Cell Signaling, Danvers, Mass.; 1:500 rabbit), and Acetylated H3K9 and H3K14 (Cell Signaling, 1:5000). Primary antibodies were incubated overnight at 4° C. in blocking buffer.

Confocal microscopy: For confocal microscopy analysis of IF stained brains, Z-stack images were taken at either 10× using Zeiss Axiovert 200 (Carl Zeiss, Oberkochen, Germany) or 25× using Zeiss AxioExaminer multiphoton (Carl Zeiss). Fluorescence intensity was measured at 10× magnification by going to the midpoint of the z-stack using the Zen software (Carl Zeiss), dividing the fluorescence intensity of either the H3K4me3 or H3ac antibody by the DAPI fluorescence intensity, and normalizing to Kmt2d$^{+/+}$. Group comparisons were done with a student's t-test, with significance at $P<0.05$.

Doublecortin area measurement: The DCX positive fraction of the GCL was measured by taking 4× pictures and using the Bezier tool on NS elements 2.0 software (Nikon) to measure the area of cells that expressed DCX as well as the entire granule cell layer. The fraction of the GCL that showed DCX positive cells was then calculated, and group differences were analyzed using a students t-test with significance value set at $P<0.05$.

Behavior tests: Behavior testing was conducting on mice between 1-2 months of age, and was performed and analyzed blinded to genotype and treatment, with all experiments performed in the morning or afternoon.

For open field testing, Kmt2d$^{+/+}$ and Kmt2d$^{+/\beta Geo}$ mice were placed in their own open field chamber (San Diego Instruments, San Diego, Calif.) for ten 180 second intervals. These intervals were combined to give an average activity level, and treatment and genotype groups were compared with a students t-test with significance value set at $P<0.05$.

For grip strength testing, mice were allowed to grab onto the grip strength meter (Columbus Instruments, Columbus Ohio), and were lightly pulled by the tail with increasing force until they were pulled off. This was repeated 5 times for each mouse with the highest and lowest value being discarded, and averaging the three remaining values. Average grip strength for treatment and genotype groups was compared with a students t-test with significance value set at $P<0.05$.

For the Morris water maze, all testing were performed in a standard 1.1 meter diameter tank filled with white paint (Crayola) dyed water. The tank had a small platform submerged 2 cm below the water level in the middle of one of the four tank quadrants. For the first three days, the platform had a visible flag on top (Flag Training), and each mouse was placed in the tank for four consecutive 60 second trials in which they were trained to reach the visible platform. During each trial, the platform was moved to a different quadrant, but the mouse was always entered into the tank in the same location. Latency for each trial for each mouse was recorded, and if the mouse could not reach the platform in 60 seconds, they were placed there. Following flag training, the visible flag was removed, and for five days mice were trained to reach the now hidden platform (Hidden Platform Training), with four consecutive trials per mouse per day, with a maximum allotment of 60 seconds per trial. The platform was never moved, but for each trial, the mouse was entered into a different quadrant, with the order of these quadrants randomized for each day. On the final day (Probe Trial), the platform was removed and mice were allowed to swim for 90 seconds and the number of crossings over the previous location of the platform was measured. For training and probe tests, data were recorded both manually and electronically, with ANY-maze software (San Diego Instruments), when needed. The four genotype and treatment groups were analyzed for differences with a student t-test during the probe trial and with a repeated measures ANOVA for the latencies.

Results

The Kmt2d$^{+/\beta Geo}$ KS model (Bjornsson et al. (2014) *Sci. Transl. Med.* 6:256ra13) has now been backcrossed for 10 generations onto a C57BL/6J background (FIG. 30). After backcrossing, a deficiency of neurogenesis in the GCL of the DG (FIG. 31A) in association with hippocampal memory defects in the probe trial of a Morris water maze (P<0.001) in Kmt2d$^{+/\beta Geo}$ compared to Kmt2d$^{+/+}$ littermates (FIG. 31B) has continued to be observed. To explore whether there are genes that show downregulation in the hippocampus in Kmt2d$^{/\beta Geo}$ compared to Kmt2d$^{+/+}$ littermates, RNA from the hippocampus in both genotypes was isolated and 57 potential target genes were observed that show significantly (>0.5 log fold change, >0.5-log 10 adjusted P value) decreased expression in Kmt2d$^{+/\beta Geo}$ mice compared to Kmt2d$^{+/+}$ littermates but only 2 genes that demonstrate increased expression using same criteria (FIG. 29B). These targets include genes involved in CREB signaling in neurons (the process faulty in Rubinstein-Taybi syndrome, a related disorder with an overlapping phenotype), synaptic long-term potentiation, and glutamate signaling (data not shown). These results are consistent with the previously described (Bjornsson et al. (2014) *Sci. Transl. Med.* 6:256ra135) global deficiency of H3K4me3, which would be expected to preferentially lead to loss of expression of target genes.

To independently confirm histone deacetylase inhibitory activity of BHB in vitro, a previously described in vitro epigenetic reporter assay was used to analyze both H3K4me3 and H4Ac activity (Bjornsson et al. (2014) *Sci. Transl. Med.* 6:256ra135). A dose-dependent increased activity for either reporter after treatment with BHB was observed (FIG. 29C), suggesting that in addition to the histone deacetylase inhibitory activity of BHB, there may be additional effects on H3K4me3 (either direct or indirect). Therefore, in vivo treatments of mice on a standard ketogenic diet were undertaken, but deficiency of essential amino acids in addition to a ketogenic response was observed (data not shown). Upon administration of a more nutritionally balanced modified ketogenic diet (MKD) with a 4:1 fat to protein ratio to both Kmt2d$^{+/\beta Geo}$ mice and Kmt2d$^{+/+}$ littermates, it was found that the mice were protected from deficiency of essential amino acids (data not shown), but still demonstrated a significant increase in BHB levels as measured in the urine in both genotypes when comparing mice on and off the diet (P<0.05). Additionally, the level of BHB was significantly (P<0.05) increased in MKD treated Kmt2d$^{+/\beta Geo}$ compared to MKD treated Kmt2d$^{+/+}$ (FIG. 29D). Previously, a mouse model of Huntington's disease treated with a ketogenic diet also showed increased BHB levels (Ruskin et al. (2011) *Physiol. Behav.* 103:501-7) in mutants compared to wild type littermates, but this effect was attributed to a smaller size of the mutants compared to the wild type littermates (Ruskin et al. (2011) *Physiol. Behav.* 103:501-7), a phenotype shared with the Kmt2d$^{+/\beta Geo}$ model. Although an elevation of BHB with mass spectrometry was confirmed, the other major ketone, acetoacetate (AcAc), did not elevate to the same extent, indicating an increased BHB/AcAc ratio in diet treated Kmt2d$^{+/\beta Geo}$ mice compared to Kmt2d$^{+/+}$ littermates (FIG. 29E). Further analysis of serum from diet treated mice showed a significant (P<0.05) increase in the lactate/pyruvate ratio (FIG. 29F), another set of metabolites under the control of the NAD+/NADH ratio (White and Venkatesh (2011) *Crit. Care* 15, 219), indicating the potential of an underlying generalized redox imbalance (FIG. 29G).

As predicted by the in vitro ability of BHB to increase H3K4me3 and H4Ac activity and the known ability of BHB to cross the blood brain barrier, treatment of Kmt2d$^{+/\beta Geo}$ and Kmt2d$^{+/+}$ littermates with the MKD for two weeks also led to a significant increase in H3K4me3 in the granule cell layer of the dentate gyrus (P<0.05) compared to mice on a regular diet (FIG. 32A) with no difference between the two genotypes (P=0.09). A highly significant deficiency in H3Ac in this same cell population was observed between Kmt2d$^{+/\beta Geo}$ and control littermates (FIG. 33), as well as a significant increase (P<0.05) in H3Ac in Kmt2d$^{+/\beta Geo}$ on the modified ketogenic diet compared to untreated Kmt2d$^{+/\beta Geo}$ (FIG. 33). The neurogenesis defect previously observed in Kmt2d$^{+/\beta Geo}$ mice (P<0.001) was also rescued on the MKD as evaluated as the number of EdU+ cells in the GCL immediately after seven days of injections (proliferation) (P<0.001), as well as the number of EdU+ cells that remained 30 days after injection (P<0.05; survival; FIG. 32B) between Kmt2d$^{+/\beta Geo}$ treated and untreated on the diet. Similarly, Kmt2d$^{+/\beta Geo}$ mice treated with MKD showed a significant (P<0.05) increase in the doublecortin positive fraction of the granule cell layer when compared to Kmt2d$^{+/\beta Geo}$ on a regular diet, and showed no significant differences (P=0.2) when compared to MKD treated Kmt2d$^{+/+}$ littermate controls (FIG. 32C).

Figure 32D:
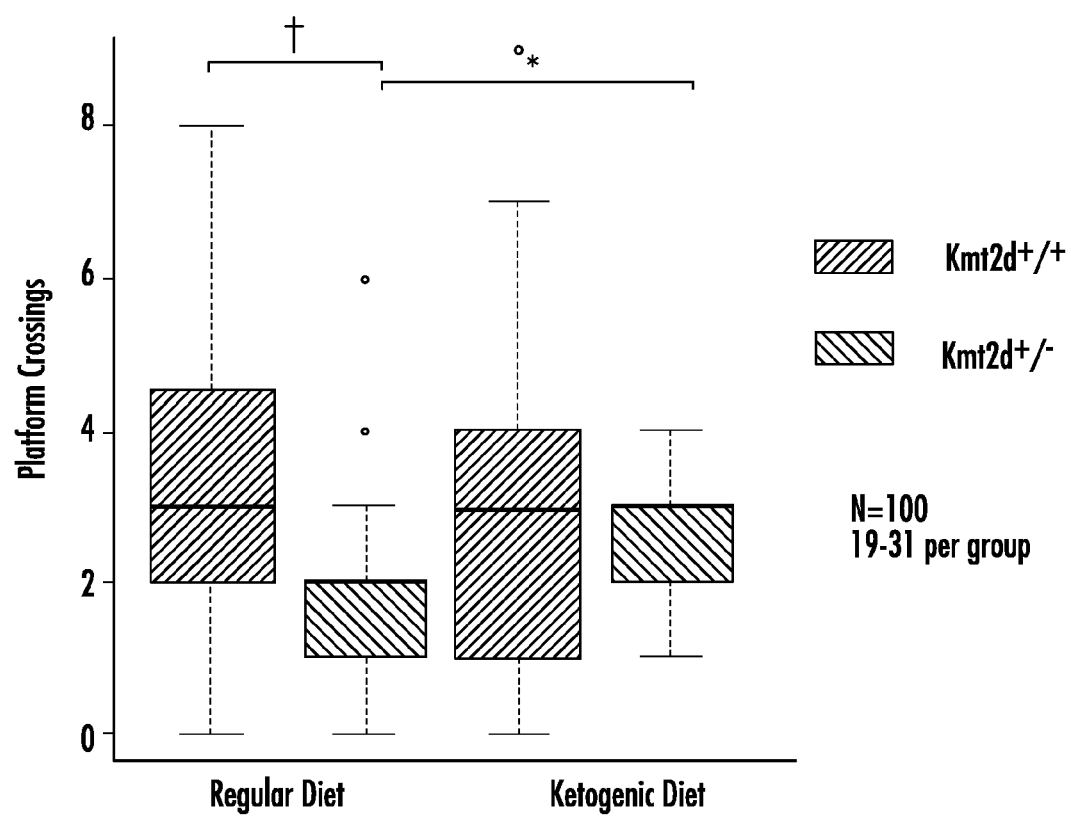

After a two-week treatment with the MKD, which was demonstrated to have increased the BHB level in treated mice (FIG. 29D), Kmt2d$^{+/\beta Geo}$ mice showed significant improvement (P<0.05) in platform crossings during the probe trial portion of MWM, and no significant (P=0.239) differences when compared to diet treated Kmt2d$^{+/+}$ controls (FIG. 32D). Swim latencies during the hidden platform portion of the water maze analyzed with a repeated measure ANOVA showed significant interaction between genotype and treatment (FIG. 34A), while the flag latency did not (FIG. 34B). Control tests for strength and activity (grip strength and open field testing) were unaffected by genotype, and only Kmt2d$^{+/+}$ on the ketogenic diet, and not Kmt2d$^{+/\beta Geo}$, showed an increase in activity (FIG. 35A and FIG. 35B); however, this has been previously described (Zhao et al. (2004) *Pediatr. Res.* 55, pp. 498-506) in previous treatments with a ketogenic diet.

To further test the hypothesis that BHB plays a critical role for the therapeutic benefits observed for Kmt2d$^{+/\beta Geo}$ mice on MKD, it was asked whether administration of BHB alone could similarly rescue the neurogenesis defect. Several doses of BHB were injected and urine was drawn at the time of maximal drug activity (1.5 hours; FIG. 36A), which guided the use of 10 mM/kg/day for two weeks for treatment on Kmt2d$^{+/\beta Geo}$ and Kmt2d$^{+/+}$ as well as vehicle treated controls. Vehicle treated Kmt2d$^{+/\beta Geo}$ showed a significant decrease in EdU expression compared to Kmt2d$^{+/+}$ ($P<0.001$), and BHB injected Kmt2d$^{+/\beta Geo}$ showed a significant increase in EdU expression compared to vehicle treated counterparts ($P<0.05$). However, as expected, given the much lower dose of BHB than achieved for ketogenic diet (FIG. 36D), the Kmt2d$^{+/\beta Geo}$ mice did not recover back to either Kmt2d$^{+/+}$ vehicle or Kmt2d$^{+/+}$ BHB treated (FIG. 36B). Similarly, BHB injected Kmt2d$^{+/\beta Geo}$ mice showed an increase in DCX expression compared to vehicle treated counterparts ($P<0.01$), although not to Kmt2d$^{+/+}$ BHB treated levels ($P<0.01$; FIG. 36C).

Discussion

A therapeutic response from HDAC inhibition through modulation of histone modifications with concurrent rescue of a neurogenesis defect observed in Kmt2d$^{+/\beta Geo}$ mice has been previously demonstrated (Bjornsson et al. (2014) *Sci. Transl. Med.* 6:256ra135). The presently disclosed subject matter expands upon this work by demonstrating that a ketogenic diet, previously used in a number of other conditions (Wheless, J. W. (2008), *Epilepsia,* 2008, 49: 3; Noh, H. S., et al., (2008) *Epilepsia,* 49: 120-123; Gasior et al. (2006) 17:431-439; Mantis et al. (2004) *Nutr. Metab.* (Lond) 1:11), can be used to elevate BHB to levels that are able to modulate histone modification in neuronal cells with a similar therapeutic benefit. This work therefore shows that a particular dietary regimen (in this case a ketogenic diet) is useful for a particular genotype (haploinsufficiency of KMT2D). Such targeted dietary interventions have been predicted among advocates of personalized medicine and nutrigenomics, although there are currently few robust examples (Estey et al. (2012) *Exp Gerontol* 47: 361-371; Niewinski (2008) *Am. Diet. Assoc.* 108, 661-672; Garcia-Canas et al. (2010) *J. Pharm. Biomed. Anal.* 51, 290-304). The benefits of dietary interventions include easier transfer to patients and more stable levels of histone deacetylase inhibition during treatment. Here, a redox state abnormality in KS is also demonstrated for the first time, which may actually make this particular intervention more feasible in these patients, as it may be easier to reach therapeutic levels of BHB.

It is interesting to note that while the HDACi properties of BHB have been well established (Shimazu et al. (2013) *Science* 339:211-4; Zhao et al. (2004) *Pediatr. Res.* 55, pp. 498-506), BHB has yet to be shown to increase H3K4me3. Here, it is reported that BHB demonstrates increased H3K4me3 activity in vitro in an epigenetic reporter assay and increases in vivo in the dentate gyrus granule cell layer.

Although the neurogenesis rescue appears similar between AR-42 and ketogenic diet treatments, H3K4me3 levels are elevated much more with AR-42 in both Kmt2d$^{+/\beta Geo}$ mice and Kmt2d$^{+/+}$ (Bjornsson et al. (2014) *Sci. Transl. Med.* 6:256ra135). This could relate to the dual role AR-42 has as both an HDACi and a histone demethylase inhibitor (Huang et al. (2011) *Mol. Pharmacol.* 79:197-20619). Interestingly in the behavioral testing phase, AR-42 shows improved performance for both genotypes (genotype independent improvement) but the MKD administration only leads to improvement for Kmt2d$^{+/\beta Geo}$ (genotype dependent improvement). The results shown hereinabove support a role for histone deacetylase inhibition as a treatment modality for Kabuki syndrome, and uncouple any non-specific genotype independent improved performance seen for AR-42.

The findings that exogenous sources of BHB can also rescue the neurogenesis defect give further credence to the hypothesis that it is the histone deacetylase inhibitory effect of BHB from which the therapeutic benefits of the ketogenic diet are derived. While a once daily treatment shows promise, in that Kmt2d$^{+/\beta Geo}$ mice on the diet showed increased neurogenesis compared to vehicle treated Kmt2d$^{+/\beta Geo}$, the lack of complete rescue further highlights the advantages of the steady levels of BHB provided by the diet. The ability to provide a constant level of HDACi without the need to monitor dosage levels lends further support to the potential of this therapeutic strategy.

In summary, the presently disclosed subject matter shows that the either the ketogenic diet or exogenous administration of BHB is an effective therapeutic approach for Kabuki syndrome and other related disorders of the histone machinery.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of treating Kabuki syndrome (KS) in a subject in need thereof, comprising administering to the subject a ketogenic composition in an amount sufficient to produce a physiologically acceptable ketosis in the subject and for a duration sufficient to treat KS in the subject.

2. A method of promoting a treatment for Kabuki syndrome (KS) in a subject in need thereof, wherein the treatment comprises administering a ketogenic composition in an amount sufficient to produce a physiologically acceptable ketosis in the subject and for a duration sufficient to promote treatment of KS in the subject.

3. The method of claim 1, wherein the ketogenic composition comprises a ketogenic diet.

4. The method of claim 3, wherein the ketogenic diet comprises a diet in which about 2% to about 15% by weight of its caloric content is carbohydrates, about 60% to about 90% by weight of its caloric content is fat, and about 8% or less by weight of its caloric content is protein.

5. The method of claim 1, wherein the ketogenic composition comprises a nutritionally balanced ketogenic diet.

6. The method of claim 5, wherein the nutritionally balanced ketogenic diet comprises a diet in which about 2% to about 15% by weight of its calcific content is carbohydrates, about 60% to about 90% by weight of its caloric content is fat, and about 8% to about 30% by weight of its caloric content is protein.

7. The method of claim 5, wherein the nutritionally balanced ketogenic diet comprises a 4:1 ratio of caloric fat content to caloric protein content.

8. The method of claim 1, wherein the ketogenic composition comprises a ready-to-drink beverage, powdered beverage formulation, nutritional or dietary supplement selected from the group consisting of gelatin capsule or tablet, suspension, parenteral solution, or a food product formulated for human consumption.

9. The method of claim 1, wherein the ketogenic composition comprises at least one ketogenic compound selected from the group consisting of
   i) a ketogenic amino acid selected from the group consisting of isoleucine, leucine, tryptophan, lysine, phenylalanine, tyrosine, aspartate β-semialdehyde, β-aspartylphosphate, saccharopine, α-aminoadipate δ-semialdehyde, and α-aminoadipate;
   ii) an immediate precursor of a ketogenic amino acid selected from the group consisting of α-ketoglutarate, indole, α-ketobutarate, L-histadinol, phenylpyruvate, 4-hydroxyphenylpyruvate, methyltetrahydrofolate, α-keto-β-methylvalerate, and α-ketoisovalerate;
   iii) an amino acid increasing molecule selected from the group consisting of a glutamate dehydrogenase, a valine aminotransferase, an arginosuccinate lyase, a tyrosine transaminase, an aromatic amino acid transaminase, a tryptophan synthase, and a histidinol dehydrogenase;
   iv) a medium chain triglyceride;
   v) a short chain fatty acid; and
   vi) combinations thereof.

10. The method of claim 1, wherein the ketogenic composition comprises at least one agent that promotes open chromatin states at one or more target genes in the subject.

11. The method of claim 10, wherein the agent decreases the level and/or activity of a histone deacetylase protein in the subject.

12. The method of claim 11, wherein the histone deacetylase protein is selected from the group consisting of histone deacetylase 1 (HDAC1), histone deacetylase 2 (HDAC2), histone deacetylase 3 (HDAC3), histone deacetylase 4 (HDAC4), histone deacetylase 5 (HDAC5), histone deacetylase 6 (HDAC6), histone deacetylase 7 (HDAC7), histone deacetylase 8 (HDAC8), histone deacetylase 9a (HDAC9a), histone deacetylase 9b (HDAC9b), histone deaceytlase 9c (HDAC9c), histone deaceytlase 10 (HDAC10), histone deacetylase 11 (HDAC11), SIRT1, SIRT2, SIRT3, SIRT4, SIRT5, SIRT6, and SIRT7.

13. The method of claim 10, wherein the agent increases the level of H3Kme4 in the subject.

14. The method of claim 10, wherein the agent decreases deacetylation of and/or increases trimethylation of lysine 4 of histone 3 in the subject.

15. The method of claim 10, wherein the at least one agent is selected from the group consisting of:
   i) D-β-hydroxybutyrate;
   ii) a salt of D-β-hydroxybutyrate;
   iii) a metabolic precursor of D-β-hydroxybutyrate;
   iv) an ester or polyester of D-β-hydroxybutyrate; and
   v) combinations thereof.

16. The method of claim 10, wherein the at least one agent is selected from the group consisting of
   i) (S-N-hydroxy-4-(3-methyl-2-phenylbutanamido)benzamide (AR-42);
   ii) 2-Propylpentanoic acid (valproic acid);
   iii) N'-hydroxy-N-phenyl-octanediamide (vorinostat); and
   iv) 5H-dibenz[b,f]azepine-5-carboxamide (carbamazepine).

17. The method of claim 1, wherein the ketogenic composition is administered at least once daily.

18. The method of claim 1, wherein the ketogenic composition is administered as part of a daily treatment regimen that lasts for at least two weeks.

19. The method of claim 1, wherein the ketogenic composition is administered as part of a daily treatment regimen that lasts for at least 6 months.

20. The method of claim 1, wherein the physiologically acceptable ketosis produced is such that the total concentration of β-hydroxybutyrate in the blood of the subject is raised to between 0.5 and 10 mM.

21. The method of claim 1, wherein the total concentration of β-hydroxybutyrate in the blood is raised to between 1 and 6 mM.

22. The method of claim 1, wherein a urinary excretion level of β-hydroxybutyrate is from about 5 to about 200 mg/dL.

23. The method of claim 1, wherein the subject is a human.

24. The method of claim 1, wherein the subject has, or is suspected of having, a redox imbalance.

25. The method of claim 1, further comprising determining whether the subject has a lysine (K)-specific methyltransferase 2D (KMT2D) gene mutation, a lysine (K)-specific demethylase 6A(KDM6A) gene mutation, or both.

* * * * *